United States Patent [19] [11] Patent Number: 5,968,967
Tanikawa et al. [45] Date of Patent: Oct. 19, 1999

[54] PYRAZOLONES DERIVATIVES

[75] Inventors: Keizo Tanikawa; Takashi Matsumoto; Masumi Nakamura; Yasunori Asada, all of Funabashi; Norimasa Shudo, Minamisaitama-gun, all of Japan

[73] Assignee: Nissan Chemical Industries, Ltd., Tokyo, Japan

[21] Appl. No.: 09/051,085

[22] PCT Filed: Oct. 11, 1996

[86] PCT No.: PCT/JP96/02944

§ 371 Date: Apr. 13, 1998

§ 102(e) Date: Apr. 13, 1998

[87] PCT Pub. No.: WO97/13757

PCT Pub. Date: Apr. 17, 1997

[30] Foreign Application Priority Data

Oct. 13, 1995 [JP] Japan ...................................... 7-265244
Sep. 3, 1996 [JP] Japan ...................................... 8-232868

[51] Int. Cl.[6] ........................ C07D 231/22; A61K 31/415
[52] U.S. Cl. ......................... 514/404; 514/252; 514/326; 544/371; 546/275.4; 548/369.7
[58] Field of Search ......................... 548/369.7; 544/371; 546/275.4; 514/404, 252, 326

[56] References Cited

U.S. PATENT DOCUMENTS 4,348,528 9/1982 Breda ...................................... 548/367

*Primary Examiner*—Robert Gerstl
*Attorney, Agent, or Firm*—Oblon, Spivak, McClelland, Maier & Neustadt, P.C.

[57] ABSTRACT

A pyrazolone derivative represented by general formula (I) or a salt thereof:

(I)

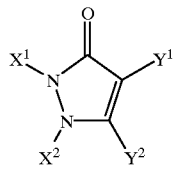

[wherein one of $X^1$ and $X^2$ is

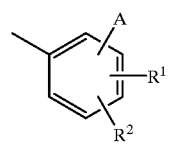

(wherein A is a cyano group, a cyano $C_{1-4}$ alkyl group, an amino group, an amino $C_{1-4}$ alkyl group, an amidino group or a guanidino group, $R^1$ and $R^2$ are independently hydrogen atoms, halogen atoms, $C_{1-6}$ alkyl groups or the like) or the like], the other of $X^1$ and $X^2$ is a $C_{1-6}$ alkyl group, a $C_{3-6}$ alkenyl group, an aryl $C_{1-4}$ alkyl group or an aryl group, one of $Y^1$ and $Y^2$ is

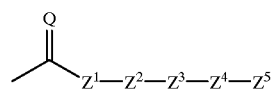

(wherein Q is an oxygen atom or a sulfur atom, $Z^1$ is an oxygen atom, a —$NR^7$— group or a —$CHR^7$— group, $Z^2$ is a cyclic $C_{3-7}$ alkylene group, a $C_{1-3}$ alkylene group, a —$CH_2CO$— group or —$CH_2CH_2CO$— group, $Z^3$ is an oxygen atom, a sulfur atom, a sulfinyl group, a sulfonyl group or the like, $Z^4$ is a $C_{1-3}$ alkylene group, and $Z^5$ is a carboxyl group or the like, and the other of $Y^1$ and $Y^2$ is a D-E- group [wherein E is a bond, a $C_{1-4}$ alkylene group or a phenylene group, and D is a hydrogen atom, a $C_{1-6}$ alkyl group or the like which has an inhibitory action on platelet aggregation and is useful as a preventive or therapeutic agent for various thrombotic diseases.

12 Claims, No Drawings

PYRAZOLONES DERIVATIVES

This application is a 371 of PCT/JP96/02944 filed Oct. 11, 1996.

TECHNICAL FIELD

The present invention relates to novel pyrazolone derivatives or their salts having an antiplatelet action, for use in the medicinal or veterinary field, especially in prevention or treatment of various thrombotic diseases.

BACKGROUND ART

Platelets play an important role in the normal hemostatic mechanism, and it has turned out that aggregation of platelets plays an important role in thrombogenesis from a pathological aspect. Major thrombotic diseases resulting from thrombogenesis include cerebral thrombosis, pulmonary thrombosis, myocardial infarction, cardiac angina and peripheral arterial obstruction and all of them require development of effective drugs. As preventive and therapeutic agents for these thrombotic diseases, antithrombotic agents having a platelet aggregation inhibitory action are drawing attention. Heretofore effects of aspirin have been studied extensively for a long time, and ticlopidine and cilostazol are used recently. However, the present situation is that drugs stronger in respect of efficacy are demanded.

A platelet has various membrane-binding glycoproteins including adhesive membrane proteins of the integrin super family on the membrane surface. The most plentiful integrin on the cell membrane of a normal platelet is GPIIb/IIIa. The GPIIb/IIIa on activated platelets binds a number of ligand proteins such as fibrinogen, fibronectin, vitronectin and the von Willebrand factor. These various ligands such as fibrinogen have the tripeptide sequence Arg-Gly-Asp (RGD), which is considered to be the most important site recognized for the binding. In recent years, compounds which inhibit GPIIb/IIIa from binding fibrinogen are assumed to be useful as antiplatelet agents, and chemical analogues of RGD have been examined on the usefulness as antiplatelet agents.

In addition to the above-mentioned thrombotic diseases, it is indicated that various diseases including nephritis and cancer cell metastasis are likely to be associated with platelets. Recently, extensive research is conducted on the preventive and therapeutic effects of antiplatelet agents which suppress the platelet function on these diseases.

The relevancy of the novel pyrazolone derivatives represented by general formula (I) and their pharmaceutically acceptable salts of the present invention to some compounds disclosed in the published literature is stated below.

(a) German patent publications No. 4124942 (hereinafter referred to as reference (a)) and No. 4302051 (hereinafter referred to as reference (a')) disclose pyrazolone derivatives but discloses nothing about their preparation, their specific examples or their medicinal activity.

(b) European patent publication No. 537696 (hereinafter referred to as reference (b)) discloses 3-alkoxypyrazole derivatives.

DISCLOSURE OF THE INVENTION

As a result of their extensive research, the present inventors have found unexpectedly that the pyrazolone derivatives of the present invention which are different from any of the compounds disclosed in references (a), (a') and (b) and their pharmaceutically acceptable salts are superior compounds as antiplatelet agents and can be an active ingredient of a preventive or therapeutic agent for the above-mentioned various thrombotic diseases. The present invention has been accomplished on the basis of this finding.

Namely, the present invention relates to a pyrazolone derivative represented by general formula (I) or a salt thereof:

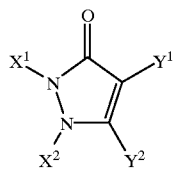

(I)

[wherein one of $X^1$ and $X^2$ is

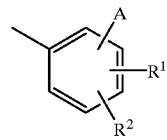

{wherein A is a cyano group, a cyano $C_{1-4}$ alkyl group, an amino group, an amino $C_{1-4}$ alkyl group, an amidino group or a guanidino group (the amino group, the amino $C_{1-4}$ alkyl group, the amidino group and the guanidino group may be substituted at a nitrogen atom with a $C_{1-6}$ alkyl group, a $C_{1-4}$ alkoxycarbonyl group, an aryl $C_{1-4}$ alkyloxycarbonyl group, an aryloxycarbonyl group or an arylcarbonyl group), $R^1$ and $R^2$ are independently hydrogen atoms, halogen atoms, $C_{1-6}$ alkyl groups, hydroxyl groups, $C_{1-4}$ alkyloxy groups, $C_{1-4}$ alkylsulfenyl groups, $C_{1-4}$ alkylsulfinyl groups, $C_{1-4}$ alkylsulfonyl groups, $R^3R^{3'}N$— groups or $R^3R^{3'}NCO$— groups, and $R^3$ and $R^{3'}$ are independently hydrogen atoms, $C_{1-6}$ alkyl groups, aryl $C_{1-4}$ alkyl groups, aryl groups, $C_{1-4}$ alkylcarbonyl groups, aryl $C_{1-4}$ alkylcarbonyl groups, arylcarbonyl groups, $C_{1-4}$ alkylsulfonyl groups, aryl $C_{1-4}$ alkylsulfonyl groups or arylsulfonyl groups}, a A-B- group (wherein A is the same as defined above, and B is a $C_{1-6}$ alkylene group, a $C_{3-6}$ alkenylene group or a cyclic $C_{3-7}$ alkylene group),

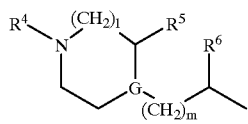

{wherein G is a nitrogen atom or a CH group, $R^4$ is a hydrogen atom, a $C_{1-6}$ alkyl group, a formyl group, an acetyl group, a benzyl group or an amidino group (the amidino group may be substituted with a $C_{1-6}$ alkyl group, a $C_{1-4}$ alkyloxycarbonyl group, an aryl $C_{1-4}$ alkyloxycarbonyl group, an aryloxycarbonyl group or an arylcarbonyl group), l is 0, 1 or 2, m is 1 or 2, and $R^5$ and $R^6$ are independently hydrogen atoms or $C_{1-6}$ alkyl groups or together represent a methylene group, an ethylene group or a —CH=CH— group} or

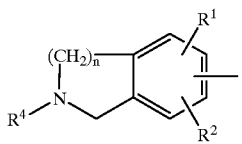

(wherein $R^1$, $R^2$ and $R^4$ are the same as defined above, and n is 1, 2 or 3), the other of $X^1$ and $X^2$ is a $C_{1-6}$ alkyl group, a $C_{3-6}$ alkenyl group, an aryl $C_{1-4}$ alkyl group or an aryl group, one of $Y^1$ and $Y^2$ is

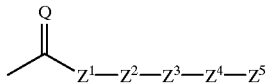

{wherein Q is an oxygen atom or a sulfur atom, $Z^1$ is an oxygen atom, a —$NR^7$— group or a —$CHR^7$— group, $Z^2$ is an cyclic $C_{3-7}$ alkylene group, a $C_{1-3}$ alkylene group, a —$CH_2CO$— group or a —$CH_2CH_2CO$— group (the $C_{1-3}$ alkylene group, the —$CH_2CO$— group and the —$CH_2CH_2CO$— group may be substituted with $R^8$), $Z^3$ is an oxygen atom, a sulfur atom, a sulfinyl group, a sulfonyl group or a —$NR^9$— group, $Z^4$ is a $C_{1-3}$ alkylene group (the $C_{1-3}$ alkylene group may be substituted with $R^{10}$), $Z^5$ is a carboxyl group, a $C_{1-4}$ alkyloxycarbonyl group, an aryl $C_{1-4}$ alkyloxycarbonyl group, an aryloxycarbonyl group, a sulfo group, a phosphono group, a O—$C_{1-4}$ alkylphosphono group, a O,O'-di-$C_{1-4}$ alkylphosphono group or a tetrazol-5-yl group, $R^7$ is a hydrogen atom, a $C_{1-6}$ alkyl group, an aryl $C_{1-4}$ alkyl group or an aryl group, or represents together with $R^8$ a methylene group or an ethylene group, or represents together with $R^9$ an ethylene group or a —$CH_2CO$— group when $Z^2$ is a methylene group or an ethylene group, $R^8$ is a $C_{1-6}$ alkyl group, an aryl $C_{1-4}$ alkyl group or an aryl group, or represents together with $R^7$ a methylene group or an ethylene group or represents together with $R^9$ a methylene group or an ethylene group, $R^9$ is a hydrogen atom, a formyl group, a $C_{1-4}$ alkylcarbonyl group, an arylcarbonyl group, a pyridylcarbonyl group, a $C_{1-6}$ alkyl group, an aryl $C_{1-4}$ alkyl group or an aryl group, or represents together with $R^8$ a methylene group or an ethylene group or represents together with $R^7$ an ethylene group or a —$COCH_2$— group when $Z^2$ is a methylene group or an ethylene group, and $R^{10}$ is a $C_{1-6}$ alkyl group, an aryl $C_{1-4}$ alkyl group or an aryl group}, and the other of $Y^1$ and $Y^2$ is a D-E- group [wherein E is a bond, a $C_{1-4}$ alkylene group or a phenylene group (the phenylene group may be substituted with a halogen atom, a hydroxyl group, a $C_{1-4}$ alkyloxy group or a $C_{1-6}$ alkyl group), and D is a hydrogen atom, a $C_{1-6}$ alkyl group,

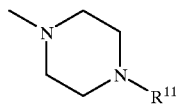

(wherein $R^{11}$ is a hydrogen atom, a $C_{1-6}$ alkyl group, a benzyl group or a formyl group), a pyridyl group or a phenyl group {the pyridyl group and the phenyl group may be substituted with a halogen atom, a hydroxyl group, a $C_{1-4}$ alkyloxy group, a $R^3R^{3'}N$— group, a $R^3R^{3'}NCO$— group (wherein $R^3$ and $R^{3'}$ are the same as defined above), a cyano group, an amidino group (which may be substituted at a nitrogen atom with a $C_{1-6}$ alkyl group, a $C_{1-4}$ alkoxycarbonyl group, an aryl $C_{1-4}$ alkyloxycarbonyl group, an aryloxycarbonyl group or an arylcarbonyl group) or a $C_{1-6}$ alkyl group}], wherein the aryl group is a phenyl group or a naphthyl group {the phenyl group and the naphthyl group may be substituted with a carboxyl group, a $C_{1-4}$ alkyloxycarbonyl group, a $C_{1-4}$ alkylcarbonyl group, a $R^3R^{3'}NCO$— group, a $R^3R^{3'}NSO_2$— group, a nitro group, a $R^3R^{3'}N$— group, a $C_{1-4}$ alkylsulfenyl group, a $C_{1-4}$ alkylsulfinyl group, a $C_{1-4}$ alkylsulfonyl group, a $C_{1-4}$ alkylcarbonyl-$NR^3$— group, a phenyl $C_{1-4}$ alkylcarbonyl-$NR^3$— group, a phenylcarbonyl-$NR^3$— group, a $C_{1-4}$ alkylsulfonyl-$NR^3$— group, a phenyl $C_{1-4}$ alkylsulfonyl-$NR^3$— group or a phenylsulfonyl-$NR^3$— group (wherein $R^3$ and $R^{3'}$ are the same as defined above), a halogen atom, a hydroxyl group, a $C_{1-4}$ alkyloxy group or a $C_{1-6}$ alkyl group}].

The above structural and chemical formulae are explained in further detail below.

As to A, the cyano $C_{1-4}$ alkyl group is cyanomethyl, cyanoethyl, cyano-n-propyl, cyano-i-propyl, cyano-n-butyl, cyano-i-butyl, cyano-s-butyl or cyano-t-butyl.

The amino $C_{1-4}$ alkyl group is aminomethyl, aminoethyl, amino-n-propyl, amino-i-propyl, amino-n-butyl, amino-i-butyl, amino-s-butyl or amino-t-butyl.

When A is an amino group, an amino $C_{1-4}$ alkyl group, an amidino group or a guanidino group, as to the substituents which the amino group, the amino $C_{1-4}$ alkyl group, the amidino group and the guanidino group may have, the $C_{1-6}$ alkyl group is methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

The $C_{1-4}$ alkyloxycarbonyl group is methoxycarbonyl, ethoxycarbonyl, n-propoxycarbonyl, i-propoxycarbonyl, n-butoxycarbonyl, i-butoxycarbonyl, s-butoxycarbonyl or t-butoxycarbonyl.

The aryl $C_{1-4}$ alkyloxycarbonyl group is arylmethoxycarbonyl, arylethoxycarbonyl, aryl-n-propoxycarbonyl, aryl-i-propoxycarbonyl, aryl-n-butoxycarbonyl, aryl-i-butoxycarbonyl, aryl-s-butoxycarbonyl or aryl-t-butoxycarbonyl.

Herein, aryl means the following groups whether it is alone or combined with other groups to form aryl $C_{1-4}$ alkyloxycarbonyl, aryloxycarbonyl, arylcarbonyl, aryl $C_{1-4}$ alkyl, aryl $C_{1-4}$ alkylcarbonyl, aryl $C_{1-4}$ alkylsulfonyl and arylsulfonyl.

Namely, the aryl group is a phenyl group, a 1-naphthyl group or a 2-naphthyl group (the phenyl group, the 1-naphthyl group and the 2-naphthyl group may be substituted with a carboxyl group, a $C_{1-4}$ alkyloxycarbonyl group, a $C_{1-4}$ alkylcarbonyl group, a $R^3R^{3'}NCO$— group, a $R^3R^{3'}NSO_2$— group, a nitro group, a $R^3R^{3'}N$— group, a $C_{1-4}$ alkylsulfenyl group, a $C_{1-4}$ alkylsulfinyl group, a $C_{1-4}$ alkylsulfonyl group, a $C_{1-4}$ alkylcarbonyl-$NR^3$— group, a phenyl $C_{1-4}$ alkylcarbonyl-$NR^3$— group, a phenylcarbonyl-$NR^3$— group, a $C_{1-4}$ alkylsulfonyl-$NR^3$— group, a phenyl $C_{1-4}$ alkylsulfonyl-$NR^3$— group, a phenylsulfonyl-$NR^3$— group, a halogen atom, a hydroxyl group, a $C_{1-4}$ alkyloxy group or a $C_{1-4}$ alkyl group), and as to the substituent, the $C_{1-4}$ alkyloxycarbonyl group is methoxycarbonyl, ethoxycarbonyl, n-propoxycarbonyl, i-propoxycarbonyl, n-butoxycarbonyl, i-butoxycarbonyl, s-butoxycarbonyl or t-butoxycarbonyl.

The $C_{1-4}$ alkylcarbonyl is methylcarbonyl, ethylcarbonyl, n-propylcarbonyl, i-propylcarbonyl, n-butylcarbonyl, i-butylcarbonyl, s-butylcarbonyl or t-butylcarbonyl.

$R^3$ or $R^{3'}$ in the $R^3R^{3'}NCO-$ group, the $R^3R^{3'}NSO_2-$ group, the $R^3R^{3'}N-$ group, the $C_{1-4}$ alkylcarbonyl-$NR^3-$ group, the phenyl $C_{1-4}$ alkylcarbonyl-$NR^3-$ group, the phenylcarbonyl-$NR^3-$ group, the $C_{1-4}$ alkylsulfonyl-$NR^3$ group, the phenyl $C_{1-4}$ alkylsulfonyl-$NR^3-$ group or the phenylsulfonyl-$NR^3-$ group is a hydrogen atom, methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl, 2-ethylbutyl, benzyl, 2-phenylethyl, 1-phenylethyl, 3-phenylpropyl, 2-phenylpropyl, 1-phenylpropyl, 4-phenylbutyl, 3-phenylbutyl, 2-phenylbutyl, 1-phenylbutyl, 2-phenyl-2-methylethyl, phenyl, 1-naphthyl, 2-naphthyl, methylcarbonyl, ethylcarbonyl, n-propylcarbonyl, i-propylcarbonyl, n-butylcarbonyl, i-butylcarbonyl, s-butylcarbonyl, t-butylcarbonyl, benzylcarbonyl, 2-phenylethylcarbonyl, 1-phenylethylcarbonyl, 3-phenylpropylcarbonyl, 2-phenylpropylcarbonyl, 1-phenylpropylcarbonyl, 4-phenylbutylcarbonyl, 3-phenylbutylcarbonyl, 2-phenylbutylcarbonyl, 1-phenylbutylcarbonyl, benzoyl, 1-naphthylcarbonyl, 2-naphthylcarbonyl, methanesulfonyl, ethanesulfonyl, n-propanesulfonyl, n-butanesulfonyl, benzylsulfonyl, 2-phenylethylsulfonyl, 3-phenylpropylsulfonyl, 4-phenylbutylsulfonyl or phenylsulfonyl.

As to $R^1$ and $R^2$, the halogen atom is a fluorine atom, a chlorine atom, a bromine atom or an iodine atom.

The $C_{1-6}$ alkyl group is methyl, ethyl, n-propyl, i-propyl, cyclopropyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

The $C_{1-4}$ alkyloxy group is methoxy, ethoxy, n-propoxy, i-propoxy, n-butoxy, i-butoxy, s-butoxy or t-butoxy.

The $C_{1-4}$ alkylsulfenyl group is methylthio, ethylthio, n-propylthio, i-propylthio, cyclopropylthio, n-butylthio, i-butylthio, s-butylthio or t-butylthio.

The $C_{1-4}$ alkylsulfinyl group is methylsulfinyl, ethylsulfinyl, n-propylsulfinyl, i-propylsulfinyl, cyclopropylsulfinylsulfinyl, n-butylsulfinyl, i-butylsulfinyl, s-butylsulfinyl or t-butylsulfinyl.

The $C_{1-4}$ alkylsulfonyl group is methanesulfonyl, ethanesulfonyl, n-propanesulfonyl or n-butanesulfonyl.

As to B, the $C_{1-6}$ alkylene group is methylene, ethylene, methylmethylene, n-propylene, i-propylene, dimethylmethylene, n-butylene, i-butylene, 1-methylpropylene, 2-methylpropylene, 3-methylpropylene, n-pentylene, 1-methylbutylene, 1, 2-dimethylpropylene, n-hexylene, 1-methylpentylene or 2-ethylbutylene.

The $C_{3-6}$ alkenylene group is allylene, 2-butenylene, 3-butenylene, 2-pentenylene, 4-pentenylene, 2-hexenylene or 5-hexenylene.

The cyclic $C_{3-7}$ alkylene group is cyclopropylene, cyclobutylene, cyclopentylene, cyclohexylene or cycloheptylene.

As to $R^4$, the $C_{1-6}$ alkyl group is methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

As to the substituent which an amidino group as $R^4$ may have, the $C_{1-6}$ alkyl group is methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

The $C_{1-4}$ alkyloxycarbonyl group is methoxycarbonyl, ethoxycarbonyl, n-propoxycarbonyl, i-propoxycarbonyl, n-butoxycarbonyl, i-butoxycarbonyl, s-butoxycarbonyl or t-butoxycarbonyl.

The aryl $C_{1-4}$ alkyloxycarbonyl group is arylmethoxycarbonyl, arylethoxycarbonyl, aryl-n-propoxycarbonyl, aryl-i-propoxycarbonyl, aryl-n-butoxycarbonyl, aryl-i-butoxycarbonyl, aryl-s-butoxycarbonyl or aryl-t-butoxycarbonyl.

As to $R^5$ and $R^6$, the $C_{1-6}$ alkyl group is methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

As to the other of $X^1$ and $X^2$, the $C_{1-6}$ alkyl group is methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

The $C_{3-6}$ alkenyl group is aryl, 1-butenyl, 2-butenyl, 3-butenyl, 1-pentenyl, 2-pentenyl, 3-pentenyl, 4-pentenyl, 2,4-pentadienyl, 1-hexenyl, 2-hexenyl, 3-hexenyl, 4-hexenyl, 5-hexenyl or 2,4-hexadienyl.

As to $R^7$, the $C_{1-6}$ alkyl group is methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

The aryl $C_{1-4}$ alkyl group is benzyl, 2-phenylethyl, 1-phenylethyl, 3-phenylpropyl, 2-phenylpropyl, 1-phenylpropyl, 4-phenylbutyl, 3-phenylbutyl, 2-phenylbutyl, 1-phenylbutyl, 1-naphthylmethyl, 2-naphthylmethyl, 2-(1-naphthyl)ethyl, 1-(1-naphthyl)ethyl, 3-(1-naphthyl)propyl, 2-(1-naphthyl)propyl, 1-(1-naphthyl)propyl, 4-(1-naphthyl)butyl, 3-(1-naphthyl)butyl, 2-(1-naphthyl)butyl, 1-(1-naphthyl)butyl, 2-(2-naphthyl)ethyl, 1-(2-naphthyl)ethyl, 3-(2-naphthyl)propyl, 2-(2-naphthyl)propyl, 1-(2-naphthyl)propyl, 4-(2-naphthyl)butyl, 3-(2-naphthyl)butyl, 2-(2-naphthyl)butyl or 1-(2-naphthyl)butyl.

When $R^7$ and $R^8$ together represent methylene or ethylene, $Z^1$-$Z^2$ is 1,2-aziridinylene, 1,3-azetidinylene, 1,2-azetidinylene, 1,3-pyrrolidinylene, 1,3-piperidinylene or 1,4-piperidinylene.

The cyclic C alkylene group as $Z^2$ is cyclopropylene, cyclobutylene, cyclopentylene, cyclohexylene or cycloheptylene.

As to $R^8$, the $C_{1-6}$ alkyl group is methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

The aryl $C_{1-4}$ alkyl group is benzyl, 2-phenylethyl, 1-phenylethyl, 3-phenylpropyl, 2-phenylpropyl, 1-phenylpropyl, 4-phenylbutyl, 3-phenylbutyl, 2-phenylbutyl, 1-phenylbutyl, 1-naphthylmethyl, 2-naphthylmethyl, 2-(1-naphthyl)ethyl, 1-(1-naphthyl)ethyl, 3-(1-naphthyl)propyl, 2-(1-naphthyl)propyl, 1-(1-naphthyl)propyl, 4-(1-naphthyl)butyl, 3-(1-naphthyl)butyl, 2-(1-naphthyl)butyl, 1-(1-naphthyl)butyl, 2-(2-naphthyl)ethyl, 1-(2-naphthyl)ethyl, 3-(2-naphthyl)propyl, 2-(2-naphthyl)propyl, 1-(2-naphthyl)propyl, 4-(2-naphthyl)butyl, 3-(2-naphthyl)butyl, 2-(2-naphthyl)butyl or 1-(2-naphthyl)butyl.

When $R^8$ and $R^9$ together represent methylene or ethylene, $Z^2$-$Z^3$ is 2,1-aziridinylene, 3,1-azetidinylene, 2,1-azetidinylene, 3,1-pyrrolidinylene, 3,1-piperidinylene, 4,1-piperidinylene or 2-oxo-4,1-pyperidinylene.

As to $R^9$, the $C_{1-4}$ alkylcarbonyl group is methylcarbonyl, ethylcarbonyl, n-propylcarbonyl, i-propylcarbonyl, n-butylcarbonyl, i-butylcarbonyl, s-butylcarbonyl or t-butylcarbonyl.

The arylcarbonyl group is benzoyl, 1-naphthylcarbonyl or 2-naphthylcarbonyl.

The pyridylcarbonyl group is 2-pyridylcarbonyl, 3-pyridylcarbonyl or 4-pyridylcarbonyl.

The $C_{1-6}$ alkyl group is methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

The aryl $C_{1-4}$ alkyl group is benzyl, 2-phenylethyl, 1-phenylethyl, 3-phenylpropyl, 2-phenylpropyl, 1-phenylpropyl, 4-phenylbutyl, 3-phenylbutyl, 2-phenylbutyl, 1-phenylbutyl, 1-naphthylmethyl, 2-naphthylmethyl, 2-(1-naphthyl)ethyl, 1-(1-naphthyl)ethyl, 3-(1-naphthyl)propyl, 2-(1-naphthyl)propyl, 1-(1-naphthyl)propyl, 4-(1-naphthyl)butyl, 3-(1-naphthyl)butyl, 2-(1-naphthyl)butyl, 1-(1-naphthyl)butyl, 2-(2-naphthyl)ethyl, 1-(2-naphthyl)ethyl, 3-(2-naphthyl)propyl, 2-(2-naphthyl)propyl, 1-(2-naphthyl)propyl, 4-(2-naphthyl)butyl, 3-(2-naphthyl)butyl, 2-(2-naphthyl)butyl or 1-(2-naphthyl)butyl.

When $Z^2$ is methylene or ethylene, and $R^7$ and $R^9$ together represent ethylene or —$CH_2CO$—, $Z^1$-$Z^2$-$Z^3$ is 1,3-imidazolidinylene, 4-oxo-1,3-imidazolidinylene, 1,4-piperazinylene or 3-oxo-1,4-piperazinylene.

As to $R^{10}$, the $C_{1-6}$ alkyl group is methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

The aryl $C_{1-4}$ alkyl group is benzyl, 2-phenylethyl, 1-phenylethyl, 3-phenylpropyl, 2-phenylpropyl, 1-phenylpropyl, 4-phenylbutyl, 3-phenylbutyl, 2-phenylbutyl, 1-phenylbutyl, 1-naphthylmethyl, 2-naphthylmethyl, 2-(1-naphthyl)ethyl, 1-(1-naphthyl)ethyl, 3-(1-naphthyl)propyl, 2-(1-naphthyl)propyl, 1-(1-naphthyl)propyl, 4-(1-naphthyl)butyl, 3-(1-naphthyl)butyl, 2-(1-naphthyl)butyl, 1-(1-naphthyl)butyl, 2-(2-naphthyl)ethyl, 1-(2-naphthyl)ethyl, 3-(2-naphthyl)propyl, 2-(2-naphthyl)propyl, 1-(2 -naphthyl)propyl, 4-(2-naphthyl)butyl, 3-(2-naphthyl)butyl, 2-(2-naphthyl)butyl or 1-(2-naphthyl)butyl.

As to $Z^5$, the $C_{1-4}$ alkyloxycarbonyl group is methoxycarbonyl, ethoxycarbonyl, n-propoxycarbonyl, i-propoxycarbonyl, n-butoxycarbonyl, i-butoxycarbonyl, s-butoxycarbonyl or t-butoxycarbonyl.

The aryl $C_{1-4}$ alkyloxycarbonyl group is arylmethoxycarbonyl, arylethoxycarbonyl, aryl-n-propoxycarbonyl, aryl-i-propoxycarbonyl, aryl-n-butoxycarbonyl, aryl-i-butoxycarbonyl, aryl-s-butoxycarbonyl or aryl-t-butoxycarbonyl.

The O—$C_{1-4}$ alkylphosphono group is methylphosphono, ethylphosphono, n-propylphosphono, i-propylphosphono, n-butylphosphono, i-butylphosphono, s-butylphosphono or t-butylphosphono.

The O,O'-di-$C_{1-4}$ alkylphosphono group is dimethylphosphono, diethylphosphono, di-n-propylphosphono, di-i-propylphosphono, di-n-butylphosphono, di-i-butylphosphono, di-s-butylphosphono, di-t-butylphosphono, methylethylphosphono or ethyl-n-propylphosphono.

The $C_{1-4}$ alkylene group as E is methylene, ethylene, methylmethylene, n-propylene, i-propylene, dimethylmethylene, n-butylene, i-butylene, 1-methylpropylene, 2-methylpropylene or 3-methylpropylene.

As to the substituent which a phenylene group as E may have, the halogen atom is a fluorine atom, a chlorine atom, a bromine atom or an iodine atom.

The $C_{1-4}$ alkyloxy group is methoxy, ethoxy, n-propoxy, i-propoxy, n-butoxy, i-butoxy, s-butoxy or t-butoxy.

The $C_{1-6}$ alkyl group is methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

The $C_{1-6}$ alkyl group as D is methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

As to $R^{11}$, the $C_{1-6}$ alkyl group is methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl or 2-ethylbutyl.

The pyridyl group is 2-pyridyl, 3-pyridyl or 4-pyridyl.

As to the substituent a pyridyl group or a phenyl group as D may have, the halogen atom is a fluorine atom, a chlorine atom, a bromine atom or an iodine atom.

The $C_{1-4}$ alkyloxy group is methoxy, ethoxy, n-propoxy, i-propoxy, n-butoxy, i-butoxy, s-butoxy or t-butoxy.

As to $R^3$ and $R^{3'}$ in the $R^3R^{3'}N$— group or the $R^3R^3$ NCO— group, is $R^3$ or $R^{3'}$ is a hydrogen atom, methyl, ethyl, n-propyl, i-propyl, n-butyl, i-butyl, s-butyl, t-butyl, n-pentyl, i-pentyl, s-pentyl, neopentyl, 1-methylbutyl, 1,2-dimethylpropyl, n-hexyl, 1-methylpentyl, 2-ethylbutyl, benzyl, 2-phenylethyl, 1-phenylethyl, 3-phenylpropyl, 2-phenylpropyl, 1-phenylpropyl, 4-phenylbutyl, 3-phenylbutyl, 2-phenylbutyl, 1-phenylbutyl, 2-phenyl-2-methylethyl, phenyl, 1-naphthyl, 2-naphthyl, 3-methylcarbonyl, ethylcarbonyl, n-propylcarbonyl, i-propylcarbonyl, n-butylcarbonyl, i-butylcarbonyl, s-butylcarbonyl, t-butylcarbonyl, benzylcarbonyl, 2-phenylethylcarbonyl, 1-phenylethylcarbonyl, 3-phenylpropylcarbonyl, 2-phenylpropylcarbonyl, 1-phenylpropylcarbonyl, 4-phenylbutylcarbonyl, 3-phenylbutylcarbonyl, 2-phenylbutylcarbonyl, 1-phenylbutylcarbonyl, benzoyl, 1-naphthylcarbonyl, 2-naphthylcarbonyl, methanesulfonyl, ethanesulfonyl, n-propanesulfonyl, n-butanesulfonyl, benzylsulfonyl, 2-phenylethylsulfonyl, 3-phenylpropylsulfonyl, 4-phenylbutylsulfonyl or phenylsulfonyl.

Among the compounds represented by general formula (1), the following compounds are preferred.

(1)

The pyrazolone derivatives represented by formula (I) or salts thereof, wherein one of $X^1$ and $X^2$ is

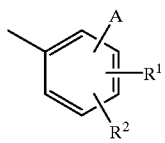

{wherein A is a cyano group, an amino group, an amidino group or a guanidino group (the amino group, the amidino group and the guanidino group may be substituted at a nitrogen atom with a $C_{1-6}$ alkyl group, a $C_{1-4}$ alkyloxycarbonyl group, an aryl $C_{1-4}$ alkyloxycarbonyl group, an aryloxycarbonyl group or an arylcarbonyl group), $R^1$ and $R^2$ are independently hydrogen atoms, halogen atoms, $C_{1-6}$ alkyl groups, hydroxyl groups, $C_{1-4}$ alkyloxy groups, $C_{1-4}$ alkylsulfenyl groups, $C_{1-4}$ alkylsulfinyl groups, $C_{1-4}$ alkylsulfonyl groups, $R^3R^{3'}N$— groups or $R^3R^{3'}NCO$— groups, and $R^3$ and $R^{3'}$ are independently hydrogen atoms, $C_{1-6}$ alkyl groups, aryl $C_{1-4}$ alkyl groups, aryl groups, $C_{1-4}$ alkylcarbonyl groups, aryl $C_{1-4}$ alkylcarbonyl groups, arylcarbonyl groups, $C_{1-4}$ alkylsulfonyl groups, aryl $C_{1-4}$ alkylsulfonyl groups or arylsulfonyl groups}, a A-B- group (wherein A is the same as defined above, and B is a $C_{1-6}$ alkylene group),

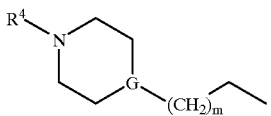

{wherein G is a nitrogen atom or a CH group, $R^4$ is a hydrogen atom, a $C_{1-6}$ alkyl group, a formyl group, an acetyl group, a benzyl group or an amidino group (the amidino group may be substituted with a $C_{1-6}$ alkyl group, a $C_{1-4}$ alkyloxycarbonyl group, an aryl $C_{1-4}$ alkyloxycarbonyl group, an aryloxycarbonyl group or an arylcarbonyl group), and m is 1 or 2} or

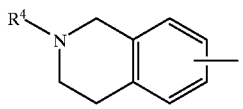

(wherein $R^4$ is the same as defined above), and
the other of $X^1$ and $X^2$ is a $C_{1-6}$ alkyl group, a $C_{3-6}$ alkenyl group, an aryl $C_{1-4}$ alkyl group or an aryl group.

(2)

The pyrazolone derivatives according to (1) or salts thereof, wherein one of $Y^1$ and $Y^2$ is

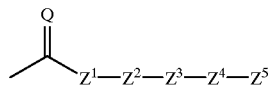

{wherein Q is an oxygen atom or a sulfur atom, $Z^1$ is an oxygen atom, a —$NR^7$— group or a —$CHR^7$— group, $Z^2$ is a cyclic $C_{3-7}$ alkylene group, a $C_{1-3}$ alkylene group, a —$CH_2CO$— group or a —$CH_2CH_2CO$— group, (the $C_{1-3}$ alkylene group, the —$CH_2CO$— group and the —$CH_2CH_2CO$— group may be substituted with $R^8$), $Z^3$ is an oxygen atom, a sulfur atom, a sulfinyl group, a sulfonyl group or a —$NR^9$— group, $Z^4$ is a $C_{1-3}$ alkylene group (the $C_{1-3}$ alkylene group may be substituted with $R^{10}$), $Z^5$ is a carboxyl group, a $C_{1-4}$ alkyloxycarbonyl group, an aryl $C_{1-4}$ alkyloxycarbonyl group, an aryloxycarbonyl group, a sulfo group, a phosphono group, a O—$C_{1-4}$ alkylphosphono group, a O,O'-di-$C_{1-4}$ alkylphosphono group or a tetrazol-5-yl group, $R^7$ is a hydrogen atom, a $C_{1-6}$ alkyl group, an aryl $C_{1-4}$ alkyl group or an aryl group, $R^9$ is a hydrogen atom, a formyl group, a $C_{1-4}$ alkylcarbonyl group, an arylcarbonyl group, a pyridylcarbonyl group, a $C_{1-6}$ alkyl group, an aryl $C_{1-4}$ alkyl group or an aryl group, and $R^8$ and $R^{10}$ are $C_{1-6}$ alkyl groups, aryl $C_{1-4}$ alkyl groups or aryl groups},

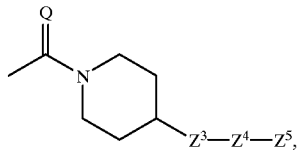

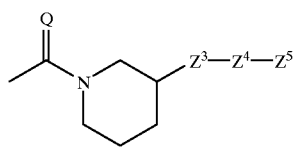

(wherein Q, $Z^3$, $Z^4$ and $Z^5$ are the same as defined above),

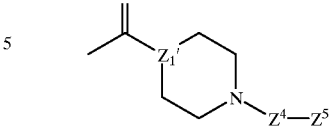

(wherein $Z^{1'}$ is a nitrogen atom or a $CR^7$ group, and Q, $R^7$, $Z^4$ and $Z^5$ are the same as defined above) or

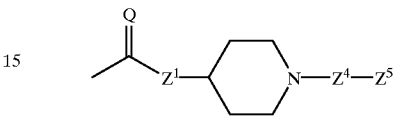

(wherein Q, $Z^1$, $Z^4$ and $Z^5$ are the same as defined above), and
the other of $Y^1$ and $Y^2$ is a D-E- group (wherein E is a bond, a $C_{1-4}$ alkylene group or a phenylene group (the phenylene group may be substituted with a halogen atom, a hydroxyl group, a $C_{1-4}$ alkyloxy group or a $C_{1-6}$ alkyl group), and D is a hydrogen atom, a $C_{1-6}$ alkyl group,

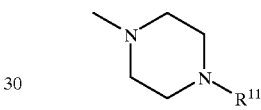

(wherein $R^{11}$ is a hydrogen atom, a $C_{1-6}$ alkyl group, a benzyl group or a formyl group), a pyridyl group or a phenyl group {the pyridyl group and the phenyl group may be substituted with a halogen atom, a hydroxyl group, a $C_{1-4}$ alkyloxy group, a $R^3R^{3'}N$— group, a $R^3R^{3'}NCO$— group (wherein $R^3$ and $R^{3'}$ are independently hydrogen atoms, $C_{1-6}$ alkyl groups, aryl $C_{1-4}$ alkyl groups, aryl groups, $C_{1-4}$ alkylcarbonyl groups, aryl $C_{1-4}$ alkylcarbonyl groups, arylcarbonyl groups, $C_{1-4}$ alkylsulfonyl groups, aryl $C_{1-4}$ alkylsulfonyl groups or arylsulfonyl groups), a cyano group, an amidino group (which may be substituted at a nitrogen atom with a $C_{1-6}$ alkyl group, a $C_{1-4}$ alkoxycarbonyl group, an aryl $C_{1-4}$ alkyloxycarbonyl group, an aryloxycarbonyl group or an arylcarbonyl group) or a $C_{1-6}$ alkyl group}].

(3)

The pyrazolone derivatives according to (2) or salts thereof, wherein Q is an oxygen atom.

(4)

The pyrazolone derivatives according to (3) or salts thereof, wherein $Y^1$ is

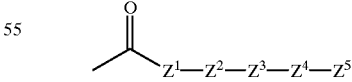

{wherein $Z^1$ is an oxygen atom, a —$NR^7$— group or a —$CHR^7$— group, $Z^2$ is a cyclic $C_{3-7}$ alkylene group, a $C_{1-3}$ alkylene group, a —$CH_2CO$— group or a —$CH_2CH_2CO$— group (the $C_{1-3}$ alkylene group, the —$CH_2CO$— group and the —$CH_2CH_2CO$— group may be substituted with $R^8$), $Z^3$ is an oxygen atom, a sulfur atom, a sulfinyl group, a sulfonyl group or a —$NR^9$— group, $Z^4$ is a $C_{1-3}$ alkylene group (the $C_{1-3}$ alkylene group may be substituted with $R^{10}$), $Z^5$ is a carboxyl group, a $C_{1-4}$ alkyloxycarbonyl group, an aryl $C_{1-4}$ alkyloxycarbonyl group, an aryloxycarbonyl group, a sulfo group, a phosphono group, a O—C$_{1-4}$ alkylphosphono group, a O,O'-di-C$_{1-4}$ alkylphosphono group or a tetrazol-5-yl group, R$^7$ is a hydrogen atom, a C$_{1-6}$ alkyl group, an aryl C$_{1-4}$ alkyl group or an aryl group, R$^9$ is a hydrogen atom, a formyl group, a C$_{1-4}$ alkylcarbonyl group, an arylcarbonyl group, a pyridylcarbonyl group, a C$_{1-6}$ alkyl group, an aryl C$_{1-4}$ alkyl group or an aryl group, and R$^8$ and R$^{10}$ are C$_{1-6}$ alkyl groups, aryl C$_{1-4}$ alkyl groups or aryl groups},

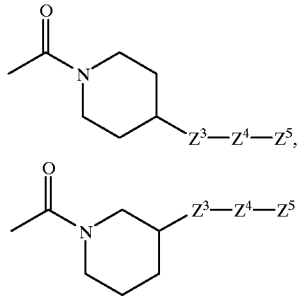

(wherein Z$^3$, Z$^4$ and Z$^5$ are the same as defined above),

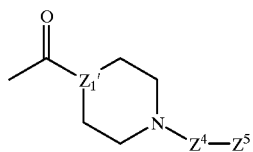

(wherein Z$^{1'}$ is a nitrogen atom or a CR$^7$ group, and R$^7$, Z$^4$ and Z$^5$ are the same as defined above) or

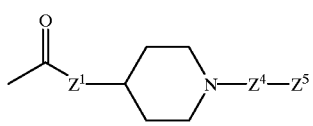

(wherein Z$^1$, Z$^4$ and Z$^5$ are the same as defined above), and Y$^2$ is a D-E- group [wherein E is a bond, a C$_{1-4}$ alkylene group or a phenylene group (the phenylene group may be substituted with a halogen atom, a hydroxyl group, a C$_{1-4}$ alkyloxy group or a C$_{1-6}$ alkyl group), and D is a hydrogen atom, a C$_{1-6}$ alkyl group,

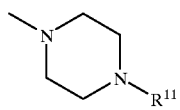

(wherein R$^{11}$ is a hydrogen atom, a C$_{1-6}$ alkyl group, a benzyl group or a formyl group), a pyridyl group or a phenyl group {the pyridyl group and the phenyl group may be substituted with a halogen atom, a hydroxyl group, a C$_{1-4}$ alkyloxy group, a R$^3$R$^{3'}$N— group, a R$^3$R$^{3'}$NCO— group (wherein R$^3$ and R$^{3'}$ are independently hydrogen atoms, C$_{1-6}$ alkyl groups, aryl C$_{1-4}$ alkyl groups, aryl groups, C$_{1-4}$ alkylcarbonyl groups, aryl C$_{1-4}$ alkylcarbonyl groups, arylcarbonyl groups, C$_{1-4}$ alkylsulfonyl groups, aryl C$_{1-4}$ alkylsulfonyl group or arylsulfonyl groups), a cyano group, an amidino group (which may be substituted at a nitrogen atom with a C$_{1-6}$ alkyl group, a C$_{1-4}$ alkoxycarbonyl group, an aryl C$_{1-4}$ alkyloxycarbonyl group, an aryloxycarbonyl group or an arylcarbonyl group) or a C$_{1-6}$ alkyl group}].

(5)
The pyrazolone derivatives according to (4) or salts thereof, wherein X$^1$ is

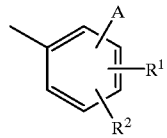

{wherein A is a cyano group, an amino group, an amidino group or a guanidino group (the amino group, the amidino group and the guanidino group may be substituted at a nitrogen atom with a C$_{1-6}$ alkyl group, a C$_{1-4}$ alkyloxycarbonyl group, an aryl C$_{1-4}$ alkyloxycarbonyl group, an aryloxycarbonyl group or an arylcarbonyl group), R$^1$ and R$^2$ are independently hydrogen atoms, halogen atoms, C$_{1-6}$ alkyl groups, hydroxyl groups, C$_{1-4}$ alkyloxy groups, C$_{1-4}$ alkylsulfenyl groups, C$_{1-4}$ alkylsulfinyl groups, C$_{1-4}$ alkylsulfonyl groups, R$^3$R$^{3'}$N— groups or R$^3$R$^{3'}$NCO— groups, and R$^3$ and R$^{3'}$ are independently hydrogen atoms, C$_{1-6}$ alkyl groups, aryl C$_{1-4}$ alkyl groups, aryl groups, C$_{1-4}$ alkylcarbonyl groups, aryl C$_{1-4}$ alkylcarbonyl groups, arylcarbonyl groups, C$_{1-4}$ alkylsulfonyl groups, aryl C$_{1-4}$ alkylsulfonyl groups or arylsulfonyl groups}, a A-B- group (wherein A is the same as defined above, and B is a C$_{1-6}$ alkylene group),

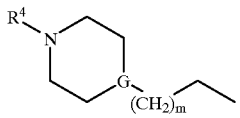

{wherein G is a nitrogen atom or a CH group, R$^4$ is a hydrogen atom, a C$_{1-6}$ alkyl group, a formyl group, an acetyl group, a benzyl group or an amidino group (the amidino group may be substituted with a C$_{1-6}$ alkyl group, a C$_{1-4}$ alkyloxycarbonyl group, an aryl C$_{1-4}$ alkyloxycarbonyl group, an aryloxycarbonyl group or an arylcarbonyl group), and m is 1 or 2} or

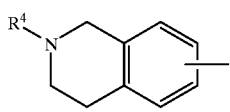

(wherein R$^4$ is the same as defined above), and X$^2$ is a C$_{1-6}$ alkyl group, a C$_{3-6}$ alkenyl group, an aryl C$_{1-4}$ alkyl group or an aryl group.

(6)
The pyrazolone derivatives according to (5) or salts thereof, wherein X$^1$ is

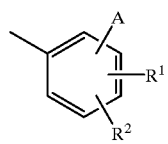

{wherein A is a cyano group, an amino group, an amidino group or a guanidino group (the amino group, the amidino group and the guanidino group may be substituted at a nitrogen atom with a C$_{1-6}$ alkyl group, a C$_{1-4}$ alkyloxycarbonyl group, an aryl C$_{1-4}$ alkyloxycarbonyl group, an aryloxycarbonyl group or an arylcarbonyl group), R$^1$ and R$^2$ are independently hydrogen atoms, halogen atoms, $C_{1-6}$ alkyl groups, hydroxyl groups, $C_{1-4}$ alkyloxy groups, $C_{1-4}$ alkylsulfenyl groups, $C_{1-4}$ alkylsulfinyl groups, $C_{1-4}$ alkylsulfonyl groups, $R^3R^3$ N— groups or $R^3R^3$ NCO— groups, and $R^3$ and $R^{3'}$ are independently hydrogen atoms, $C_{1-6}$ alkyl groups, aryl $C_{1-4}$ alkyl groups, aryl groups, $C_{1-4}$ alkylcarbonyl groups, aryl $C_{1-4}$ alkylcarbonyl groups, arylcarbonyl groups, $C_{1-4}$ alkylsulfonyl groups, aryl $C_{1-4}$ alkylsulfonyl groups or arylsulfonyl groups}, a $H_2N(CH_2)_k$— group (wherein k is an integer of from 1 to 6),

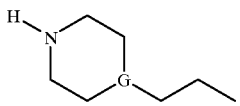

{wherein G is a nitrogen atom or a CH group) or

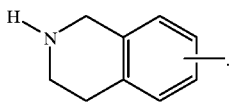

(7)

The pyrazolone derivatives according to (6) or salts thereof, wherein $X^1$ is

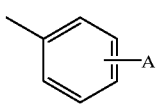

(wherein A is a cyano group or an amidino group), a $H_2N(CH_2)_k$— group (wherein k is an integer of from 1 to 6) or

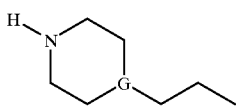

(wherein G is a nitrogen atom or a CH group), $X^2$ is a $C_{1-6}$ alkyl group, a $C_{3-6}$ alkenyl group, an aryl $C_{1-4}$ alkyl group or an aryl group, $Y^1$ is

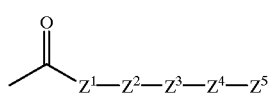

{wherein $Z^1$ is a —$NR^7$— group, $Z^2$ is a $C_{1-3}$ alkylene group, a —$CH_2CO$— group or a —$CH_2CH_2CO$— group, $Z^3$ is an oxygen atom or a —$NR^9$— group, $Z^4$ is a $C_{1-3}$ alkylene group (the $C_{1-3}$ alkylene group may be substituted with $R^{10}$), $Z^5$ is a carboxyl group, a $C_{1-4}$ alkyloxycarbonyl group, an aryl $C_{1-4}$ alkyloxycarbonyl group or an aryloxycarbonyl group, a cyano group, an amidino group (which may be substituted at a nitrogen atom with a $C_{1-6}$ alkyl group, a $C_{1-4}$ alkoxycarbonyl group, an aryl $C_{1-4}$ alkyloxycarbonyl group, an aryloxycarbonyl group or an arylcarbonyl group), and $R^{10}$ is a $C_{1-6}$ alkyl group, an aryl $C_{1-4}$ alkyl group or an aryl group},

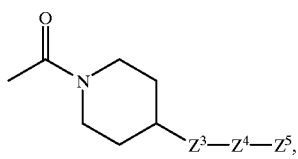

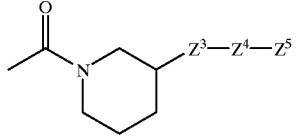

(wherein $Z^3$, $Z^4$ and $Z^5$ are the same as defined above),

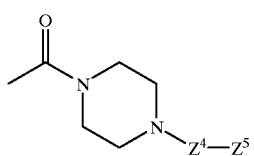

(wherein $Z^4$ and $Z^5$ are the same as defined above) or

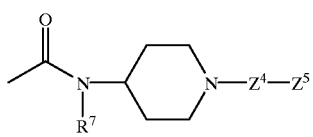

(wherein $R^7$, $Z^4$ and $Z^5$ are the same as defined above), and $Y^2$ is a hydrogen atom, a pyridyl group a biphenyl group (the pyridyl group and the biphenyl group may be substituted with a halogen atom, a hydroxyl group, a $C_{1-4}$ alkyloxy group or a $C_{1-6}$ alkyl group), a halogen atom, a hydroxyl group, a $C_{1-4}$ alkyloxy group, a $C_{1-6}$ alkyl group or a phenyl group (the phenyl group may be substituted with a halogen atom, a hydroxyl group, a $C_{1-4}$ alkyloxy group, a $C_{1-6}$ alkyl group, a pyridyl group or

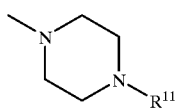

(wherein $R^{11}$ is a hydrogen atom, a $C_{1-6}$ alkyl group, a benzyl group or a formyl group)}.

(8)

The pyrazolone derivatives according to (6) or salts thereof, wherein $X^1$ is

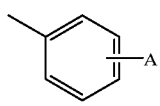

(wherein A is a cyano group or an amidino group), $X^2$ is a $C_{1-6}$ alkyl group, Y¹ is

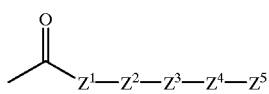

(wherein Z¹ is a —NR⁷— group, Z² is a $C_{1-3}$ alkylene group, Z³ is an oxygen atom or a —NR⁹— group, Z⁴ is a $C_{1-3}$ alkylene group, Z⁵ is a carboxyl group, a $C_{1-4}$ alkyloxycarbonyl group, an aryl $C_{1-4}$ alkyloxycarbonyl group or an aryloxycarbonyl group, R⁷ is a hydrogen atom, a $C_{1-6}$ alkyl group, an aryl $C_{1-4}$ alkyl group or an aryl group, and R⁹ is a hydrogen atom, a formyl group, a $C_{1-4}$ alkylcarbonyl group, an arylcarbonyl group, a pyridylcarbonyl group, a $C_{1-6}$ alkyl group, an aryl $C_{1-4}$ alkyl group or an aryl group),

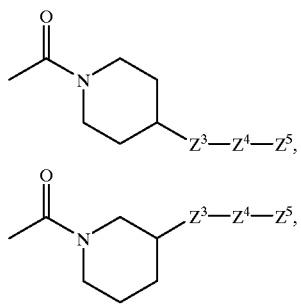

(wherein Z³, Z⁴ and Z⁵ are the same as defined above),

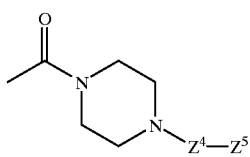

(wherein Z⁴ and Z⁵ are the same as defined above) or

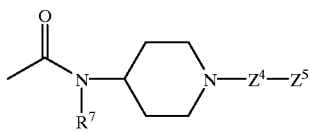

(wherein R⁷, Z⁴ and Z⁵ are the same as defined above), and

Y² is a hydrogen atom, a biphenyl group (the biphenyl group may be substituted with a cyano group, an amidino group or a halogen atom) or a phenyl group {the phenyl group may be substituted with a halogen atom, a pyridyl group, a $C_{1-6}$ alkyl group or

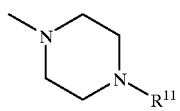

(wherein R¹¹ is a $C_{1-6}$ alkyl group)}.

Among the compound represented by general formula (I) of the present invention, those having a basic functional group such as an amidino group or an acidic functional group such as a carboxyl group may be converted to salts with appropriate acids or bases, if necessary.

Representatives of the pyrazolone derivatives represented by general formula (I) and their pharmaceutically acceptable salts of the present invention are listed in Table I, but the present invention is not limited to them.

As to the abbreviations, n means normal, i means iso, t means a tertiary group, Me means a methyl group, Et is an ethyl group, Pr is a propyl group, Bu is a butyl group, Ac is an acetyl group, Ph is a phenyl group, Ben is a Bz is a benzyl group, and Am means an amidino group.

Q1 to Q32 in Table I mean the following groups.

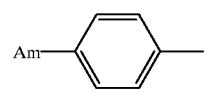
Q1

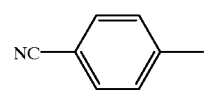
Q2

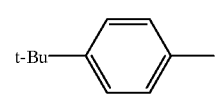
Q3

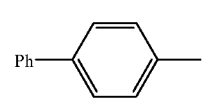
Q4

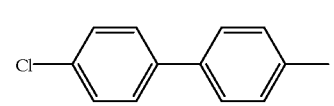
Q5

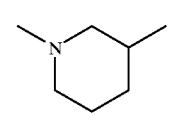
Q6

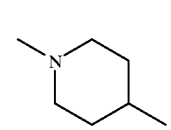
Q7

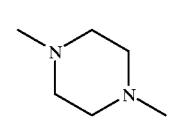
Q8

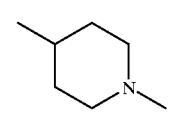
Q9

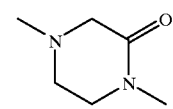
Q10

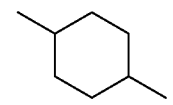
Q11

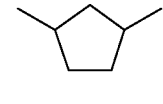
Q12

| | |
|---|---|
| | 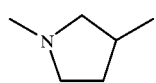 |
| | 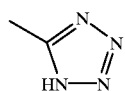 |
| | 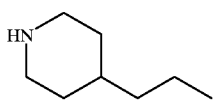 |
| | 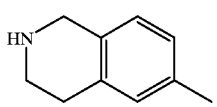 |
| | 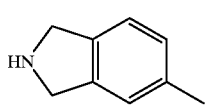 |
| | 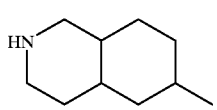 |
| | 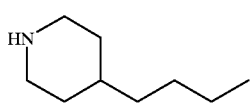 |
| | 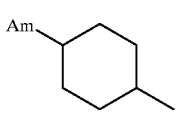 |
| | 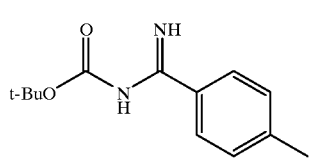 |
| | 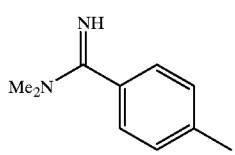 |
| | |
|---|---|
| Q13 | 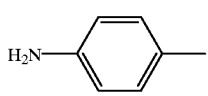 |
| Q14 | 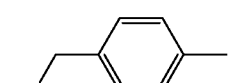 |
| Q15 | 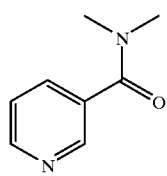 |
| Q16 | 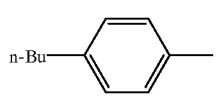 |
| Q17 |  |
| Q18 |  |
| Q19 | 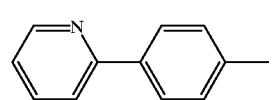 |
| Q20 | 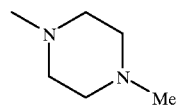 |
| Q21 | 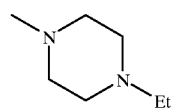 |
| Q22 | 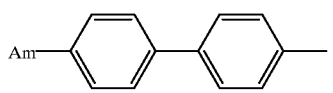 |
| Q23 | |
| Q24 | |
| Q25 | |
| Q26 | |
| Q27 | |
| Q28 | |
| Q29 | |
| Q30 | |
| Q31 | |
| Q32 | |

TABLE I

[Structure: pyrazolone with X¹-N-N(X²), Y² at 5-position, C(=Q) at 4-position connected to Z¹-Z²-Z³-Z⁴-Z⁵]

| No. | X¹ | X² | Q | Y² | Z¹ | Z² | Z³ | Z⁴ | Z⁵ |
|---|---|---|---|---|---|---|---|---|---|
| 1 | Q1.HCl | Me | O | H | NH | $CH_2CH_2$ | O | $CH_2$ | $CO_2H$ |
| 2 | Q1.HCl | Me | O | Q5 | —Q7— | | O | $CH_2$ | $CO_2Et$ |
| 3 | Q1.HCl | Me | O | H | NMe | $CH_2CH_2$ | O | $CH_2$ | $CO_2H$ |
| 4 | Q1.HCl | Me | O | H | NH | $CH_2CH_2$ | O | $CH_2$ | $CO_2Me$ |
| 5 | Q1.HCl | Me | O | H | N$^i$Pr | $CH_2CH_2$ | O | $CH_2$ | $CO_2H$ |
| 6 | Q1.HCl | Me | O | H | N$^i$Pr | $CH_2CH_2$ | O | $CH_2$ | $CO_2Me$ |
| 7 | Q1.HCl | Me | O | H | NH | $(CH_2)_3$ | O | $CH_2$ | $CO_2H$ |
| 8 | Q1.HCl | Me | O | H | —Q6— | | O | $CH_2$ | $CO_2H$ |
| 9 | Q1.HCl | Me | O | H | —Q6— | | O | $CH_2$ | $CO_2Et$ |
| 10 | Q1.HCl | Me | O | H | —Q7— | | O | $CH_2$ | $CO_2H$ |
| 11 | Q1.HCl | Me | O | H | —Q7— | | O | $CH_2$ | $CO_2Et$ |
| 12 | Q1.HCl | Me | O | Ph | NH | $CH_2CH_2$ | O | $CH_2$ | $CO_2H$ |
| 13 | Q1.HCl | Me | O | Ph | NH | $CH_2CH_2$ | O | $CH_2$ | $CO_2Et$ |
| 14 | Q1.HCl | Me | O | Ph | NMe | $CH_2CH_2$ | O | $CH_2$ | $CO_2H$ |
| 15 | Q1.HCl | Me | O | Ph | NMe | $CH_2CH_2$ | O | $CH_2$ | $CO_2Et$ |
| 16 | Q1.HCl | Me | O | Ph | N$^i$Pr | $CH_2CH_2$ | O | $CH_2$ | $CO_2H$ |
| 17 | Q1.HCl | Me | O | Ph | —Q7— | | O | $CH_2$ | $CO_2H$ |
| 18 | Q1.HCl | Me | O | Ph | —Q7— | | O | $CH_2$ | $CO_2Me$ |
| 19 | Q1.HCl | Me | O | Q4 | NH | $CH_2CH_2$ | O | $CH_2$ | $CO_2H$ |
| 20 | Q1.HCl | Me | O | Q4 | NH | $CH_2CH_2$ | O | $CH_2$ | $CO_2Et$ |
| 21 | Q1.HCl | Me | O | Q4 | NMe | $CH_2CH_2$ | O | $CH_2$ | $CO_2Me$ |
| 22 | Q1.HCl | Me | O | Q4 | —Q7— | | O | $CH_2$ | $CO_2H$ |
| 23 | Q1.HCl | Me | O | Q4 | —Q7— | | O | $CH_2$ | $CO_2Et$ |
| 24 | Q1.HCl | Me | O | Q3 | NH | $CH_2CH_2$ | O | $CH_2$ | $CO_2H$ |
| 25 | Q1.HCl | Me | O | Q3 | NH | $CH_2CH_2$ | O | $CH_2$ | $CO_2Et$ |
| 26 | Q1.HCl | Me | O | Q3 | NMe | $CH_2CH_2$ | O | $CH_2$ | $CO_2H$ |
| 27 | Q1.HCl | Me | O | Q3 | NMe | $CH_2CH_2$ | O | $CH_2$ | $CO_2Et$ |
| 28 | Q1.HCl | Me | O | Q3 | —Q7— | | O | $CH_2$ | $CO_2H$ |
| 29 | Q1.HCl | Me | O | Q3 | —Q7— | | O | $CH_2$ | $CO_2Et$ |
| 30 | Q1.HCl | Me | O | Q5 | NH | $CH_2CH_2$ | O | $CH_2$ | $CO_2H$ |
| 31 | Q1.HCl | Me | O | Q5 | NH | $CH_2CH_2$ | O | $CH_2$ | $CO_2Et$ |
| 32 | Q1.HCl | Me | O | H | NH | $CH_2CH_2$ | O | $CH_2$ | $CO_2Me$ |
| 33 | Q1.HCl | Me | O | Q5 | —Q7— | | O | $CH_2$ | $CO_2H$ |
| 34 | Q1.HCl | Me | O | Q3 | —Q8.HCl— | | | $CH_2$ | $CO_2Et$ |
| 35 | Q1.HCl | Me | O | Q4 | NMe | $CH_2CH_2$ | O | $CH_2$ | $CO_2Et$ |
| 36 | Q1.HCl | Me | O | Q5 | NMe | $CH_2CH_2$ | O | $CH_2$ | $CO_2Et$ |
| 37 | Q1.HCl | Me | O | Q3 | —Q8.HCl— | | | $CH_2$ | $CO_2H$ |
| 38 | Q1.HCl | Me | O | Q4 | NMe | $CH_2CH_2$ | O | $CH_2$ | $CO_2H$ |
| 39 | Q1.HCl | Me | O | Q5 | NMe | $CH_2CH_2$ | O | $CH_2$ | $CO_2H$ |
| 40 | Q1.HCl | Me | O | Q3 | NH | —Q9.HCl— | | $CH_2$ | $CO_2Et$ |
| 41 | Q1.HCl | Me | O | Q4 | —Q8.HCl— | | | $CH_2$ | $CO_2H$ |
| 42 | Q1.HCl | Me | O | Q4 | —Q8.HCl— | | | $CH_2$ | $CO_2Et$ |
| 43 | Q1.HCl | Me | O | Q3 | NH | —Q9.HCl— | | $CH_2$ | $CO_2H$ |
| 44 | Q1.HCl | Me | O | Q4 | NH | —Q9.HCl— | | $CH_2$ | $CO_2Et$ |
| 45 | Q1.HCl | Me | O | Q4 | —Q8.HCl— | | | $CH_2CH_2$ | $CO_2Et$ |
| 46 | Q1.HCl | Me | O | Q4 | NH | —Q9.HCl— | | $CH_2$ | $CO_2H$ |
| 47 | Q1.HCl | Me | O | Q4 | —Q8— | | | $CH_2CH_2$ | $CO_2H$ |
| 48 | Q2 | Me | O | H | NH | $CH_2CH_2$ | O | $CH_2$ | $CO_2{}^tBu$ |
| 49 | Q1.HCl | Me | S | H | NH | $CH_2CH_2$ | O | $CH_2$ | $CO_2H$ |
| 50 | Q1.HCl | Me | O | H | NH | Q11 | O | $CH_2$ | $CO_2Et$ |
| 51 | Q1.HCl | Me | O | H | NH | Q12 | O | $CH_2$ | $CO_2Et$ |
| 52 | Q1.HCl | Me | O | H | —Q13— | | O | $CH_2$ | $CO_2Et$ |
| 53 | Q2 | Me | O | H | NH | $CH_2CH_2$ | O | $CH_2$ | $CO_2Me$ |
| 54 | Q2 | Me | O | H | NMe | $CH_2CH_2$ | O | $CH_2$ | $CO_2{}^tBu$ |
| 55 | Q2 | Me | O | H | N$^i$Pr | $CH_2CH_2$ | O | $CH_2$ | $CO_2Me$ |
| 56 | Q2 | Me | O | H | —Q6— | | O | $CH_2$ | $CO_2Et$ |
| 57 | Q2 | Me | O | H | —Q7— | | O | $CH_2$ | $CO_2Et$ |
| 58 | Q2 | Me | O | Ph | NH | $CH_2CH_2$ | O | $CH_2$ | $CO_2Et$ |
| 59 | Q2 | Me | O | Ph | NMe | $CH_2CH_2$ | O | $CH_2$ | $CO_2Et$ |
| 60 | Q2 | Me | O | Ph | —Q7— | | O | $CH_2$ | $CO_2Et$ |
| 61 | Q2 | Me | O | Q4 | NH | $CH_2CH_2$ | O | $CH_2$ | $CO_2Et$ |
| 62 | Q2 | Me | O | Q4 | NMe | $CH_2CH_2$ | O | $CH_2$ | $CO_2Et$ |
| 63 | Q2 | Me | O | Q4 | —Q7— | | O | $CH_2$ | $CO_2Me$ |
| 64 | Q2 | Me | O | Q3 | NH | $CH_2CH_2$ | O | $CH_2$ | $CO_2Et$ |
| 65 | Q2 | Me | O | Q3 | NMe | $CH_2CH_2$ | O | $CH_2$ | $CO_2Me$ |
| 66 | Q2 | Me | O | Q3 | —Q7— | | O | $CH_2$ | $CO_2Et$ |
| 67 | Q2 | Me | O | Q5 | NH | $CH_2CH_2$ | O | $CH_2$ | $CO_2Et$ |

TABLE I-continued

[Structure: pyrazolone core with X¹-N-N(X²)-C(Y²)=C-C(=O)-Q attached to Z¹-Z²-Z³-Z⁴-Z⁵]

| No. | X¹ | X² | Q | Y² | Z¹ | Z² | Z³ | Z⁴ | Z⁵ |
|---|---|---|---|---|---|---|---|---|---|
| 68 | Q2 | Me | O | Q5 | | —Q7— | O | CH₂ | CO₂Et |
| 69 | Q1.HCl | Me | O | Ph | | —Q8.HCl— | | CH₂ | CO₂H |
| 70 | Q1.HCl | Me | O | Ph | NH | —Q9.HCl— | | CH₂ | CO₂H |
| 71 | Q1.HCl | Me | O | Ph | | —Q10— | O | CH₂ | CO₂H |
| 72 | Q1.HCl | Me | O | Ph | NH | CH₂CH₂ | O | CH₂CH₂ | CO₂H |
| 73 | Q1.HCl | Me | O | Ph | NH | CH₂CH₂ | NH | CH₂ | CO₂H |
| 74 | Q1.HCl | Me | O | Ph | NMe | CH₂CH₂ | NMe | CH₂ | CO₂H |
| 75 | Q1.HCl | Me | O | Ph | O | CH₂CH₂ | O | CH₂CH₂ | CO₂H |
| 76 | Q1.HCl | Et | O | Ph | NMe | CH₂CH₂ | O | CH₂ | CO₂H |
| 77 | Q1.HCl | ⁿPr | O | Ph | NMe | CH₂CH₂ | O | CH₂ | CO₂H |
| 78 | Q1.HCl | ⁱPr | O | Ph | NMe | CH₂CH₂ | O | CH₂ | CO₂H |
| 79 | Q1.HCl | Ben | O | Ph | NMe | CH₂CH₂ | O | CH₂ | CO₂H |
| 80 | Q1.HCl | (CH₂)₂Ph | O | Ph | NMe | CH₂CH₂ | O | CH₂ | CO₂H |
| 81 | Q1.HCl | CH₂CH=CH₂ | O | Ph | NMe | CH₂CH₂ | O | CH₂ | CO₂H |
| 82 | Q1.HCl | Me | O | Ph | NMe | CH₂CO | NMe | CH₂ | CO₂H |
| 83 | Q1.HCl | Ph | O | Ph | NMe | CH₂CH₂ | O | CH₂ | CO₂H |
| 84 | Q1.HCl | Me | O | Ph | NMe | CH₂ | O | CH₂ | CO₂H |
| 85 | Q1.HCl | Me | O | Ph | N(CH₂)₂Ph | CH₂CH₂ | O | CH₂ | CO₂H |
| 86 | Q1.HCl | Me | O | Ph | NPh | CH₂CH₂ | O | CH₂ | CO₂H |
| 87 | Q1.HCl | Me | O | Ph | NMe | CH₂CMe₂CH₂ | O | CH₂ | CO₂H |
| 88 | Q1.HCl | Me | O | Ph | NMe | CH₂CEt₂CH₂ | O | CH₂ | CO₂H |
| 89 | Q1.HCl | Me | O | Ph | NMe | CH₂CH₂ | O | CH₂ | SO₃H |
| 90 | Q1.HCl | Me | O | Ph | NMe | CH₂CH₂ | O | CH₂ | PO(OMe)₃ |
| 91 | Q1.HCl | Me | O | Ph | NMe | CH₂CH₂ | O | CH₂ | PO(OMe)₃ |
| 92 | Q1.HCl | Me | O | Ph | NMe | CH₂CH₂ | O | CH₂ | Q14 |
| 93 | Q15.HCl | Me | O | Ph | NMe | CH₂CH₂ | O | CH₂ | CO₂H |
| 94 | Q16.HCl | Me | O | Ph | NMe | CH₂CH₂ | O | CH₂ | CO₂H |
| 95 | Q17.HCl | Me | O | Ph | NMe | CH₂CH₂ | O | CH₂ | CO₂H |
| 96 | Q18.HCl | Me | O | Ph | NMe | CH₂CH₂ | O | CH₂ | CO₂H |
| 97 | Q19.HCl | Me | O | Ph | NMe | CH₂CH₂ | O | CH₂ | CO₂H |
| 98 | NC(CH₂)₄ | Me | O | Ph | NMe | CH₂CH₂ | O | CH₂ | CO₂H |
| 99 | NC(CH₂)₃ | Me | O | Ph | NMe | CH₂CH₂ | O | CH₂ | CO₂H |
| 100 | HCl.Am(CH₂)₄ | Me | O | Ph | NMe | CH₂CH₂ | O | CH₂ | CO₂H |
| 101 | HCl.Am(CH₂)₃ | Me | O | Ph | NMe | CH₂CH₂ | O | CH₂ | CO₂H |
| 102 | HCl.Q20 | Me | O | Ph | NMe | CH₂CH₂ | O | CH₂ | CO₂H |
| 103 | HCl.Q21 | Me | O | Ph | NMe | CH₂CH₂ | O | CH₂ | CO₂H |
| 104 | HCl.Q22 | Me | O | Ph | NMe | CH₂CH₂ | O | CH₂ | CO₂H |
| 105 | HCl.Q23 | Me | O | Ph | NMe | CH₂CH₂ | O | CH₂ | CO₂H |
| 106 | HCl.Q24 | Me | O | Ph | NMe | CH₂CH₂ | O | CH₂ | CO₂H |
| 107 | HCl.H₂N(CH₂)₄ | Me | O | Ph | NMe | CH₂CH₂ | O | CH₂ | CO₂H |
| 108 | HCl.H₂N(CH₂)₃ | Me | O | Ph | NMe | CH₂CH₂ | O | CH₂ | CO₂H |
| 109 | Q1.HCl | Me | O | Q3 | NH | —Q9— | | CH₂ | CO₂H |
| 110 | Q1.HCl | Me | O | Q3 | NH | —Q9— | | CH₂ | CO₂Et |
| 111 | Q1.HCl | Me | O | Q3 | NMe | —Q9— | | CH₂ | CO₂H |
| 112 | Q1.HCl | Me | O | Q3 | NMe | —Q9— | | CH₂ | CO₂Et |
| 113 | Q1.HCl | Me | O | Q3 | | —Q7— | NCHO | CH₂ | CO₂H |
| 114 | Q1.HCl | Me | O | Q3 | | —Q7— | NCHO | CH₂ | CO₂Et |
| 115 | Q1.HCl | Me | O | Q3 | | —Q7— | NMe | CH₂ | CO₂H |
| 116 | Q1.HCl | Me | O | Q3 | | —Q7— | NMe | CH₂ | CO₂Et |
| 117 | Q1.HCl | Me | O | Q3 | | —Q7— | NH | CH₂ | CO₂H |
| 118 | Q1.HCl | Me | O | Q3 | | —Q7— | NH | CH₂ | CO₂Et |
| 119 | Q1.HCl | Me | O | Q3 | | —Q7— | NAc | CH₂ | CO₂H |
| 120 | Q1.HCl | Me | O | Q3 | | —Q7— | NAc | CH₂ | CO₂Et |
| 121 | Q1.HCl | Me | O | Q3 | | —Q7— | NBz | CH₂ | CO₂H |
| 122 | Q1.HCl | Me | O | Q3 | | —Q7— | NBz | CH₂ | CO₂Et |
| 123 | Q1.HCl | Me | O | Q3 | | —Q7— | Q25 | CH₂ | CO₂H |
| 124 | Q1.HCl | Me | O | Q3 | | —Q7— | Q25 | CH₂ | CO₂Et |
| 125 | Q1.HCl | Me | O | Q4 | NH | —Q9— | | CH₂ | CO₂H |
| 126 | Q1.HCl | Me | O | Q4 | NH | —Q9— | | CH₂ | CO₂Et |
| 127 | Q1.HCl | Me | O | Q26 | | —Q7— | O | CH₂ | CO₂H |
| 128 | Q1.HCl | Me | O | Q26 | | —Q7— | O | CH₂ | CO₂Et |
| 129 | Q1.HCl | Me | O | Q27 | | —Q7— | O | CH₂ | CO₂H |
| 130 | Q1.HCl | Me | O | Q27 | | —Q7— | O | CH₂ | CO₂Et |
| 131 | Q1.HCl | Me | O | Q28 | | —Q7— | O | CH₂ | CO₂H |
| 132 | Q1.HCl | Me | O | Q28 | | —Q7— | O | CH₂ | CO₂Et |
| 133 | Q1.HCl | Me | O | Q29 | | —Q7— | O | CH₂ | CO₂H |
| 134 | Q1.HCl | Me | O | Q29 | | —Q7— | O | CH₂ | CO₂Et |

TABLE I-continued $$X^1-N\underset{\underset{Y^2}{\overset{N}{|}}}{\overset{\overset{O}{\|}}{C}}\overset{Q}{\underset{\|}{C}}-Z^1-Z^2-Z^3-Z^4-Z^5$$

| No. | X¹ | X² | Q | Y² | Z¹ | Z² | Z³ | Z⁴ | Z⁵ |
|---|---|---|---|---|---|---|---|---|---|
| 135 | Q1.HCl | Me | O | Q30 | —Q7— |  | O | CH₂ | CO₂H |
| 136 | Q1.HCl | Me | O | Q30 | —Q7— |  | O | CH₂ | CO₂Et |
| 137 | Q1.HCl | Me | O | Q31 | —Q7— |  | O | CH₂ | CO₂H |
| 138 | Q1.HCl | Me | O | Q31 | —Q7— |  | O | CH₂ | CO₂Et |
| 139 | Q2 | Me | O | Q3 | NH | —Q9— |  | CH₂ | CO₂Et |
| 140 | Q2 | Me | O | Q3 | NMe | —Q9— |  | CH₂ | CO₂Et |
| 141 | Q2 | Me | O | Q3 | —Q7— |  | NCHO | CH₂ | CO₂Et |
| 142 | Q2 | Me | O | Q3 | —Q7— |  | NMe | CH₂ | CO₂Et |
| 143 | Q2 | Me | O | Q3 | —Q7— |  | NAc | CH₂ | CO₂Et |
| 144 | Q2 | Me | O | Q3 | —Q7— |  | NBz | CH₂ | CO₂Et |
| 145 | Q2 | Me | O | Q3 | —Q7— |  | Q25 | CH₂ | CO₂Et |
| 146 | Q2 | Me | O | Q4 | NH | —Q9— |  | CH₂ | CO₂Et |
| 147 | Q2 | Me | O | Q26 | —Q7— |  | O | CH₂ | CO₂Et |
| 148 | Q2 | Me | O | Q27 | —Q7— |  | O | CH₂ | CO₂Et |
| 149 | Q2 | Me | O | Q28 | —Q7— |  | O | CH₂ | CO₂Et |
| 150 | Q2 | Me | O | Q29 | —Q7— |  | O | CH₂ | CO₂Et |
| 151 | Q2 | Me | O | Q30 | —Q7— |  | O | CH₂ | CO₂Et |
| 152 | Q2 | Me | O | Q32 | —Q7— |  | O | CH₂ | CO₂Et |
| 153 | Q1.HCl | Me | O | Q26 | —Q7— |  | NCHO | CH₂ | CO₂H |
| 154 | Q1.HCl | Me | O | Q26 | —Q7— |  | NCHO | CH₂ | CO₂Et |
| 155 | Q2 | Me | O | Q26 | —Q7— |  | NCHO | CH₂ | CO₂Et |

The compounds represented by general formula (I) can be used for the purpose of the present invention whether they are in the free state or in the form of salts.

Examples of such acid addition salts include mineral acid salts (hydrochlorides, hydrobromides, sulfates, hydrogensulfates, nitrates, phosphates, hydrogenphosphates and dihydrogenphosphates), organic acid salts (such as formates, acetates, propionates, succinates, malonates, oxalates, maleates, fumarates, malates, citrates, tartarates, lactates, glutamates, aspartates, picrates and carbonates) and sulfonates (such as methanesulfonates, benzenesulfonates and toluenesulfonates), and examples of salts with bases include alkali metal salts (such as lithium salts, sodium salts and potassium salts), alkaline earth metal salts (such as calcium salts and magnesium salts), aluminum salts, unsubstituted or methyl, ethyl or benzyl-substituted ammonium salts, organic amine salts (such as methylamine salts, ethylamine salts, dimethylamine salts, diethylamine salts, trimethylamine salts, triethyamine salts, cyclohexylamine salts, ethylenediamine salts, bicyclohexylamine salts, ethanolamine salts, diethanolamine salts, triethanolamine salts, piperazine salts, dibenzylpiperidine salts, dehydroabietylamine salts, N,N'-bisdehydroabietylamine salts, benzathine salts, N,N'-dibenzylethylenediamine salts, glucamine salts, N-methylglucamine salts, N-benzylphenethylamine salts, 2-amino-2-hydroxymethyl-1,3-propanediol salts, choline salts and procaine salts), basic amino acid salts (such as lysine salts, ornithine salts and arginine salts), pyridine salts, collidine salts and quinoline salts. These salts can be prepared by known methods.

BEST MODE FOR CARRYING OUT THE INVENTION

The pyrazolone derivatives represented by general formula (I) are prepared in accordance with the following synthetic processes.

The solvent used in their preparation is not particularly limited, but preferably a solvent which is stable under the reaction conditions and inert enough not to hinder the reactions. Such solvents include water, alcohols (such as methanol, ethanol, propanol, butanol and octanol), cellosolves (such as methoxyethanol and ethoxyethanol), aprotic polar organic solvents (such as dimethylformamide, dimethyl sulfoxide, dimethylacetamide, tetramethylurea, sulfolane and N,N-dimethylimidazolidinone), ethers (such as diethyl ether, diisopropyl ether, tetrahydrofuran and dioxane), aliphatic hydrocarbons (such as pentane, n-hexane, c-hexane, octane, decalin and petroleum ether), aromatic hydrocarbons (such as benzene, chlorobenzene, nitrobenzene, toluene, xylene and tetralin), halogenated hydrocarbons (such as chloroform, dichloromethane and dichloroethane), ketones (acetone, methyl ethyl ketone and methyl butyl ketone), lower fatty acid esters (such as methyl acetate, ethyl acetate and methyl propionate), alkoxyalkanes (such as dimethoxyethane and diethoxyethane) and acetonitrile. These solvents are used alone or in mixture after appropriate selection based on the probability of the reaction. In some cases, these solvents are used in the form of dehydrated solvents after dehydrated with appropriate dehydrating agents or desiccants. The above-mentioned solvents only exemplify the mode of carrying out the present invention, and the present invention is not restricted by these conditions.

Process 1

A process for producing a compound represented by general formula (I) wherein $Z^1$ is an oxygen atom or a —$NR^7$— group, which comprises reacting a compound represented by general formula (II):

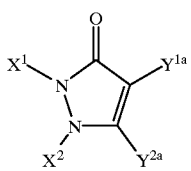

(II)

(wherein $X^1$ and $X^2$ are the same as defined above, one of $Y^{1a}$ and $Y^{2a}$ is a D-E- group {wherein E is a bond, a $C_{1-4}$ alkylene group or a phenylene group (the phenylene group may be substituted with a halogen atom, a hydroxyl group, a $C_{1-4}$ alkyloxy group or a $C_{1-6}$ alkyl group), and D is a hydrogen atom, a $C_{1-6}$ alkyl group,

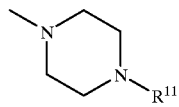

(wherein $R^{11}$ is a hydrogen atom, a $C_{1-6}$ alkyl group, a benzyl group or a formyl group), a pyridyl group or a phenyl group (the pyridyl group and the phenyl group may be substituted with a halogen atom, a hydroxyl group, a $C_{1-4}$ alkyloxy group, a $R^3R^{3'}N$— group, a $R^3R^{3'}NCO$— group (wherein $R^3$ and $R^{3'}$ are the same as defined above), a cyano group or a $C_{1-6}$ alkyl group)}, the other of $Y^{1a}$ and $Y^{2a}$ is a carboxyl group), with an amine represented by general formula (III):

$$HN(R^7)\text{-}Z^2\text{-}Z^3\text{-}Z^4\text{-}Z^5 \qquad (III)$$

(wherein $R^7$, $Z^2$, $Z^3$, $Z^4$ and $Z^5$ are the same as defined above) or with an alcohol represented by general formula (III'):

$$HO\text{-}Z^2\text{-}Z^3\text{-}Z^4\text{-}Z^5 \qquad (III')$$

(wherein $Z^2$, $Z^3$, $Z^4$ and $Z^5$ are the same as defined above), to obtain a compound represented by general formula (I) (wherein $Z^1$ is an oxygen atom or a —$NR^7$— group).

In the reaction, the compound (II) may be used in the form of a free carboxylic acid or a reactive derivative.

As the reactive derivative, an acid halide (such as an acid chloride and an acid bromide), a mixed acid anhydride [such as a mixed acid anhydride with a monoalkyl carbonate (for example a mixed acid anhydride derived from a free acid (II) and monomethyl carbonate, monoethyl carbonate, monoisopropyl carbonate, monoisobutyl carbonate, mono-t-butyl carbonate or monobenzyl carbonate), a mixed acid hydride with an alkyl carbonate (for example, a mixed acid hydride derived from a free acid (II) and acetic acid, cyanoacetic acid, propionic acid, butyric acid, isobutyric acid, valeric acid, isovaleric acid, pivalic acid, trifluoroacetic acid, trichloroacetic acid or acetoacetic acid), a mixed acid anhydride with an aromatic carboxylic acid (for example, a mixed acid anhydride derived from a free acid (II) and benzoic acid, p-toluic acid or p-chlorobenzoic acid), a mixed acid anhydride with an organic sulfonic acid (for example, a mixed acid anhydride derived from a free acid (II) and methanesulfonic acid, ethanesulfonic acid, benzenesulfonic acid or p-toluenesulfonic acid)], an active amide (such as an acid amide derived from a free acid (II) and pyrazole, imidazole or benzotriazole) or an active ester (such as a diethoxy phosphate ester, a diphenoxy phosphate ester, a p-nitrophenyl ester, a 2,4-dinitrophenyl ester, a cyanomethyl ester, a pentachlorophenyl ester, a N-hydroxysuccinimide ester, a N-hydroxyphthalimide ester, a 1-hydroxybenzotriazole ester, a 6-chloro-1-hydroxybenzotriazole ester or a 1-hydroxy-1H-2-pyridone ester) may be mentioned.

A reactive derivative of a compound (II) in a reaction mixture may be reacted with a compound (III) after isolated from the reaction mixture or without isolation.

When the compound (II) is in the form of a free carboxylic acid, an appropriate condensing agent is used. As the condensing agent, a N,N'-di-substituted carbodiimide such as N,N'-dicyclohexylcarbodiimide, an azoride such as N,N'-carbonyldiimidazole, a dehydrating agent such as N-ethoxycarbonyl-2-ethoxy-1,2-dihydroquinoline, phosphorus oxychloride or an alkoxyacetylene or a 2-halogenopyridinium salt such as 2-chloropyridinium methyliodide or 2-fluoropyridinium methyliodide may be used.

Compounds (III) and (III') are obtained through the pathway represented by:

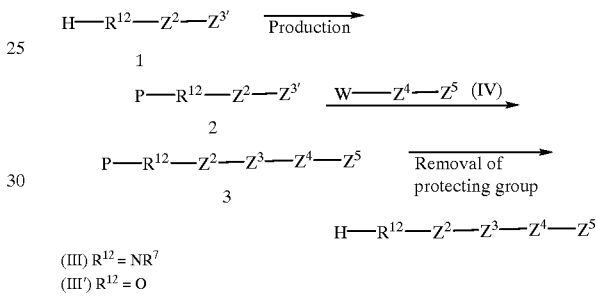

(III) $R^{12} = NR^7$
(III') $R^{12} = O$

{wherein $R^{12}$ is O or $NR^7$, P is a protecting group, W is a leaving group such as a halogen atom (such as a chlorine atom, a bromine atom or an iodine atom), mesylate, tosylate or triflate, $Z^{3'}$ is a —OH group or a —$NH(R^9)$ group, and $Z^2$, $Z^3$, $Z^4$, $Z^5$, $R^9$ and $R^7$ are the same as defined above}, namely by protecting 1 with an appropriate protecting group to obtain 2, reacting 2 with a compound (IV) to obtain 3 and removing the protecting group.

For the protecting group to be used and the method of removing the protecting group, "PROTECTIVE GROUPS IN ORGANIC CHEMISTRY" written by Greene, published by John Wiley and Sons, New York, 1991, can be referred to, and any protecting groups known in this field may be used. When $R^{12}$ is $NR^7$, the protecting group includes aliphatic carbamate (such as t-butoxycarbonyl, methoxycarbonyl, ethoxycarbonyl, 2,2,2-trichloroethylcarbonyl and allyloxycarbonyl), aromatic carbamate (such as benzyloxycarbonyl and 9-fluorenylmethoxycarbonyl), acyl (such as formyl, trifluoroacetyl and paratoluenesulfonyl), imide (such as phthaloyl) and benzyl, although it is not restricted thereto. When $R^{12}$ is O, the protecting group includes ether (such as benzyl, allyl, methoxymethyl, methoxyethoxymethyl and trimethylsilyl), sulfonate (such as methanesulfonyl and tolyl) and ester (such as acetyl, chloroacetyl, pivaloyl and allyloxycarbonyl), although it is not restricted thereto.

In the reaction which produces 3 from 2, when the leaving group as W is a chlorine atom or a bromine atom, sodium iodide or potassium iodide may be incorporated usually in an amount of from about 0.1 to 10 mols, preferably in an amount of about 0.1 to 2 mols in relation to the compound (IV), to accelerate the reaction.

The reaction is usually carried out in the presence of an appropriate base. As the base, for example, an organic amine (such as dimethylamine, diethylamine, diisopropylamine, trimethylamine, triethylamine, piperidine, piperazine, pyrrolidine, morpholine, pyridine, methanolamine or ethanolamine), a metal alkoxide (such as sodium methoxide, sodium ethoxide, lithium isopropoxide or potassium t-butoxide), an inorganic alkali metal salt (such as sodium hydroxide, potassium hydroxide, lithium hydroxide, potassium carbonate, sodium carbonate, sodium hydrogencarbonate, potassium hydrogencarbonate, sodium hydride, sodium acetate and potassium acetate) or an alkali metal amide (such as sodium amide) may be selected arbitrarily according to the probability of the reaction.

It is usually preferred to carry out the reaction in an appropriate solvent. As the solvent, any solvents that do not adversely affect the reaction can be used optionally.

A compound (II) is obtained by hydrolysis, treatment with an acid, pyrrolysis or hydrogenolysis of a compound represented by general formula (V):

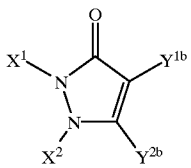

(V)

[wherein $X^1$ and $X^2$ are the same as defined above, one of $Y^{1b}$ and $Y^{2b}$ is a D-E- group (wherein E is a bond, a $C_{1-4}$ alkylene group or a phenylene group (the phenylene group may be substituted with a halogen atom, a hydroxyl group, a $C_{1-4}$ alkyloxy group or a $C_{1-6}$ alkyl group), and D is a hydrogen atom, a $C_{1-6}$ alkyl group,

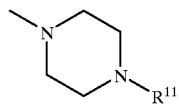

{wherein $R^{11}$ is a hydrogen atom, a $C_{1-6}$ alkyl group, a benzyl group or a formyl group), a pyridyl group or a phenyl group (the pyridyl group and the phenyl group may be substituted with a halogen atom, a hydroxyl group, a $C_{1-4}$ alkyloxy group, a $R^3R^{3'}N$— group, a $R^3R^{3'}NCO$— group (wherein $R^3$ and $R^{3'}$ are the same as defined above), a cyano group or a $C_{1-6}$ alkyl group)}, the other of $Y^{1b}$ and $Y^{2b}$ is a group convertible to a carboxyl group such as a —$CO_2R'$ group (wherein R' is a methyl group, an ethyl group, a t-butyl group, a benzyl group or the like)].

The hydrolysis is carried out in the presence of an appropriate acid (such as hydrochloric acid, sulfuric acid, phosphoric acid, trichloroacetic acid and trifluoroacetic acid) or an appropriate base (such as sodium hydroxide and potassium hydroxide) in water, an alcohol (such as methanol, ethanol and propanol) or an ether (such as tetrahydrofuran and dioxane) or in a mixture of these solvents at a temperature of from –20° C. to 120° C., preferably from atmospheric temperature to the boiling point of the solvent.

The t-butyl ester and the benzyl ester can be converted into carboxyl groups by treatment with an acid or pyrrolysis, and by hydrogenolysis, respectively.

Among the compounds (V), those wherein D is a $C_{1-4}$ alkyl group, a pyridyl group, a phenyl group {the pyridyl and the phenyl group may be substituted with a halogen atom, a hydroxyl group, a $C_{1-4}$ alkyloxy group, a $R^3R^{3'}N$— group or a $R^3R^{3'}NCO$— group (wherein $R^3$ and $R^{3'}$ are the same as defined above), a $C_{1-6}$ alkyl group or a cyano group are synthesized by the following processes.

a) A process which comprises treating a compound represented by

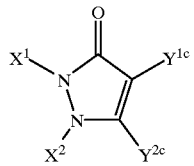

{wherein $X^1$ and $X^2$ are the same as defined above, one of $Y^{1c}$ and $Y^{2c}$ is a Hal-E- group (wherein E is the same as defined above, and Hal is a halogen atom), and the other of $Y^{1c}$ and $Y^{2c}$ is a group convertible to a carboxyl group such as a —COOR' group (wherein R' is the same as defined above)) with a zinc reagent D-Zn-Hal (wherein D and Hal are the same as defined above) or with a tin reagent D-Sn-$R^{13}_3$ (wherein D is the same as defined above, and $R^{13}$ is a $C_{1-4}$ alkyl group) in the presence of a transition metal catalyst, preferably a palladium catalyst.

As the palladium catalyst, tetrakis(triphenylphosphine) palladium[0], chlorobis(triphenylphosphine) benzylpalladium, bis[1,2-bis(diphenylphosphino)ethane] palladium or the like may be mentioned.

This reaction is carried out in an aromatic hydrocarbon (such as toluene), an ether (such as tetrahydrofuran), an aprotic polar organic solvent (such as dimethylformamide) or a mixture thereof.

b) A process which comprises treating

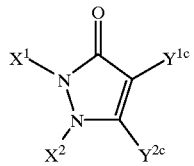

(wherein $X^1$, $X^2$, $Y^{1c}$ and $Y^{2c}$ are the same as defined above) with a boronic acid reagent D-B(OH)$_2$ (wherein D is the same as defined above). The reaction may be carried out in the presence of an appropriate base.

As the base, for example, organic amine (such as dimethylamine, diethylamine, diisopropylamine, trimethylamine, triethylamine, piperidine, piperazine, pyrrolidine, morpholine, pyridine, methanolamine or ethanolamine), a metal alkoxide (such as sodium methoxide, sodium ethoxide, lithium isopropoxide or potassium t-butoxide), an inorganic alkali metal salt (such as sodium hydroxide, potassium hydroxide, lithium hydroxide, potassium carbonate, sodium carbonate, sodium hydrogencarbonate, potassium hydrogencarbonate, sodium hydride, sodium acetate or potassium acetate) or an alkali metal amide (such as sodium amide) may be selected arbitrarily.

This reaction is preferably carried out in water, an alcohol (such as methanol or ethanol) or an ether (tetrahydrofuran) or a mixture thereof.

c) A process which comprises treating a zinc reagent represented by

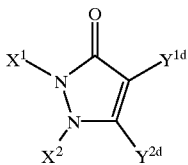

{wherein $X^1$ and $X^2$ are the same as defined above, one of $Y^{1d}$ and $Y^{2d}$ is a group convertible to a carboxyl group such as a —COOR' group (wherein R' is the same as defined above), and the other of $Y^{1d}$ and $Y^{2d}$ is a Hal-Zn-E- group (wherein E is the same as defined above, and Hal is a halogen atom)} or a tin reagent represented by

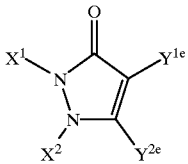

{wherein $X^1$ and $X^2$ are the same as defined above, one of $Y^{1e}$ and $Y^{2e}$ is a group convertible to a carboxyl group such as a —COOR' group (wherein R' is the same as defined above), and the other of $Y^{1e}$ and $Y^{2e}$ is $E\text{-Sn-}R^{13}_3$ (wherein D and $R^{13}$ are the same as defined above)} with E-Hal (wherein D is the same as defined above, and Hal is a halogen atom) in the presence of a transition metal catalyst, preferably a palladium catalyst.

As the palladium catalyst, tetrakis(triphenylphosphine) palladium[0], chlorobis(triphenylphosphine) benzylpalladium, bis[1,2-bis(diphenylphosphino)ethane] palladium or the like may be mentioned.

This reaction is carried out in an aromatic hydrocarbon (such as toluene) an ether (such as tetrahydrofuran), an aprotic polar organic solvent (such as dimethylformamide) or a mixture thereof.

d) A process which comprises treating a boronic acid reagent represented by

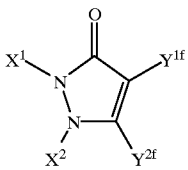

{wherein $X^1$ and $X^2$ are the same as defined above, one of $Y^{1f}$ and $Y^{2f}$ is a group convertible to a carboxyl group such as a —COOR' group (wherein R' is the same as defined above), and the other of $Y^{1f}$ and $Y^{2f}$ is a $\text{-E-B(OH)}_2$ group} with D-Hal (wherein D is the same as defined above, and Hal is a halogen atom).

This reaction may be carried out in the presence of an appropriate base. As the base, for example, an organic amine (such as dimethylamine, diethylamine, diisopropylamine, trimethylamine, triethylamine, piperidine, piperazine, pyrrolidine, morpholine, pyridine, methanolamine or ethanolamine), a metal alkoxide (such as sodium methoxide, sodium ethoxide, lithium isopropoxide or potassium t-butoxide), an inorganic alkali metal salt (such as sodium hydroxide, potassium hydroxide, lithium hydroxide, potassium carbonate, sodium carbonate, sodium hydrogencarbonate, potassium hydrogencarbonate, sodium hydride, sodium acetate or potassium acetate) or an alkali metal amide (such as sodium amide) may be selected arbitrarily.

This reaction is preferably carried out in water, an alcohol (such as methanol or ethanol), an ether (tetrahydrofuran) or a mixture thereof.

Among the compounds (V), those wherein D is

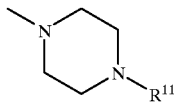

(wherein $R^{11}$ is the same as defined above) are prepared by the condensation reaction of a compound represented by

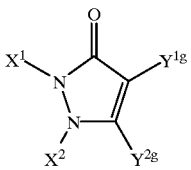

[wherein $X^1$ and $X^2$ are the same as defined above, one of $Y^{1g}$ and $Y^{2g}$ is a -E-Hal group (wherein E is the same as defined above, and Hal is a halogen atom), and the other of $Y^{1g}$ and $Y^{2g}$ is a group convertible to a carboxyl group such as a —COOR' group (wherein R' is the same as defined above)] with a piperazine derivative represented by general formula (VI)

(VI)

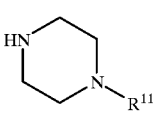

(wherein $R^{11}$ is the same as defined above).

In the reaction, an appropriate solvent may be used for dilution. Any solvent which does not adversely affect the reaction may be used arbitrarily as the solvent. The reaction may be carried out in the presence of an appropriate base.

As the base, for example, an organic amine (such as dimethylamine, diethylamine, diisopropylamine, trimethylamine, triethylamine, piperidine, piperazine, pyrrolidine, morpholine, pyridine, methanolamine or ethanolamine), a metal alkoxide (such as sodium methoxide, sodium ethoxide, lithium isopropoxide or potassium t-butoxide), an inorganic alkali metal salt (such as sodium hydroxide, potassium hydroxide, lithium hydroxide, potassium carbonate, sodium carbonate, sodium hydrogencarbonate, potassium hydrogencarbonate, sodium hydride, sodium acetate or potassium acetate) or an alkali metal amide (such as sodium amide) may be selected arbitrarily.

The compounds can also be obtained by the cyclization of a compound represented by

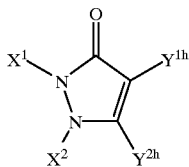

{wherein $X^1$ and $X^2$ are the same as defined above, one of $Y^{1h}$ and $Y^{2h}$ is E-NH$_2$, and the other of $Y^{1h}$ and $Y^{2h}$ is a group convertible to a carboxyl group such as a —COOR' group (wherein R' is the same as defined above)) with a halide represented by general formula

(wherein $R^{11}$ is the same as defined above, and Hal is a halogen atom). In this reaction, an appropriate solvent may be used for dilution. Any solvent that does not adversely affect the reaction may be used arbitrarily as the solvent. The reaction may be carried out in the presence of an appropriate base. As the base, for example, an organic amine (such as dimethylamine, diethylamine, diisopropylamine, trimethylamine, triethylamine, piperidine, piperazine, pyrrolidine, morpholine, pyridine, methanolamine or ethanolamine), a metal alkoxide (such as sodium methoxide, sodium ethoxide, lithium isopropoxide or potassium t-butoxide), an inorganic alkali metal salt (such as sodium hydroxide, potassium hydroxide, lithium hydroxide, potassium carbonate, sodium carbonate, sodium hydrogencarbonate, potassium hydrogencarbonate, sodium hydride, sodium acetate or potassium acetate) or an alkali metal amide (such as sodium amide) may be selected arbitrarily.

A compound (V) can be obtained also by cyclization reaction of a hydrazine derivative represented by general formula (VII):

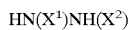

HN(X$^1$)NH(X$^2$)   (VII)

(wherein $X^1$ and $X^2$ are the same as defined above) with an α,β-unsaturated carbonyl compound represented by general formula (VIII):

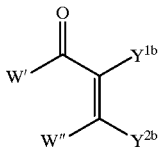

(VIII)

{wherein $Y^{1b}$ and $Y^{2b}$ are the same as defined above, and W' and W" are independently leaving groups such as halogen atoms (such as chlorine atoms, bromine atoms and iodine atoms), hydroxy, methoxy, ethoxy, mesylate, tosylate and triflate}.

In the reaction, an appropriate solvent may be used for dilution. Any solvent that does not adversely affect the reaction may be used arbitrarily as the solvent. The reaction may be carried out in the presence of an appropriate base. As the base, an organic amine (such as dimethylamine, diethylamine, diisopropylamine, trimethylamine, triethylamine, piperidine, piperazine, pyrrolidine, morpholine, pyridine, methanolamine or ethanolamine), a metal alkoxide (such as sodium methoxide, sodium ethoxide, lithium isopropoxide or potassium t-butoxide), an inorganic alkali metal salt (such as sodium hydroxide, potassium hydroxide, lithium hydroxide, potassium carbonate, sodium carbonate, sodium hydrogencarbonate, potassium hydrogencarbonate, sodium hydride, sodium acetate or potassium acetate) or an alkali metal amide (such as sodium amide) may be selected arbitrarily.

Process 2

A process for preparing a compound represented by general formula (I) wherein $Z^3$ is an oxygen atom or a —NR$^9$— group (wherein R$^9$ is the same as defined above), which comprises reacting a compound represented by general formula (IX):

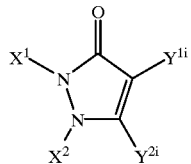

(IX)

[wherein $X^1$ and $X^2$ are the same as defined above, one of $Y^{1i}$ and $Y^{2i}$ is a D-E- group {wherein E is a bond, a $C_{1-4}$ alkylene group or a phenylene group (the phenylene group may be substituted with a halogen atom, a hydroxyl group, a $C_{1-4}$ alkyloxy group or a $C_{1-6}$ alkyl group), and D is a hydrogen atom, a $C_{1-6}$ alkyl group,

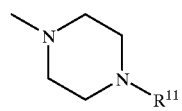

(wherein $R^{11}$ is a hydrogen atom, a $C_{1-6}$ alkyl group, a benzyl group or a formyl group), a pyridyl group or a phenyl group (the pyridyl and phenyl groups may be substituted with a halogen atom, a hydroxyl group, a $C_{1-4}$ alkyloxy group, a R$^3$R$^{3'}$N— group, a R$^3$R$^{3'}$NCO— group (wherein R$^3$ and R$^{3'}$ are the same as defined above), a cyano group or a $C_{1-6}$ alkyl group)), and the other of $Y^{1i}$ and $Y^{2i}$ is

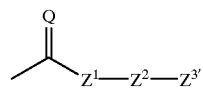

(wherein $Z^3$ is a —OH group or a —NH(R$^9$) group, and R$^9$, Q, $Z^1$ and $Z^2$ are the same as defined above)] with a compound represented by general formula (IV):

W-Z$^4$-Z$^5$   (IV)

{wherein W is a leaving group such as a halogen atom (such as a chlorine atom, a bromine atom or an iodine atom), mesylate, tosylate or triflate, and $Z^4$ and $Z^5$ are the same as defined above) to obtain a compound represented by formula (I) (wherein $Z^3$ is an oxygen atom or a —NR$^9$— group).

When the leaving group as W is a chlorine atom or a bromine atom, sodium iodide, potassium iodide or the like may be incorporated usually in an amount of about 0.1 to 10 mols, preferably in an amount of about 0.1 to 2 mols in relation to a compound represented by general formula (VIII) to accelerate the reaction.

The reaction is usually carried out in the presence of an appropriate base. As the base, for example, an organic amine (such as dimethylamine, diethylamine, diisopropylamine, trimethylamine, triethylamine, piperidine, piperazine, pyrrolidine, morpholine, pyridine, methanolamine or ethanolamine), a metal alkoxide (such as sodium methoxide, sodium ethoxide, lithium isopropoxide or potassium t-butoxide), an inorganic alkali metal salt (such as sodium hydroxide, potassium hydroxide, lithium hydroxide, potassium carbonate, sodium carbonate, sodium hydrogencarbonate, potassium hydrogencarbonate, sodium hydride, sodium acetate or potassium acetate) or an alkali metal amide (such as sodium amide) may be selected arbitrarily according to the probability of the reaction.

It is usually preferred to carry out the reaction in an appropriate solvent, and any solvent that does not adversely affect the reaction may be used arbitrarily as the solvent.

Process 3

A process for preparing a compound represented by general formula (I) wherein one of $X^1$ and $X^2$ is

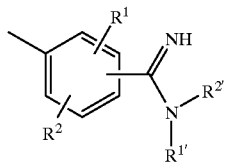

(wherein $R^{1'}$ and $R^{2'}$ are independently hydrogen atoms or $C_{1-6}$ alkyl groups, and $R^1$ and $R^2$ are the same as defined above) or

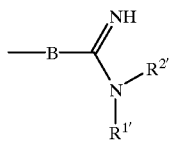

(wherein $R^{1'}$, $R^{2'}$ and B are the same as defined above), and the other of $X^1$ and $X^2$ is a $C_{1-6}$ alkyl group, a $C_{3-6}$ alkenyl group, an aryl $C_{1-4}$ alkyl group or an aryl group, which comprises reacting a compound represented by general formula (X):

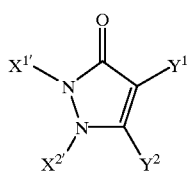

(X)

[wherein one of $X^{1'}$ and $X^{2'}$ is

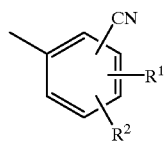

(wherein $R^1$ and $R^2$ are the same as defined above) or NC-B- (wherein B is the same as defined above), the other of $X^{1'}$ and $X^{2'}$ is a $C_{1-6}$ alkyl group, a $C_{3-6}$ alkenyl group, an aryl $C_{1-4}$ alkyl group or an alkyl group, and $Y^1$ and $Y^2$ are the same as defined above] with an amine represented by general formula (XI):

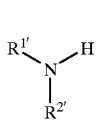

(XI)

(wherein $R^{1'}$ and $R^{2'}$ are the same as defined above) or an acid addition salt thereof.

The reaction is preferably carried out by known methods through several steps.

Namely, for example, a) a process comprising converting a nitrile represented by general formula (X) into a thioamide by using $H_2S$, converting the thioamide into the corresponding S-alkylimidothioester by using an alkylating reagent such as $CH_3I$ and then reacting the S-alkylimidothioester with an amine represented by general formula (X), b) a process comprising converting a nitrile represented by general formula (X) into the corresponding imide ester by using an alcohol (such as methanol or ethanol) in the presence of HCl and then reacting the imide ester with an amine represented by general formula (X), and c) a process comprising reacting a nitrile represented by general formula (X) with lithium (bistrimethylsilyl)amide and then hydrolyzing the product may be mentioned.

Process 4

A process for preparing a compound represented by general formula (I) wherein $Z^5$ is a carboxyl groups, which comprises hydrolysis, treatment with an acid, pyrrolysis or hydrogenolysis of a compound represented by general formula (XII):

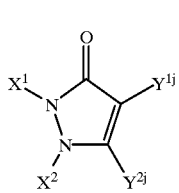

(XII)

[wherein $X^1$ and $X^2$ are the same as defined above, one of $Y^{1j}$ and $Y^{2j}$ is a D-E- group (wherein E is a bond, a $C_{1-4}$ alkylene group or a phenylene group (the phenylene group may be substituted with a halogen atom, a hydroxyl group, a $C_{1-4}$ alkyloxy group or a $C_{1-6}$ alkyl group), and D is a hydrogen atom, a $C_{1-6}$ alkyl group,

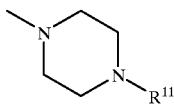

(wherein $R^{11}$ is a hydrogen atom, a $C_{1-6}$ alkyl group, a benzyl group or a formyl group), a pyridyl group or a phenyl group (the pyridyl and phenyl groups may be substituted with a halogen atom, a hydroxyl group, a $C_{1-4}$ alkyloxy group, a $R^3R^{3'}N$— group, a $R^3R^{3'}NCO$— group (wherein $R^3$ and $R^{3'}$ are the same as defined above) or a $C_{1-6}$ alkyl group)}, and the other of $Y^{1j}$ and $Y^{2j}$ is

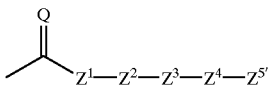

(wherein Q, $Z^1$, $Z^2$, $Z^3$ and $Z^4$ are the same as defined above, and $Z^{5'}$ is a group convertible to a carboxyl group such as a —$CO_2R'$ group (wherein R' is a methyl group, an ethyl group, a t-butyl group, a benzyl group or the like)].

The hydrolysis is carried out in the presence of an appropriate acid (such as hydrochloric acid, sulfuric acid, phosphoric acid, trichloroacetic acid or trifluoroacetic acid) or an appropriate base (such as sodium hydroxide or potassium hydroxide) in a solvent such as water, an alcohol (such as methanol, ethanol or propanol), an ether (such as tetrahydrofuran or dioxane) or a mixture thereof at a temperature of from −20° C. to 120° C., preferably from atmospheric temperature to the boiling point of the solvent. The t-butyl ester and the benzyl ester can be converted to carboxyl groups by treatment with an acid or pyrolysis, and by hydrogenolysis, respectively.

The present invention provides a medicinal composition containing an effective amount of a compound represented by general formula (I).

The mode of administration of compounds of the present invention may be parenteral administration of an injection (hypodermic, intravenous, intramuscular or intraperitoneal injection), an ointment, a suppository or an aerosol or oral administration of tablets, capsules, granules, pills, a syrup, a liquid, an emulsion or a suspension.

The pharmacological or veterinary composition containing a compound of the present invention contains the compound of the present invention in an amount of from about 0.01 to 99.5%, preferably from about 0.1 to 30%, based on the total weight of the composition.

In addition to the compound of the present invention, other pharmacological or veterinary active compound may be incorporated into the composition containing the compound. Such a composition may be contain more than one compound of the present invention.

The effective dosage of the compound of the present invention is usually from about 0.001 to 1.5 g, preferably from about 0.005 to 0.6 g per an adult per day, although its clinical dose depends on the age, weight, sensitivity and condition of the patient. However, if necessary, the dosage may be out of the above-mentioned range.

The compounds of the present invention may be formulated into various formulations suitable for administration in accordance with pharmaceutically conventional methods.

Namely, tablets, capsules, granules or pills for oral administration, may be prepared by using an excipient such as sugar, lactose, glucose, starch or mannitol; a binder such as hydroxypropylcellulose, syrup, gum arabic, gelatin, sorbitol, tragacanth gum, methylcellulose or polyvinylpyrrolidone; a disintegrant such as starch, carboxymethylcellulose or its calcium salt, microcrystalline cellulose or polyethylene glycol; a gloss agent such as talc, magnesium or calcium stearate or silica; or a lubricant such as sodium laurate or glycerol.

Injections, solutions, emulsions, suspensions, syrups or aerosols, may be prepared by using a solvent for the active ingredient such as water, ethyl alcohol, isopropyl alcohol, propylene glycol, 1,3-butylene glycol or polyethylene glycol; a surfactant such as a sorbitan fatty acid ester, a polyoxyethylene sorbitan fatty acid ester, a polyoxyethylene fatty acid ester, a polyoxyethylene ether of hydrogenated castor oil or lecithin; a suspending agent such as a cellulose derivative such as a sodium salt of carboxymethyl or methylcellulose, or a natural rubber such as tragacanth gum or gum arabic; or a preservative such as a paraoxybenzoic acid ester, benzalkonium chloride or a salt of sorbic acid.

Ointments for percutaneous absorption may be prepared by using white soft paraffin, liquid paraffin, a higher alcohol, macrogol ointment, hydrophilic ointment or an aqueous gel-type vehicle.

Suppositories may be prepared by using e.g. cacao butter, polyethylene glycol, lanolin, fatty acid triglyceride, coconut butter or polysorbate.

EXAMPLES

Now, the present invention will be described in further detail with reference to Examples (including Preparation Examples, Formulation Examples and Test Examples). However, it should be understood that the present invention is by no means restricted by these specific Examples.

The symbols "mp", "NMR" and "MS" indicate "melting point", "nuclear magnetic resonance spectrum" and "mass spectrum", respectively.

Preparation Examples

Reference Example 1

4-Cyanophenylhydrazine

To a mixture of 100 g of 4-aminobenzonitrile, 500 ml of water and 360 g of concentrated hydrochloric acid, a liquid mixture of 60.2 g of sodium nitrite and 240 ml of water was added at 0° C., and the resulting mixture was stirred for 30 minutes. The mixture was added to a liquid mixture of 382 g of stannous chloride dihydrate and 480 g of concentrated hydrochloric acid at 15° C., and the resulting crystals were collected by filtration, washed with water and then suspended in 1,000 ml of water. 300 ml of 5N aqueous sodium hydroxide was added to the suspension, and the resulting mixture was stirred for 1.5 hours. The resulting crude product was washed with water and recrystallized in benzene to give 70.2 g of the title compound as pale brown crystals.

mp 84–87° C., $^1$H-NMR(CDCl$_3$)δ: 3.60(2H,br s), 5.72 (1H,br s), 6.75(2H,d,J=9.0 Hz), 7.34(2H,d,J=9.0 Hz). Rf=0.27 (silica gel; benzene/ethyl acetate=3:1)

Reference Example 2

1-(4-Cyanophenyl)-2-methyl-hydrazine a) Preparation of (1-(4-Cyanophenyl)-2-methylhydrazino)triphenylphosphonium Bromide A mixture of 78.9 g of 4-cyanophenylhydrazine, 250 g of dibromotriphenylphosphorane, 71.9 g of triethylamine and 1,200 ml of benzene was stirred at 80° C for 30 minutes. The resulting crystals were collected by filtration and then washed with benzene and water successively to give 261.0 g of the title compound as a colorless powder.

b) 1-(4-Cyanophenyl)-2-methyl-hydrazine

To a mixture of 260 g of (1-(4-cyanophenyl)-2-methylhydrazino)triphenylphosphonium bromide and 2,000 ml of tetrahydrofuran, 347 ml of n-butyllithium (1.66 M, hexane solution) was added at 0° C., and the resulting mixture was stirred at room temperature for 1 hour. 85.6 g of methyl iodide was added thereto, and the resulting mixture was stirred for 20 hours. Then, 1,400 ml of 2N aqueous sodium hydroxide was added. The mixture was stirred at 50° C. for another 1 hour. After the mixture was allowed to separate, the aqueous layer was extracted with benzene. The organic layers were combined and extracted with 1N hydrochloric acid, and the extract was washed with chloroform. The resulting acidic aqueous solution was adjusted to pH 10–12 with 2N aqueous sodium hydroxide and then extracted with benzene. The extract was washed with saturated aqueous sodium chloride and dried over anhydrous sodium sulfate. After the insolubles were filtered off, the solvent was removed by evaporation under reduced pressure to leave 60.8 g of the title compound as a pale yellow liquid.

MS(EI)m/e: 147($M^+$), 132(100%), 117, 102. $^1$H-NMR (CDCl$_3$)δ: 2.63(3H,s), 3.59(1H,br s), 5.62(1H,br s), 6.87 (2H,d,J=9.0 Hz), 7.36(2H,d,J=9.0 Hz). Rf=0.43 (silica gel; benzene/ethyl acetate 3:1).

Reference Example 3

Diethyl 4-t-Butyl-benzoylmalonate

A mixture of 25.3 g of 4-t-butyl-benzoyl chloride, 30.9 g of diethyl malonate and 500 ml of tetrahydrofuran was stirred under cooling with ice and then stirred with 5.9 g of 55% sodium hydride for another 1 hour. To the reaction solution, 200 ml of aqueous ammonium chloride was added, and the tetrahydrofuran was removed by evaporation under reduced pressure. The residue was extracted with chloroform. The extract was dried over anhydrous sodium sulfate and concentrated under reduced pressure to give 36.2 g of the title compound as a pale yellow oily substance.

MS(EI)m/e: 320(M+), 275, 161(100%). $^1$H-NMR (CDCl$_3$)δ: 1.10(6H,t,J=7.1 Hz), 1.32(9H,s), 4.21(4H,q,J=7.1 Hz), 5.21(1H,s), 7.25(4H,s). Rf=0.49 (silica gel; hexane/ethyl acetate=5:1).

Reference Example 4

Ethyl 3-(4-t-Butylphenyl)-3-chloro-2-ethoxycarbonyl-acrylate

To a mixture of 72.5 g of diethyl 4-t-butyl-benzoylmalonate and 337.7 g of phosphorus oxychloride, 48.9 g of diisopropylethylamine was added, and the resulting mixture was stirred at 100° C. for 3 hours. The reaction mixture was evaporated under reduced pressure, and the resulting solid residue was extracted with diethyl ether, and the still remaining solid was mixed with water and then extracted diethyl ether. The extracts were combined, concentrated under reduced pressure, washed with 1N hydrochloric acid, 1N aqueous sodium hydroxide and water successively and dried over anhydrous sodium sulfate. The insoluble were filtered off, and the solvent was removed by evaporation. The resulting residue was purified by silica gel chromatography (eluent; n-hexane/ethyl acetate=7:1) to give 73.19 g of the title compound as a yellow oily substance.

MS(EI)m/e: 338($M^+$), 323(100%), 293. $^1$H-NMR(CDCl$_3$) δ: 0.98(6H,t,J=7.0 Hz), 1.32(9H,s), 1.34(3H,t,J=7.0 Hz), 3.98(2H,q,J=7.0 Hz), 4.39(2H,q,J=7.0 Hz), 7.37(4H,s). Rf=0.43 (silica gel; ethyl acetate/hexane 7:1).

Reference Example 5

3-(4-t-Butylphenyl)-1-(4-cyanophenyl)-4-ethoxycarbonyl-2-methyl-2H-pyrazol-5-one A mixture of 73.19 g of ethyl 3-(4-t-butylphenyl)-3-chloro-2-ethoxycarbonyl-acrylate, 33.6 g of 1-(4-cyanophenyl)-2-methyl-hydrazine, 44.3 g of diisopropyl-ethylamine and 500 ml of 1-propanol was refluxed under heating for 7 days. The reaction mixture was evaporated under reduced pressure. After addition of 1N hydrochloric acid, the resulting residue was extracted with chloroform. The extract was washed with 1N hydrochloric acid and saturated aqueous sodium chloride successively and dried over anhydrous sodium sulfate, and the solvent was removed by evaporation. The residue was recrystallized in ethyl acetate to give 34.9 g of the title compound as colorless crystals.

mp 202–204° C. MS(EI)m/e: 403($M^+$), 358, 330, 214, 158(100%), 115, 102. $^1$H-NMR(CDCl$_3$)δ: 1.19(3H,t,J=7.0 Hz), 1.37(9H,s), 3.09(3H,s), 4.21(2H,q,J=7.0 Hz), 7.40–7.90(8H,m). Rf=0.61 (silica gel; chloroform/methanol=10:1).

Reference Example 6

1-(4-Cyanophenyl)-4-ethoxycarbonyl-2-methyl-3-phenyl-2H-pyrazol-5-one 4.7 g of the title compound was prepared as colorless crystals from 14.6 g of ethyl 3-chloro-2-ethoxycarbonyl-3-phenyl-acrylate, 11.0 g of 1-(4-cyanophenyl)-2-methyl-hydrazine and toluene in the same manner as in Reference Example 5.

mp 218–220° C. MS(EI)m/e 347($M^+$), 318, 302, 275, 158, 129(100%), 102. $^1$H-NMR(CDCl$_3$)δ: 1.14(3H,t,J=8.6 Hz), 3.10(3H,s), 4.16(2H,q,J=8.6 Hz), 7.47–7.64(5H,m), 7.62 (2H,d,J=10.6 Hz), 7.79(2H,d,J=10.6 Hz). Rf=0.18 (silica gel; benzene/ethyl acetate=3:1).

Reference Example 7

2-(4-Cyanophenyl)-4-ethoxycarbonyl-1-methyl-3-phenyl-2H-pyrazol-5-one

A mixture of 9.0 g of ethyl 3-ethoxy-2-ethoxycarbonyl-3-phenyl-acrylate, 5.0 g of 1-(4-cyanophenyl)-2-methyl-hydrazine and 50 ml of toluene was refluxed under heating for 3 days. The mixture was allowed to cool to room temperature, and the resulting crystals were collected by filtration whereby 1.5 g of the title compound was obtained as colorless crystals.

mp 235–236° C. MS(EI)m/e 347($M^+$), 302, 274, 129, 102(100%). $^1$H-NMR(d-DMSO)δ: 0.95(3H,t,J=8.6 Hz), 3.11(3H,s), 3.97(2H,q,J=8.6 Hz), 7.29–7.42(5H,m), 7.56 (2H,d,J=10 Hz), 7.86(2H,d,J=10 Hz). Rf=0.76 (silica gel;chloroform/methanol=3:1).

Reference Example 8

1-(4-Cyanophenyl)-4-ethoxycarbonyl-2-methyl-3-[4-(4 -methylpiperazino)phenyl]-2H-pyrazol-5-one A liquid mixture of 872 mg of 1-(4-cyanophenyl)-4-ethoxycarbonyl-2-methyl-3-(4-fluorophenyl)-2H-pyrazol- 5-one and 2.39 g of N-methylpiperazine was heated at 100° C. for 36 hours with stirring. The reaction solution was cooled to room temperature, and 5 ml of ethyl acetate was added. The precipitated crystals were collected by filtration and dried under reduced pressure to give 519 mg of the title compound as pale yellow crystals.

mp 278–280° C. MS(m/e); 446(M+1)$^+$), 400(100%). [FAB] $^1$H-NMR(CDCl$_3$)δ: 1.27(3H,t,J=7.14 Hz), 2.37(3H, s), 2.56–2.60(4H,m), 3.09(3H,s), 3.35–3.38(4H,m), 4.25 (2H,q,J=7.14 Hz), 6.98(2H,d,J=9.06), 7.42(2H,d,J=9.06 Hz), 7.64(2H,d,J=8.78 Hz), 7.77(2H,d,J=8.88 Hz).

Reference Example 9

3-(4-t-Butylphenyl)-1-(4-cyanophenyl)-4-hydroxycarbonyl-2-methyl-2H-pyrazol-5-one A mixture of 34.5 g of 3-(4-t-butylphenyl)-1-(4-cyanophenyl)-4-ethoxycarbonyl-2-methyl-2H-pyrazol-5-one, 23.6 g of potassium carbonate, 621 ml of ethanol and 69 ml of water was refluxed under heating for 9 hours. The reaction solution was cooled to room temperature and adjusted to pH 1–2 with dilute hydrochloric acid. The resulting crystals were collected by filtration and dried under reduced pressure. The resulting crude crystals were recrystallized in methanol-ethyl acetate to give 12.2 g of the title compound as colorless crystals. The mother liquor was concentrated, and the resulting residue was crystallized in chloroform-diethyl ether to give 8.3 g of the title compound as pale yellow crystals.

Rf=0.53 (silica gel; chloroform/methanol=10:1).

Reference Example 10

3-(4-t-Butylphenyl)-4-chlorocarbonyl-1-(4-cyanophenyl)-2-methyl-2H-pyrazol-5-one A mixture of 12.1 g of 3-(4-t-butylphenyl)-1-(4-cyanophenyl)-4-hydroxycarbonyl-2-methyl-2H-pyrazol-5-one and 100 ml of thionyl chloride was stirred at room temperature for 1 hour. The reaction solution was concentrated under reduced pressure, and the residue was recrystallized in a liquid mixture of n-hexane-toluene to give 14.0 g of the title compound as pale yellow crystals.

mp 165–170° C.

Reference Example 11

1-t-Butoxycarbonyl-4-hydroxypiperidine

A mixture of 131 g of di-t-butyl dicarbonate and 500 ml of tetrahydrofuran was added dropwise to a mixture of 50 g of 4-hydroxypiperidine and 50 ml of water at room temperature over 1 hour, and the resulting mixture was stirred for 22.5 hours. The reaction solution was evaporated under reduced pressure, and after addition of water, the residue was extracted with chloroform. The organic layer was dried over sodium sulfate, and the insolubles were filtered off. The solvent was removed by evaporation. The resulting residue was crystallized in normal hexane:diethyl ether=1:1 to give 101 g of the title compound as colorless crystals.

mp 89–91° C. MS(EI)m/e: 201(M$^+$), 127, 100, 83, 57(100%), $^1$H-NMR(60 MHz, CDCl$_3$)δ: 1.45(9H,s), 1.2–2.0 (5H,m), 2.75–3.2(2H,m), 3.6–4.1(3H,m).

Reference Example 12

1-t-Butoxycarbonyl-4-ethoxycarbonylmethoxypiperidine

A mixture of 10.05 g of 1-t-butoxycarbonyl-4-hydroxypiperidine and 50 ml of tetrahydrofuran was stirred with 2.6 g of sodium hydride at room temperature for 30 minutes and then cooled to 0° C. A liquid mixture of 10.02 g of ethyl bromoacetate and 50 ml of tetrahydrofuran was added, and the reaction solution was stirred for 13.5 hours. After addition of saturated ammonium chloride, the reaction solution was extracted with chloroform. The extract was dried over anhydrous sodium sulfate, the insolubles were filtered off, and the solvent was removed by evaporation. The resulting residue was purified by silica gel column chromatography (eluent: ethyl acetate/normal hexane= 1:3→1:1) to give 6.28 g of the title compound as a pale yellow liquid.

MS(EI)m/e: 287(M$^+$), 214, 184, 84(100%) $^1$H-NMR(60 MHz, CDCl$_3$)δ: 1.45(9H,s), 1.5–2.0(4H,m), 2.75–4.0(5H, m), 4.08(2H,s), 4.19(2H,q,J=7.1 Hz).

Reference Example 13

Ethyl 4-Piperidinoxy Acetate

A liquid mixture of 10 g of 1-t-butoxycarbonyl-4-ethoxycarbonylmethoxypiperidine and 30 ml of saturated hydrochloric acid in ethanol was stirred at room temperature for 14 hours. The reaction solution was evaporated under reduced pressure to give 9.48 g of the title compound as a pale yellow oily substance.

MS(EI)m/e: 187(M$^+$), 100, 84(100%).

Example 1

3-(4-t-Butylphenyl)-4-{[4-(ethoxycarbonylmethyloxy)-1-piperidinyl] carbonyl}-1-(4-cyanophenyl)-2-methyl-2H-pyrazol-5-one (Compound No. 66)

A mixture of 3.5 g of 3-(4-t-butylphenyl)-4-chlorocarbonyl-1-(4-cyanophenyl)-2-methyl-2H-pyrazol-5-one, 1.8 g of triethylamine, 50 ml of tetrahydrofuran, 20 ml of N,N-dimethylformamide and 2.38 g of ethyl 4-piperidinoxyacetate was stirred at room temperature for 20 hours. The reaction solution was evaporated under reduced pressure, and after addition of water, the resulting residue was extracted with ethyl acetate. The organic layer was washed with saturated aqueous ammonium chloride and saturated aqueous sodium chloride successively and dried over sodium sulfate. The insolubles were filtered off, and then the solvent was removed by evaporation. The resulting residue was purified by silica gel chromatography (eluent; ethyl acetate/chloroform=1:1) to give 1.38 g of the title compound as a colorless amorphous solid.

MS(EI)m/e 544(M$^+$), 471, 441, 427, 358, 214, 186 (100%). $^1$H-NMR(CDCl$_3$)δ: 1.27(3H,t,J=7.4 Hz), 1.36(9H, s), 3.04(3H,s), 3.09(3H,s), 3.54–3.81(4H,m), 4.03(2H,br s), 4.17(2H,q,J=7.4 Hz), 7.47(4H,s), 7.68(4H,s). Rf=0.20 (silica gel; ethyl acetate/chloroform=1:1).

Example 2

1-(4-Amidinophenyl)-3-(4-t-butylphenyl)-4-{[4-(ethoxycarbonylmethyloxy)-1-piperidinyl] carbonyl}-2-methyl-2H-pyrazol-5-one monohydrochloride (Compound No. 29)

Dry hydrogen chloride was introduced into a mixture of 1.19 g of 3-(4-t-butylphenyl)-4-{[4-(ethoxycarbonylmethyloxy)-1-piperidinyl]carbonyl}-1-(4-cyanophenyl)-2-methyl-2H-pyrazol-5-one and 15 ml of absolute ethanol under cooling with ice for 2 hours, and the mixture was stirred under cooling with ice for another 15 hours. 38.5 g of ammonium carbonate was added to adjust the pH to 7–8, and the reaction solution was stirred at room temperature for 22 hours. The precipitated insolubles were filtered off, and hydrochloric acid in ethanol was added to the mother liquor to adjust the pH to 3. The precipitated crystals were filtered off, and the mother liquor was concentrated under reduced pressure. The residue was purified by C-18 reverse phase silica gel chromatography (water/methanol=2:1). The resulting crude crystals were recrystallized in methanol-chloroform-ethyl acetate to give 543 mg of the title compound as colorless crystals.

mp 265–267° C. MS(FAB)m/e: 562([M+1-HCl1+), 375 (100%). $^1$H-NMR(d-DMSO)a: 1.20(3H,t,J=7.1 Hz), 1.33 (9H,s), 1.71–1.81(4H,m), 3.05(3H,s), 3.55–3.80(4H,m), 4.11(2H,q,J=7.1 Hz), 4.12(2H,s), 4.12(2H,s), 7.54–7.62(4H, m), 7.83(2H,d,J=8.7 Hz), 8.01(2H,d,J=8.7), 9.52(3H,br s). Rf=0.37 (silica gel; chloroform/methanol/water/acetic acid= 10:4:1:0.5).

Example 3

1-(4-amidinophenyl)-3-(4-t-butylphenyl)-4-([4-(carboxymethyloxy)-1-piperidinyl]carbonyl}-2-methyl-2H-pyrazol-5-one hydrochloride (Compound No. 28)

A mixture of 100 mg of 1-(4-amidinophenyl)-3-(4-t-butylphenyl)-4-{[4-(ethoxycarbonylmethyloxy)-1-piperidinyl]carbonyl}-2-methyl-2H-pyrazol-5-one, 0.36 ml of 1N aqueous sodium hydroxide and 0.72 ml of ethanol was stirred at room temperature for 1 hour, and the reaction solution was adjusted to pH 3 with dilute hydrochloric acid. The solvent was removed by evaporation under reduced pressure. The resulting residue was recrystallized in water to give 70.7 mg of the title compound as colorless crystals.

mp 247–252° C. MS(EI)m/e 516([M-HCl—OH]$^+$, [M-HCl—NH$_3$]$^+$), 441, 358, 158. $^1$H-NMR(CD$_3$CO$_2$D)δ: 1.19–1.87(4H,m), 1.39(9H,s), 3.30(3H,s), 3.32–3.76(4H,m), 3.94–4.03(1H,m), 4.19(2H,s), 7.59(2H,d,J=8.4 Hz), 7.65 (2H,d,J=8.4 Hz), 7.87(2H,d,J=8.8 Hz), 8.11(2H,d,J=8.8 Hz). Rf=0.57 (silica gel; chloroform/methanol/water/acetic acid= 10:6:2:1).

Reference Example 14

Diethyl 4-iodobenzoyl-malonate

To a mixture of 41.8 g of diethyl malonate and 100 ml of tetrahydrofuran, 11.0 g of 60% sodium hydride was added, and the resulting mixture was stirred at room temperature for 1 hour. The mixture was added gradually dropwise to a mixture of 69.5 g of 4-iodobenzoyl chloride and 300 ml of tetrahydrofuran under cooling with dry ice-acetone. The reaction mixture was stirred for 3 hours, and then 300 ml of water was added. The tetrahydrofuran was removed from the reaction mixture by evaporation under reduced pressure, and the reaction mixture was extracted with diethyl ether. The extract was dried over magnesium sulfate, filtered and concentrated at atmospheric pressure. The resulting residue was recrystallized in diethyl ether-hexane to give 28.5 g of the title compound as colorless crystals.

MS(EI)m/e: 390(5%, M$^+$), 231(100%), 203(14%) $^1$H-NMR(CDCl$_3$)δ: 1.25(t,6H,J=7 Hz), 4.23(q,4H,J=7 Hz), 5.16(s,1H), 7.55(d,2H,J=8 Hz), 7.77(d,2H,J=8 Hz).

Reference Example 15

Ethyl 3-(4-iodophenyl)-3-chloro-2-ethoxycarbonylacrylate

A mixture of 28.3 g of diethyl 4-iodobenzoylmalonate, 14.6 g of diisopropylethylamine and 20 ml of phosphorus oxychloride was stirred at 100° C. for 2 hours and then poured over ice. The reaction mixture was extracted with diethyl ether, and the extract was dried over magnesium sulfate, treated with activated carbon, filtered and then concentrated at atmospheric pressure. The resulting residue was purified by silica gel column chromatography (hexane:ethyl acetate=10:1) to give 20.14 g of the title compound as a pale yellow liquid.

MS(EI)m/e: 408(44%, M$^+$), 363(26%), 255(37%), 231 (37%), 128(100%), $^1$H-NMR(CDCl$_3$)δ: 1.07(t,3H,J=7 Hz), 1.35(t,3H,J=7 Hz), 4.03(q,2H,J=7 Hz), 4.33(q,2H,J=7 Hz), 7.02(d,2H,J=8 Hz), 7.64(d,2H,J=8 Hz).

Reference Example 16

3-(4-Iodophenyl)-1-(4-cyanophenyl)-4-ethoxycarbonyl-2-methyl-2H-pyrazol-5-one

A mixture of 29.34 g of 1-(4-cyanophenyl)-2-methylhydrazine, 65.17 g of ethyl 3-(4-iodophenyl)-3-chloro-2-ethoxycarbonylacrylate, 30.9 g of diisopropylethylamine and 300 ml of 1-propanol was refluxed under heating for 17 hours, then cooled and stirred with 200 ml of ethyl acetate at room temperature for 20 hours. The precipitated crystals were collected by filtration and washed with hexane-ethyl acetate to give 42.21 g of the title compound as pale yellow crystals.

MS(EI)m/e: 473(20%, M$^+$), 428(21%), 401(7%), 284 (47%), 184(100%), $^1$H-NMR(CDCl$_3$)δ: 1.19(t,3H,J=7 Hz), 3.07(s,3H), 4.17(q,2H,J=7 Hz), 7.21(d,2H,J=8 Hz), 7.59(d, 2H,J=8 Hz), 7.68(d,2H,J=8 Hz), 7.82(d,2H,J=8 Hz)

Reference Example 17

1-(4-Cyanophenyl)-4-ethoxycarbonyl-2-methyl-3-{4-(2-pyridyl)phenyl}-2H-pyrazol-5-one A mixture of 1.06 g of lithium, 20 g of naphthalene and 100 ml of tetrahydrofuran was stirred in a stream of argon at room temperature for 2.5 hours. 150 ml of 0.5M zinc chloride-tetrahydrofuran solution was added over 30 minutes, and the reaction solution was stirred for another 1 hour to give a black precipitate. The black precipitate was washed with tetrahydrofuran, and 6.7 g of 2-bromopyridine and 100 ml of tetrahydrofuran were added. The reaction solution was stirred at room temperature for 14.5 hours and then allowed to stand. The resulting orange supernatant, 3.0 g of 1-(4-cyanophenyl)-4-ethoxycarbonyl-3-(4-iodophenyl)-2-methyl-2H-pyrazol-5-one and 500 mg of tetrakistriphenylphosphinepalladium were mixed and stirred in a stream of argon at room temperature for 3.5 hours. The solvent was removed by evaporation under reduced pressure, and after addition of water, the reaction solution was extracted with chloroform. The extract was dried over magnesium sulfate, and the insolubles were filtered off. The solvent was removed by evaporation under reduced pressure. The resulting residue was purified by silica gel chromatography (eluent: ethyl acetate) to give 2.64 g of the title compound as a pale orange crystalline powder.

mp 205–211° C. (DEC.), MS(EI)m/e: 424(M$^+$), 379, 352, 235, 206, 83(100%) $^1$H-NMR(400 MHz, CDCl$_3$)δ: 1.01(3H, t,J=7.1 Hz), 3.37(3H,s), 4.02(2H,q,J=7.1 Hz), 7.44(1H,dd, J=4.6, 6.6 Hz), 7.77(2H,d,J=8.4 Hz), 7.79(2H,d,J=8.8 Hz), 7.96(1H,m), 8.07(2H,d,J=8.8 Hz), 8.12(1H,d,J=8.1 Hz), 8.29(2H,d,J=8.4 Hz), 8.74(1H,d,J=4.6 Hz).

Reference Example 18

1-(4-Cyanophenyl)-4-hydroxycarbonyl-2-methyl-3-[4-(2-pyridyl)phenyl]-2H-pyrazol-5-one A mixture of 2.7 g of 1-(4-cyanophenyl)-4-ethoxycarbonyl-2-methyl-3-[4-(2-pyridyl)phenyl]-2H- pyrazol-5-one, 1.8 g of potassium carbonate, 73 ml of ethanol and 8 ml of water was refluxed under heating for 9 hours. The reaction solution was cooled to room temperature, and the precipitated crystals were collected by filtration and dried under reduced pressure. The resulting crude crystals were suspended in chloroform, and the suspension was adjusted to pH 2 to 3 with dilute hydrochloric acid. The crystals were collected by filtration and dried under reduced pressure to give 1.6 g of the title compound as pale gray crystals.

mp 155–166° C. $^1$H-NMR(CDCl$_3$)δ: 3.30(3H,s), 7.21–7.29(1H,m), 7.66(2H,d,J=7.51 Hz), 7.74–7.89(6H,m), 8.19(2H,d,J=7.51 hz), 8.70–8.74(1H,m), 12.0–14.0(1H,br s) MS(FAB)m/e 397(M+1), 379.

Example 4

4-{[4-(Carboxymethyloxy)-1-piperidinyl]carbonyl}-1-(4-cyanophenyl)-2-methyl-3-[4-(2-pyridyl)phenyl]-2H-pyrazol-5-one (Compound No. 149)

a) Preparation of 1-(4-Cyanophenyl)-4-chlorocarbonyl-2-methyl-3-[4-(2-pyridyl)phenyl]-2H-pyrazol-5-one A mixture of 1.6 g of 1-(4-cyanophenyl)-4-hydroxycarbonyl-2-methyl-3-[4-(2-pyridyl)phenyl]-2H-pyrazol-5-one and 16 ml of thionyl chloride was stirred at room temperature for 3 hours. The reaction solution was concentrated under reduced pressure, and the residue was crystallized in a liquid mixture of n-hexane-toluene to give 1.65 g of the desired compound as a pale yellow solid.

b) Preparation of 4-{[4-(Carboxymethyloxy)-1-piperidinyl]carbonyl}-1-(4-cyanophenyl)-2-methyl-3-[4-(2-pyridyl)phenyl]-2H-pyrazol-5-one A mixture of 1.62 g of 1-(4-cyanophenyl)-4-chlorocarbonyl-2-methyl-3-[4-(2-pyridyl)phenyl]-2H-pyrazol-5-one, 2.04 g of triethylamine, 20 ml of tetrahydrofuran and 1.35 g of ethyl 4-piperidinoxyacetate was stirred at room temperature for 16 hours. The reaction solution was evaporated under reduced pressure, and the resulting residue was extracted with chloroform. The organic layer was washed with saturated aqueous sodium chloride and dried over sodium sulfate. The insolubles were filtered off, and the solvent was removed by evaporation. The resulting residue was crystallized in chloroform-methanol-ethyl acetate to give 250 mg of the title compound as pale yellow crystals. The mother liquor was evaporated under reduced pressure, and the resulting residue was purified by silica gel chromatography (eluent;ethyl acetate:methanol 9:1). The resulting crude crystals were recrystallized in chloroform-methanol-ethyl acetate to give 601 mg of the title compound as pale pink crystals.

mp 156–159° C. MS(FAB)m/e 556(M+1, 100%), 379, Rf=0.51 (silica gel; ethyl acetate/methanol=9:1), $^1$H-NMR (CDCl$_3$)δ: 1.27(3H,t,J=7.1 Hz), 1.58(1H,m), 1.69(1H,m), 1.77(1H,m), 1.87(1H,m), 3.09(3H,s), 3.34(1H,m), 3.57(1H, m), 3.63(1H,m), 3.69(1H,m), 3.92(1H,m), 4.08(2H,d,J=0.9 Hz), 4.19(2H,q,J=7.1 Hz), 7.32(1H,m), 7.68(2H,d,J=8.4 Hz), 7.71(2H,d,J=8.8 Hz), 7.79(2H,d,J=8.8 Hz), 7.80(1H, m), 7.83(1H,m), 8.15(2H,d,J=8.4 Hz), 8.74(1H,m).

Example 5

1-(4-Amidinophenyl)-4-{[4-(carboxymethyloxy)-1-piperidinyl]carbonyl}-2-methyl-3-[4-(2-pyridyl)phenyl]-2H-pyrazol-5-one monohydrochloride (Compound No. 132)

Dry hydrogen chloride was introduced into a mixture of 3.83 g of 4-{[4-(carboxymethyloxy)-1-piperidinyl]carbonyl}-1-(4-cyanophenyl)-2-methyl-3-[4-(2-pyridyl)phenyl]-2H-pyrazol-5-one and 38 mg of absolute ethanol under cooling with ice for 40 minutes, and then the mixture was stirred at room temperature for another 3.5 hours. The reaction solution was evaporated under reduced pressure, and 15 ml of absolute ethanol and 6.44 g of ammonium carbonate were added to the resulting crude crystals to adjust the pH to 7–8. The resulting reaction solution was stirred at room temperature for 13 hours and at 50° C. for 1 hour. The reaction solution was concentrated under reduced pressure, and the resulting residue was stirred with dilute hydrochloric acid at room temperature for 10 minutes. The resulting reaction solution was concentrated under reduced pressure, and the resulting residue was purified by C-18 reverse phase silica gel chromatography (eluent;water→water:methanol= 4:1). The resulting crude crystals were recrystallized in ethanol-ethyl acetate to give 3.1 g of the title compound as yellow crystals.

mp 205–232° C. (DEC.), MS(FAB)m/e 583(M+l, 100%), 396, 1H-NMR(d-DMSO)δ: 1.19(3H,t,J=7.14 Hz), 1.35–1.88(4H,m), 3.12(3H,s), 3.14–3.93(4H,m), 3.58–3.63 (1H,m), 4.09(2H,q,J=7.14 Hz), 4.14(2H,s), 7.42–7.46(1H, m), 7.76(2H,d,J=8.60 Hz), 7.88(2H,d,J=8.60 Hz), 7.93–7.98 (1H,m), 8.02(2H,d,J=8.79 Hz), 8.10–8.13(1H, m), 8.31(2H, d,J=8.60 Hz), 8.72–8.74(1H,m), 9.16(2H,br s), 9.45(2H,br s).

Example 6

1-(4-Amidinophenyl)-4-{[4-(carboxymethyloxy)-1-piperidinyl]carbonyl}-2-methyl-3-[4-(2-pyridyl)phenyl]-2H-pyrazol-5-one A mixture of 3.0 g of 1-(4-amidinophenyl)-4-{[4-(carboxymethyloxy)-1-piperidinyl]carbonyl}-2-methyl-3-[4-(2-pyridyl)phenyl]-2H-pyrazol-5-one, 20.6 ml of 1N aqueous sodium hydroxide and 10 ml of water was stirred at room temperature for 4 hours and then stirred with 20.6 ml of 1N aqueous sodium hydroxide and 20 ml of water at room temperature for 20 hours. The reaction solution was adjusted to pH 3 with dilute hydrochloric acid and purified by C-18 reverse phase silica gel chromatography (eluent;water→water:methanol=4:1→2:1). The resulting crude crystals were washed with ethanol to give 1.56 g of the title compound as colorless crystals.

mp 238–249° C., MS(FAB)m/e 577(M+Na), 555(M+l, 100%), 538, $^1$H-NMR(d-DMSO)δ: 1.35–1.88(4H,m), 3.12 (3H,s), 3.18–3.95(4H,m), 3.60–3.68(1H,m), 3.93(2H,s), 7.42–7.46(1H,m), 7.76(2H,d,J=8.42 Hz), 7.87(2H,d,J=8.60 Hz), 7.92–7.98(1H,m), 8.06(2H,d,J=8.79 Hz), 8.08–8.13 (1H,m), 8.31(2H,d,J=8.42 Hz), 8.72–8.74(1H,m), 9.12(2H, br s), 10.9–12.8(1H,br s).

Example 6'

1-(4-Amidinophenyl)-4-([4-(carboxymethyloxy)-1-piperidinyl]carbonyl}-2-methyl-3-[4-(2-pyridyl)phenyl]-2H-pyrazol-5-one dihydrochloride (Compound No. 131)

5 ml of concentrated hydrochloric acid was added to a mixture of 100 ml of water and 5.25 g of 1-(4-amidinophenyl)-4-{[4-(carboxymethyloxy)-1-piperidinyl]carbonyl}-2-methyl-3-[4-(2-pyridyl)phenyl]-2H-pyrazol-5-one to make a solution. The solution was stirred with 1200 ml of acetonitrile for 15 hours, and the precipitated crystals were collected by filtration. The crystals were dried at 60° C.

under reduced pressure to give 5.55 g of the title compound as pale yellow crystals.

mp 235–245° C. (DEC.).

Reference Example 19

3-(4-t-butylphenyl)-1-(4-cyanophenyl)-4-(N-hydroxyethyl-N-methyl-aminocarbonyl)-2-methyl-2H-pyrazol-5-one To a liquid mixture of 150 mg of 3-(4-t-butylphenyl)-4-chlorocarbonyl-1-(4-cyanophenyl)-2-methyl-2H-pyrazol-5-one and 3 ml of tetrahydrofuran, 72 mg of N-methylethanolamine was added at room temperature, and the resulting mixture was stirred at the same temperature for another 1 hour and then concentrated under reduced pressure. After addition of 1N hydrochloric acid, the mixture was extracted with chloroform. The extract was washed with 1N hydrochloric acid and saturated aqueous sodium chloride successively and dried over anhydrous sodium sulfate. The insolubles were filtered off, and the filtrate was concentrated under reduced pressure. The resulting residue was recrystallized in ethyl acetate-hexane to give 110 mg of the title compound as colorless crystals.

mp 210–213° C., MS(EI)m/e: 432(M$^+$), 402, 358(100%), 270, 214, 158, 116. $^1$H-NMR(CDCl$_3$)δ: 1.32(9H,s), 3.05 (6H,s), 3.51–3.90(5H,m), 7.43(4H,s), 7.65(4H,s). Rf=0.24 (silica gel;ethyl acetate/methanol=20:1).

Example 7

4-(N-t-butyloxycarbonylmethyloxyethyl-N-methylaminocarbonyl)-3-(4-t-butylphenyl)-1-(4-cyanophenyl)-2-methyl-2H-pyrazol-5-one (Compound No. 49)

To a mixture of 200 mg of 3-(4-t-butylphenyl)-1-(4-cyanophenyl)-4-(N-hydroxyethyl-N-methyl-aminocarbonyl)-2-methyl-2H-pyrazol-5-one, 4 ml of tetrahydrofuran and 108 mg of t-butyl bromoacetate, 12.2 mg of sodium hydride was added at 0° C., and the resulting reaction solution was refluxed under heating for 3 days. After the reaction solution was cooled to room temperature, saturated aqueous ammonium chloride was added, and the reaction solution was extracted with chloroform. The extract was washed with 1N hydrochloric acid and saturated aqueous sodium chloride successively and dried over anhydrous sodium sulfate. The insolubles were filtered off, and the filtrate was concentrated. The resulting residue was recrystallized in chloroform-ether-hexane to give 100 mg of the title compound as colorless crystals.

mp 218–222° C. MS(EI)m/e: 546(M$^+$), 489, 415, 387, 358(100%). $^1$H-NMR(CDCl$_3$)δ: 1.44(9H,s), 2.75(1H,br s), 3.35(3H,s), 3.42–3.76(4H,m), 3.93(2H,s), 7.41(2H,d,J=9.0 Hz), 7.73(2H,d,J=9.0 Hz), 8.12(1H,s). Rf=0.59(silica gel; ethyl acetate).

Example 8

3-(4-t-butylphenyl)-1-(4-cyanophenyl)-4-(N-ethoxycarbonylmethyloxyethyl-N-methyl-aminocarbonyl)-2-methyl-2H-pyrazol-5-one (Compound No. 65)

To a mixture of 900 mg of 4-(N-t-butyloxycarbonylmethyloxyethyl-N-methyl-aminocarbonyl)-3-(4-t-butylphenyl)-1-(4-cyanophenyl)-2-methyl-2H-pyrazol-5-one and 10 ml of ethanol, 4 drops of concentrated sulfuric acid was added, and the resulting reaction solution was refluxed under heating for 2.5 hours. After the ethanol was removed by evaporation under reduced pressure, water was added, and the reaction solution was extracted with chloroform. The extract was washed with saturated aqueous sodium chloride and dried over anhydrous sodium sulfate. The insolubles were filtered off, and the filtrate was concentrated. The resulting residue was recrystallized in chloroform-ether-hexane to give 440 mg of the title compound as colorless crystals.

mp 192–194° C. MS(EI)m/e: 518(M$^+$), 414, 386, 358 (100%). $^1$H-NMR(CDCl$_3$)δ: 1.27(3H,t,J=7.4 Hz), 1.36(9H, s), 3.04(3H,s), 3.09(3H,s), 3.54–3.81(4H,m), 4.03(2H,br s), 4.17(2H,q,J=7.4 Hz), 7.47(4H,s), 7.68(4H,s). Rf=0.50 (silica gel; ethyl acetate).

The instrumental data for the compound prepared in accordance with the above Examples are tabulated in Table II and Table III.

The compound Nos. in Table I should be referred to for the structures of the compounds.

TABLE II

| Compound No. | mp (° C.) | MS (m/e) |
|---|---|---|
| 1 | 283–290 | 362([M+1-HCl]$^+$). (FAB) |
| 2 | 214–219 | 616([M+1-HCl]$^+$, 100%), 429. (FAB) |
| 3 | Amorphous solid | |
| 4 | 202–250 | 375([M-HCl]$^+$), 360, 316, 243, 226(100%). (EI) |
| 5 | Amorphous solid | 404([M+1-HCl]$^+$). (FAB) |
| 6 | Amorphous solid | 417([M-HCl]$^+$), 358, 226(100%). (EI) |
| 7 | 284–288 (dec.) | 358([M-HCl—OH]$^+$, [M-HCl—NH$_3$]$^+$), 299, 243, 226(100%). (EI) 376([M+1-HCl]$^+$). (FAB) |
| 8 | 227–233 | 402([M+1-HCl]$^+$). (FAB) |
| 9 | Amorphous solid | 429([M-HCl]$^+$), 412, 243, 226. (EI) |
| 10 | 257–259 | 384([M-HCl—OH]$^+$, [M-HCl—NH$_3$]$^+$), 243, 226. (EI) 402([M+1-HCl]$^+$). (FAB) |
| 11 | Amorphous solid | 429([M-HCl]$^+$), 412, 243, 226. (EI) |
| 12 | 274–280 | 420([M-HCl—OH]$^+$, [M-HCl—NH$_3$]$^+$), 361, 345, 331, 319, 302(100%). (EI) |
| 13 | Amorphous solid | 466([M+1-HCl]$^+$). (FAB) |
| 14 | 259–264 | 451([M-HCl]$^+$), 434, 319, 302(100%), 214. (EI) |
| 15 | Amorphous solid | 479([M-HCl]$^+$), 450, 434, 406, 333, 319, 302(100%), 214. (EI) |
| 16 | 272–275 | 480([M+1-HCl]$^+$). (FAB) |
| 17 | 253–260 | 500([M+Na-HCl]$^+$), 478([M+1-HCl]$^+$), 319(100%). (FAB) |
| 19 | 307–323 (dec.) | 514([M+1-HCl]$^+$). (FAB) |

TABLE II-continued

| Compound No. | mp (° C.) | MS (m/e) |
|---|---|---|
| 20 | 235–237 | 542([M+1-HCl]$^+$). (FAB) |
| 21 | Amorphous solid | 542([M+1-HCl]$^+$). (FAB) |
| 22 | 238–250 (dec.) | 536([M-HCl—OH]$^+$, [M-HCl—NH$_3$]$^+$), 508, 461, 378. (EI) |
|  |  | 554([M+1-HCl]$^+$), 395. (FAB) |
| 23 | Amorphous solid | 604([M+Na-HCl]$^+$), 582([M+1-HCl]$^+$), 395(100%). (FAB) |
| 24 | 225–231 | 476([M-HCl—OH]$^+$, [M-HCl—NH$_3$]$^+$), 417, 401, 387, 358(100%). (EI) |
|  |  | 516([M+Na-HCl]$^+$), 494([M+1-HCl]$^+$), 375(100%). (FAB) |
| 25 | 223–228 | 521([M-HCl]$^+$), 505, 504, 492, 476, 475, 434, 418, 401, 375, 358(100%). (EI) |
| 26 | 194–209 (dec.) | 490([M-HCl—OH]$^+$, (M-HCl—NH$_3$]$^+$), 415, 375, |
|  |  | 358(100%), 132. (EI) |
|  |  | 530([M+Na-HCl]$^+$), 508([M+1-HCl]$^+$), 375(100%). (FAB) |
| 27 | 190–196 (dec.) | 521([M-HCl]$^+$), 506, 415, 387, 358(100%). (EI) |
| 28 | 247–252 | 516([M-HCl—OH]$^+$, [M-HCl—NH$_3$]$^+$), 441, 358, 158. (EI) |
|  |  | 534([M+1-HCl]$^+$), 375(100%). (FAB) |
| 29 | 265–267 | 562([M+1-HCl]$^+$), 375(100%). (FAB) |
| 30 | 198–213 (dec.) | 547([M-HCl]$^+$), 485, 471, 455, 441, 429, 412(100%). (EI) |
| 31 | 197–202 (dec.) | 546([M-HCl-Et]$^+$), 502, 488, 472, 458, 444, 429, 412(100%). (EI) |
| 33 | 252–255 | 587([M-HCl]$^+$), 570, 512, 495, 429, 412(100%). (EI) |
| 34 | 230 (dec.) | 529([M-HCl—NH$_3$]$^+$), 456, 375, 358(100%). (EI) |
|  |  | 547([M+1-HCl]$^+$), 375(100%). (FAB) |
| 35 | 197–222 | 451, 435, 421, 407, 378(100%). (EI) |
|  |  | 578([M+Na—HCl]$^+$), 556([M+1-HCl]$^+$), 395(100%). (FAB) |
| 36 | 247–251 | 612([M+Na-HCl]$^+$), 590([M+1-HCl]$^+$), 429. (FAB) |
| 37 | 233 (dec.) | 501([M-HCl—OH]$^+$, [M-HCl—NH$_3$]$^+$), 459, 456, |
|  |  | 400, 375, 358(100%). (EI) |
|  |  | 519([M+1-HCl]$^+$), 375(100%). (FAB) |
| 38 | 313–314 | 528([M+1-HCl]$^+$). (FD) |
| 39 | 306–312 | 562([M+1-HCl]$^+$), 429. (FAB) |
| 40 | Amorphous solid | 561([M+1-HCl]$^+$), 375(100%). (FAB) |
| 41 | 247–254 (dec.) | 538([M+1-HCl]$^+$), 521, 504, 476, 420, 395, 378(100%). (EI) |
| 42 | 196 (dec.) | 567([M+1-HCl]$^+$), 395(100%). (FAB) |
| 43 | 247–275 (dec.) | 528([M+1-HCl]$^+$). (FD) |
| 45 | 263–268 | 581([M+1-HCl]$^+$, 100%), 395. (FAB) |
| 46 | 243–261 | 533([M+1-HCl]$^+$, 100%), 395. (FAB) |
| 47 | 265–272 | 533([M+1-HCl]$^+$, 100%), 395. (FAB) |
| 48 | Amorphous solid | 400(M$^+$), 327, 229, 268, 226(100%), 102. (EI) |
| 49 | 218–222 | 546(M$^+$), 489, 415, 387, 358(100%). (EI) |
| 53 | Amorphous solid | 358(M$^+$), 226(100%). (EI) |
| 55 | Oily substance | 400(M$^+$), 385, 369, 341, 311, 297, 283, 226(100%), 174. (EI) |
| 56 | Oily substance | 412(M$^+$), 226, 186, 130, 116, 102(100%). (EI) |
| 57 | Oily substance | 412(M$^+$), 383, 367, 309, 295, 226, 198, 186, 130, 116, 102(100%). (EI) |
| 58 | Oily substance | 448(M$^+$), 403, 375, 361, 317, 302(100%). (EI) |
| 59 | Amorphous solid | 462(M$^+$), 359, 331, 302(100%), 158. (EI) |
| 60 | Oily substance | 488(M$^+$-HCl), 415, 385, 302, 158(100%). (EI) |
| 61 | Amorphous solid | 525([M+1]$^+$), 378(100%). (FAB) |
| 62 | Amorphous solid | 538(M$^+$), 493, 451, 435, 421, 378(100%), 160. (EI) |
| 63 | 179–183 | 564(M$^+$), 378(100%). (EI) |
| 64 | Amorphous solid | 504(M$^+$), 459, 431, 417, 401, 373, 358 (100%). (EI) |
| 65 | 192–194 | 518(M$^+$), 414, 386, 358(100%). (EI) |
| 66 | Amorphous solid | 544(M$^+$), 471, 441, 427, 358, 214, 186 (100%). (EI) |
| 67 | Amorphous solid | 581([M+Na]$^+$), 559([M+1]$^+$), 412(100%). (FAB) |
| 68 | Amorphous solid | 621([M+Na]$^+$), 599([M+1]$^+$), 412(100%). (FAB) |
| 109 | 247–275 (dec.) | 533([M+1-2HCl]$^+$), 375(100%). (FAB) |
| 110 | Solid | 561([M+1-2HCl]$^+$), 375(100%). (FAB) |
| 111 | 220–257 (dec.) | 547([M+1-2HCl]$^+$), 375(100%). (FAB) |
| 112 | 239–250 (dec.) | 575([M+1-2HCl]$^+$), 375(100%). (FAB) |
| 113 | 255–260 (dec.) | 561([M+1-HCl]$^+$), 375(100%). (FAB) |
| 114 | 226–253 (dec.) | 589([M+1-HCl]$^+$), 375(100%). (FAB) |
| 115 | 254–264 |  |
| 116 | 213–218 | 575([M+1-2HCl]$^+$), 375(100%). (FAB) |
| 117 | 224–237 (dec.) | 533([M+1-2HCl]$^+$), 375(100%). (FAB) |
| 118 | 216–229 (dec.) | 561([M+1-2HCl]$^+$), 375(100%). (FAB) |
| 119 | 249–257 (dec.) | 575([M+1-HCl]$^+$), 375(100%). (FAB) |
| 120 | 259–265 (dec.) | 603([M+1-HCl]$^+$), 375(100%). (FAB) |
| 121 | 251–258 (dec.) | 637([M+1-HCl]$^+$), 375(100%). (FAB) |
| 122 | 224–244 (dec.) | 665([M+1-HCl]$^+$), 375(100%). (FAB) |
| 123 | 252–265 (dec.) | 638([M+1-HCl]$^+$), 375(100%). (FAB) |
| 124 | 199–248 (dec.) | 666([M+1-HCl]$^+$), 375(100%). (FAB) |
| 125 | 220 (dec) | 533([M+1-2HCl]$^+$), 507, 375. (FAB) |
| 126 | Solid | 581([M+1-2HCl]$^+$), 395(100%). (FAB) |
| 127 | 276–278 | 534([M+1-HCl]$^+$), 375(100%). (FAB) |
| 128 | 182–191 (dec.) | 561([M+1-HCl]$^+$), 375(100%). (FAB) |
| 129 | 246–251 (dec.) | 603([M+1-HCl]$^+$), 445. (FAB) |
| 130 | 222–227 (dec.) | 632([M+1-HCl]$^+$, 100%), 445. (FAB) |
| 131 | 235–246 (dec.) |  |
| 132 | 205–232 (dec.) | 583([M+1-HCl]$^+$, 100%), 396. (FAB) |
| 133 | 249–261 (dec.) | 576([M+1-2HCl]$^+$, 100%). (FD) |

TABLE II-continued

| Compound No. | mp (° C.) | MS (m/e) |
|---|---|---|
| 134 | 200 (dec.) | 604([M+1-2HCl]+), 417(100%). (FAB) |
| 135 | 230–248 (dec.) | 590([M+1-2HCl]+, 100%). (FD) |
| 136 | 200–207 | 618([M+1-2HCl]+), 431. (FAB) |
| 137 | 275–279 | 584([M+1-2HCl]+, 100%). (FD) |
| 138 | 260–272( dec.) | |
| 139 | Amorphous solid | |
| 140 | 196–199 | 557(M+), 528, 484, 358, 199, 96(100%). (EI) |
| 141 | 223–224 | 571(M+), 484, 358, 213, 82(100%). (EI) |
| 142 | 146–149 | 557(M+), 484, 470, 358, 199, 156(100%). (EI) |
| 143 | 204–208 (dec.) | 585(M+), 468, 440, 82(100%). (EI) |
| 144 | 224–226 | 647(M+), 440, 358, 82(100%). (EI) |
| 145 | 252–257 (dec.) | 648(M+), 561, 440, 358, 82(100%). (EI) |
| 146 | 176–178 | 563(M+), 517, 490, 378(100%). (EI) |
| 147 | 146–148 | 545(M+), 358, 214, 82(100%). (EI) |
| 148 | 201–203 | 614(M+), 511, 497, 428, 186, 82(100%). (EI) |
| 149 | 156–159 | 565(M+), 448, 379, 186, 82(100%). (EI) |
| 150 | 191–193 | |
| 151 | 211–213 | 600(M+), 497, 414, 186, 82(100%). (EI) |
| 152 | 234–239 (dec.) | 589(M+), 486, 472, 403, 186, 82(100%). (EI) |
| 153 | 218–225 (dec.) | 561([M+1-HCl]+), 375(100%). (FAB) |
| 154 | 189–203 | 589([M+1-HCl]+), 375(100%). (FAB) |
| 155 | 173–174 | |

TABLE III

| No. | | $^1$H-NMR |
|---|---|---|
| 1 | (D$_2$O) | δ: 3.42(3H, s), 3.40–3.47(2H, m), 3.50–3.58(2H, m), 4.65(2H, s), 7.54(2H, d, J=8.3 Hz), 7.87(2H, d, J=8.3 Hz), 8.14(1H, s). |
| 2 | (CD$_3$OD) | δ: 1.25(3H, t, J=7.1 Hz), 1.47–1.92(4H, m), 3.23(3H, s), 3.40–3.97(5H, m), 4.14(2H, s), 4.17(2H, q, J=7.1 Hz), 7.48(2H, d, J=8.6 Hz), 7.68(2H, d, J=8.6 Hz), 7.70(2H, d, J=8.5 Hz), 7.84(2H, d, J=8.5 Hz), 7.85(2H, d, J=8.8 Hz), 8.00(2H, d, J=8.8 Hz). |
| 3 | (CD$_3$OD) | δ: 3.19(3H, br s), 3.51(3H, s), 3.62–3.92(4H, m), 4.16(2H, br d), 7.64(2H, d, J=8.3 Hz), 8.02(2H, d, J=8.3 Hz), 8.43(1H, br s). |
| 4 | (d-DMSO) | δ: 3.43–3.45(2H, m), 3.48(3H, s), 3.56(2H, t, J=5.4 Hz), 3.64(3H, s), 4.14(2H, s), 7.67(2H, d, J=8.4 Hz), 8.06(2H, d, J=8.4 Hz), 8.59(1H, s), 9.50–9.70(3H, br s). |
| 5 | (CD$_3$OD) | δ: 1.28(6H, d, J=6.1 Hz), 3.47(3H, s), 3.50–3.80(4H, m), 4.01(2H, s), 4.40–4.43(1H, m), 7.64(2H, d, J=8.3 Hz), 7.98(2H, d, J=8.3 Hz), 8.25(1H, br s). |
| 6 | (CD$_3$CD) | δ: 1.28(6H, d, J=6.4 Hz), 3.48(3H, s), 3.72(3H, s), 3.68–6.82(4H, m), 4.14(2H, s), 4.37–4.48(1H, m), 7.68(2H, d, J=8.5 Hz), 8.00(2H, d, J=8.5 Hz), 8.25(1H, br s). |
| 7 | (d-DMSO) | δ: 1.73–1.77(2H, m), 3.38(2H, t, J=6.7 Hz), 3.47(3H, s), 3.53(2H, t, J=6.1 Hz), 3.98(2H, s), 7.65(2H, d, J=8.5 Hz), 8.00(2H, d, J=8.5 Hz), 8.51(1H, s), 11.0–12.0(3H, br s). |
| 8 | (d-DMSO) | δ: 1.40–1.54(2H, m), 1.69–1.89(2H, m), 3.17–3.86(5H, m), 3.74(3H, s), 3.80–4.04(2H, m), 7.58(2H, d, J=8.7 Hz), 7.92(2H, d, J=8.7 Hz), 8.16(1H, m), 9.80–10.6(3H, br s). |
| 9 | (d-DMSO) | δ: 1.79(3H, t, J=7.1 Hz), 1.30–1.55(2H, m), 1.70–2.05(2H, m), 3.12–3.78(4H, m), 3.39(3H, s), 3.87–4.01(1H, m), 4.03(2H, q, J=7.1 Hz), 4.14(2H, s), 7.63(2H, d, J=8.7 Hz), 8.00(2H, d, J=8.7 Hz), 8.43(1H, s), 9.28(1H, br s), 9.50(2H, br s). |
| 10 | (D$_2$O) | δ: 1.64–2.05(4H, m), 3.25–4.12(4H, m), 3.35(3H, s), 3.78(1H, br s), 4.01(2H, s), 7.70(2H, d, J=8.3 Hz), 8.03(2H, d, J=8.3 Hz), 8.17(1H, s). |
| 11 | (d-DMSO) | δ: 1.18(3H, t, J=7.1 Hz), 1.21–1.86(4H, m), 3.20–3.89(4H, m), 3.34(3H, s), 3.62–3.65(1H, m), 4.03(2H, q, J=7.1 Hz), 4.15(2H, s), 7.63(2H, d, J=8.7 Hz), 7.98(2H, d, J=8.7 Hz), 8.42(1H, s), 9.42(3H, br s). |
| 13 | (CDCl$_3$) | δ: 1.20(3H, t, J=7.2 Hz), 3.05(3H, s), 3.48–3.53(2H, m), 3.61–3.65(2H, m), 4.05(2H, s), 4.11(2H, q, J=7.2 Hz), 7.47–7.60(5H, m), 7.64(2H, br s), |

TABLE III-continued

| No. | | ¹H-NMR |
|---|---|---|
| | | 8.12(2H, br s), 8.65(1H, br s), 9.04(1H, s), 9.36(2H, s). |
| 15 | (CD₃OD) | δ: 1.27(3H, t, J=7.3 Hz), 3.07(3H, s), 3.20(3H, s), 3.31–3.33(4H, m), 4.18(2H, q, J=7.3 Hz), 4.25(2H, s), 7.54–7.72(5H, m), 7.83(2H, d, J=8.5 Hz), 8.00(2H, d, J=8.5 Hz). |
| 17 | (CD₃OD) | δ: 1.44–1.98(4H, m), 3.38(3H, s), 3.41–4.07(5H, m), 3.97(2H, s), 7.67–7.76(5H, m), 7.91(2H, d, J=8.7 Hz), 8.11(2H, d, J=8.7 Hz). |
| | (D₂O) | δ: 1.48–2.03(4H, m), 3.20–4.09(5H, m), 3.33(3H, s), 3.95(2H, s), 7.58–7.68(5H, m), 7.80(2H, d, J=8.4 Hz), 8.05(2H, d, J=8.4 Hz). |
| 20 | (CD₃OD) | δ: 1.33(3H, t, J=7.1 Hz), 3.33(3H, s), 3.61(2H, t, J=5.3 Hz), 3.75(2H, t, J=5.3 Hz), 4.22(2H, s) 4.27(2H, q, J=7.1 Hz), 7.49–7.51(1H, m), 7.56–7.60(2H, m), 7.79–7.81(2H, m), 7.82(2H, d, J=8.4 Hz), 7.91(2H, d, J=8.4 Hz), 7.92(2H, d, J=8.7 Hz), 8.11(2H, d, J=8.7 Hz). |
| 22 | (CO(CD₃)₂) | δ: 1.42–1.92(4H, m), 3.34(3H, s), 3.41–4.00(4H, m), 3.69(1H, br s), 4.19(2H, s), 7.41–7.45(1H, m), 7.48–7.52(2H, m), 7.71–7.76(4H, m), 7.87–7.90(2H, m), 7.89(2H, d, J=8.5 Hz), 8.11(2H, d, J=8.5 Hz). |
| 23 | (CDCl₃) | δ: 1.20(3H, t, J=7.2 Hz), 1.35–1.93(4H, m), 3.18(3H, s), 3.20–3.92(4H, m), 3.37(1H, s), 4.03(2H, s), 4.10(2H, q, J=7.2 Hz), 7.13–8.12(13H, m), 8.78–9.42(3H, br s). |
| 25 | (d-DMSO) | δ: 1.26(3H, t, J=7.1 Hz), 1.38(9H, s), 3.18(3H, s), 3.48–3.51(2H, m), 3.64–3.66(2H, m), 4.12(2H, s), 6.31(2H, q, J=7.1 Hz), 7.58–7.61(4H, m), 7.84(2H, d, J=8.7 Hz), 8.01(2H, d, J=8.7 Hz). |
| 28 | (CD₃CO₂D) | δ: 1.19–1.87(4H, m), 1.39(9H, s), 3.30(3H, s), 3.32–3.76(4H, m), 3.94–4.03(1H, m), 4.19(2H, s), 7.59(2H, d, J=8.4 Hz), 7.65(2H, d, J=8.4 Hz), 7.87(2H, d, J=8.8 Hz), 8.11(2H, d, J=8.8 Hz). |
| 29 | (d-DMSO) | δ: 1.20(3H, t, J=7.1 Hz), 1.33(9H, s), 1.71–1.81(4H, m), 3.05(3H, s), 3.55–3.80(4H, m), 4.11(2H, q, J=7.1 Hz), 4.12(2H, s), 7.54–7.62(4H, m), 7.83(2H, d, J=8.7 Hz), 8.01(2H, d, J=8.7 Hz), 9.52(3H, br s). |
| 31 | (CD₃OD) | δ: 1.23(3H, t, J=7.1 Hz), 3.22(3H, s), 3.51(2H, t, J=5.4 Hz), 3.65(2H, t, J=5.4 Hz), 4.12(2H, q, J=7.1 Hz), 4.14(2H, s), 7.48(2H, d, J=8.5 Hz), 7.70(2H, d, J=8.5 Hz), 7.72–7.80(4H, m), 7.82(2H, d, J=8.3 Hz), 8.00(2H, d, J=8.3 Hz). |
| 34 | (d-DMSO) | δ: 1.33(3H, t, J=7.1 Hz), 1.38(9H, s), 3.25(3H, s), 3.30–4.24(8H, m), 4.25(2H, s), 4.32(2H, q, J=7.1 Hz), 7.60(2H, d, J=9.7 Hz), 7.65(2H, d, J=9.7 Hz), 7.87(2H, d, J=8.4 Hz), 8.02(2H, d, J=8.4 Hz). |
| 36 | (d-DMSO) | δ: 1.20–1.22(3H, m), 3.25(3H, s), 3.31(3H, s), 3.66–3.77(4H, m), 4.05(2H, s), 4.11–4.15(2H, m), 7.35–7.48(3H, m), 7.67–7.86(8H, m), 8.00(2H, d, J=8.3 Hz). |
| 40 | (CD₃OD) | δ: 1.32(3H, t, J=7.1 Hz), 1.38(9H, s), 1.82–2.25(4H, m), 3.22(3H, s), 3.24–3.75(4H, m), 3.98–4.07(4H, m), 4.16(2H, s), 4.31(2H, q, J=7.1 Hz), 7.61(4H, s), 7.83(2H, d, J=8.6 Hz), 8.04(2H, d, J=8.6 Hz). |
| 41 | (CDCl₃) | δ: 2.56–2.68(4H, br d), 3.13(3H, s), 3.27(2H, s), 3.55–3.66(4H, br s), 7.44–7.46(1H, m), 7.53(2H, t, J=7.8 Hz), 7.75–7.80(4H, m), 7.87–7.92(4H, m), 8.07(2H, d, J=8.5 Hz), 9.46(1H, s), 9.54(2H, s). |
| 42 | (CDCl₃) | δ: 1.32(3H, t, J=7.1 Hz), 3.29(3H, s), 3.42–3.63(4H, m), 3.92–4.21(4H, m), 4.26(2H, s), 4.32(2H, q, J=7.1 Hz), 7.40–7.49(3H, m), 7.68–7.70(2H, m), 7.41(1H, t, J=7.3 Hz), 7.49(2H, t, J=7.3 Hz), 7.66–7.69(2H, m), 7.73(2H, d, J=8.4 Hz), 7.84(2H, d, J=8.8 Hz), 7.86(2H, d, J=8.4 Hz), 8.01(2H, d, J=8.8 Hz). |
| 43 | (CD₃OD) | δ: 1.38(9H, s), 1.82–2.22(4H, m), 3.15–3.66(4H, m), 3.21(3H, s), 3.30(2H, s), 3.59(1H, m), 7.60(4H, d, J=6.1 Hz), 7.81(2H, d, J=8.6 Hz), 8.03(2H, d, J=8.6 Hz). |
| 48 | (CDCl₃) | δ: 1.44(9H, s), 2.75(1H, br s), 3.35(3H, s), 3.42–3.76(4H, m), 3.93(2H, s), 7.41(2H, d, J=9.0 Hz), 7.73(2H, d, J=9.0 Hz), 8.12(1H, s). |
| 49 | (CDCl₃) | δ: 1.35(9H, s), 1.47(9H, s), 2.75(1H, br s), 2.90–3.22(6H, m), 3.59–3.97(6H, m), 7.42(4H, br s), 7.63(4H, br s). |

TABLE III-continued

| No. | | ¹H-NMR |
|---|---|---|
| 53 | (CDCl₃) | δ: 3.41(3H, s), 3.40–3.98(5H, m), 3.68(3H, s), 4.06(2H, s), 7.46(2H, d, J=8.0 Hz), 7.78(2H, d, J=8.0 Hz), 8.20(1H, br s). |
| 54 | (CDCl₃) | δ: 1.45(9H, s), 3.14(3H, br s), 3.33(3H, s), 3.62–3.82(4H, m), 3.93(2H, s), 7.42(2H, d, J=8.4 Hz), 7.72(2H, d, J=8.4 Hz), 8.10(1H, br s). |
| 55 | (CDCl₃) | δ: 1.28(6H, d, J=6.6 Hz), 3.37(3H, s), 3.52–3.82(4H, m), 4.11(2H, s), 4.22–4.59(1H, m), 7.57(2H, d, J=8.0 Hz), 7.82(2H, d, J=8.0 Hz), 8.07(1H, s). |
| 56 | (CDCl₃) | δ: 1.25(3H, t, J=7.2 Hz), 1.47–2.05(4H, m), 3.12–3.73(4H, m), 3.33(3H, s), 3.84–4.05(1H, m), 4.13(2H, s), 4.16(2H, q, J=7.2 Hz), 7.49(2H, d, J=8.8 Hz), 7.67(2H, d, J=8.8 Hz), 8.00(1H, s). |
| 57 | (CDCl₃) | δ: 1.26(3H, t, J=7.0 Hz), 1.45–2.02(4H, m), 2.75(3H, d, J=6.0 Hz), 3.08–3.98(5H, m), 4.10(2H, s), 4.12(2H, q, J=7.0 Hz), 7.51(2H, d, J=8.2 Hz), 7.69(2H, d, J=8.2 Hz), 8.05(1H, s). |
| 58 | (CDCl₃) | δ: 1.24(3H, t, J=7.0 Hz), 3.04(3H, s), 3.43–3.68(4H, m), 4.03(2H, s), 4.12(2H, q, J=7.0 Hz), 7.74(5H, s), 7.51–7.75(4H, m), 8.52–8.73(1H, m). |
| 59 | (CDCl₃) | δ: 1.24(3H, t, J=7.2 Hz), 2.93(3H, s), 4.02(3H, s), 3.43–3.64(4H, m), 3.82–4.03(2H, m), 4.05(2H, q, J=7.2 Hz), 7.32(5H, s), 7.51(4H, s). |
| 60 | (CDCl₃) | δ: 1.22(3H, t, J=7.0 Hz), 1.42–1.86(4H, m), 3.01(3H, s), 3.18–3.82(5H, m), 4.01(2H, s), 4.10(2H, q, J=7.0 Hz), 7.42(5H, s), 7.61(4H, s). |
| 61 | (CDCl₃) | δ: 1.24(3H, t, J=7.0 Hz), 3.06(3H, s), 3.52–3.68(4H, m), 4.05(2H, s), 4.14(2H, q, J=7.0 Hz), 7.20–7.74(9H, m), 7.62(4H, s), 8.58–8.82(1H, m). |
| 62 | (CDCl₃) | δ: 1.21(3H, t, J=7.0 Hz), 3.02(3H, s), 3.19(3H, s), 3.68–3.83(4H, m), 4.01(2H, s), 4.10(2H, q, J=7.0 Hz), 7.22–7.73(13H, m). |
| 63 | (CDCl₃) | δ: 1.25(3H, t, J=7.0 Hz), 1.51–1.92(4H, m), 3.10(3H, s), 3.30–3.82(4H, m), 4.18(2H, q, J=7.0 Hz), 7.29–7.82(13H, m). |
| 64 | (CDCl₃) | δ: 1.34(3H, t, J=7.0 Hz), 1.45(9H, s), 3.13(3H, s), 3.52–3.75(4H, m), 4.13(2H, s), 4.24(2H, q, J=7.0 Hz), 7.42(4H, s), 7.54(2H, d, J=6.8 Hz), 7.63(2H, d, J=6.8 Hz), 8.53–8.75(1H, m). |
| 65 | (CDCl₃) | δ: 1.27(3H, t, J=7.4 Hz), 1.36(9H, s), 3.04(3H, s), 3.09(3H, s), 3.54–3.81(4H, m), 4.03(2H, br s), 4.17(2H, q, J=7.4 Hz), 7.47(4H, s), 7.68(4H, s). |
| 66 | (CDCl₃) | δ: 1.27(3H, t, J=7.0 Hz), 1.35(9H, s), 1.30–2.00(4H, m), 3.05(3H, s), 3.25–3.80(5H, m), 4.06(2H, s), 4.20(2H, q, J=7.0 Hz), 7.45(4H, s), 7.74(4H, s). |
| 67 | (CDCl₃) | δ: 1.24(3H, t, J=7.0 Hz), 3.09(3H, s), 3.53–3.71(4H, m), 4.03(2H, s), 4.15(2H, q, J=7.0 Hz), 7.41–7.89 (12H, m), 8.55–8.73(1H, m). |
| 68 | (CDCl₃) | δ: 1.26(3H, t, J=7.0 Hz), 1.52–4.98(4H, m), 3.05(3H, s), 3.23–3.88(5H, m), 4.02(2H, s), 4.16(2H, q, J=7.0 Hz), 7.40(4H, s), 7.58(4H, s), 7.64(4H, s). |
| 109 | (CD₃OD) | δ: 1.38(9H, s), 1.85–2.27(4H, m), 3.28–3.65(4H, m), 3.30(3H, s), 3.60(1H, s), 4.14(2H, br s), 7.61(4H, s), 7.82(2H, d, J=8.6 Hz), 8.03(2H, d, J=8.6 Hz). |
| 110 | (CD₃OD) | δ: 1.32(3H, t, J=7.1 Hz), 1.38(9H, s), 1.81–2.27(4H, m), 3.22(3H, s), 3.23–3.76(4H, m), 3.96–4.18(1H, m), 4.16(2H, s), 4.31(2H, d, J=7.1 Hz), 7.61(4H, s), 7.83(2H, d, J=8.5 Hz), 8.04(2H, d, J=8.5 Hz). |
| 112 | (CD₃OD) | δ: 1.32(3H, t, J=7.1 Hz), 1.37(9H, s), 1.70–2.32(4H, m), 2.90(1.5H, s), 3.21–3.79(4H, m), 3.22(1.5H, s), 3.24(1.5H, s), 3.30(1.5H, s), 3.37–3.48(1H, m), 4.16–4.22(2H, m), 4.09(2H, q, J=7.1 Hz), 7.55(1H, d, J=8.3 Hz), 7.59(1H, d, J=8.3 Hz), 7.64(2H, d, J=8.3 Hz), 7.85(1H, d, J=8.8 Hz), 7.92(1H, d, J=8.8 Hz), 8.00(1H, d, J=8.8 Hz), 8.02(1H, d, J=8.8 Hz). |
| 114 | (CD₃OD) | δ: 1.23(1H, t, J=7.1 Hz), 1.26(2H, t, J=7.1 Hz), 1.38(9H, s), 1.46–1.94(4H, m), 2.73–4.69(4H, m), 3.19(2H, s), 3.30(1H, s), 3.80–3.88(0.7H, m), 3.92–4.04(1.3H, m), 4.05–4.12(0.3H, m), 4.08–4.18(0.7H, m), 4.16(1.3H, q, J=7.1 Hz), 4.23(0.7H, q, J=7.1 Hz), 7.57(2H, d, J=8.7 Hz), 7.66(2H, d, J=8.7 Hz), 7.85(2H, d, J=8.8 Hz), 8.01(2H, d, J=8.4 Hz), 8.06(0.3H, s), 8.23(0.7H, s). |
| 116 | (d-DMSO) | δ: 0.94–1.79(4H, m), 1.19(3H, t, J=7.1 Hz), 1.33(9H, s), 2.22(2H, s), 2.51(3H, s), 2.62–4.48(4H, m), 3.05(3H, s), 3.22–3.38(1H, m), 4.07(2H, q, |

TABLE III-continued

| No. | | ¹H-NMR |
|---|---|---|
| | | J=7.1 Hz), 7.51(2H, d, J=8.4 Hz), 7.62(2H, d, J=8.4 Hz), 7.84(2H, d, J=8.8 Hz), 8.01(2H, d, J=8.8 Hz), 9.18(2H, br s), 9.44(2H, br s). |
| 118 | (CD₃OD) | δ: 1.32(3H, t, J=7.1 Hz), 1.39(9H, s), 1.56–1.87(2H, m), 2.18–2.23(2H, m), 2.78–3.30(2H, m), 3.22(3H, s), 4.06(2H, s), 4.21–4.69(2H, m), 4.32(2H, q, J=7.1 Hz), 7.55(2H, d, J=8.3 Hz), 7.64(2H, d, J=8.3 Hz), 7.85(2H, d, J=8.5 Hz), 8.02(2H, d, J=8.5 Hz). |
| 120 | (d-DMSO) | δ: 1.19(1.8H, t, J=7.1 Hz), 1.23(1.2H, t, J=7.1 Hz), 1.26–1.79(4H, m), 1.35(9H, s), 1.93(1.2H, s), 2.11(1.8H, s), 2.65–4.54(4H, m), 3.05(3H, s), 3.64–3.79(1.2H, m), 3.88–4.03(0.8H, m), 3.90–4.08(1H, m), 4.06(1.2H, q, J=7.1 Hz), 4.17(0.8H, q, J=7.1 Hz), 7.59(2H, d, J=8.1 Hz), 7.62(2H, d, J=8.1 Hz), 7.84(2H, d, J=8.8 Hz), 8.02(2H, d, J=8.8 Hz), 9.19(2H, br s), 9.45(2H, br s). |
| 122 | (d-DMSO) | δ: 1.17(1.2H, t, J=7.1 Hz), 1.26(1.8H, t, J=7.1 Hz) 1.34(9H, s), 1.41–1.87(4H, m), 2.38–4.57(4H, m), 3.04(3H, s), 3.14–3.28(0.4H, m), 3.65–3.77(0.6H, m), 3.86–3.98(2H, m), 4.03(0.8H, q, J=7.1 Hz), 4.14(1.2H, q, J=7.1 Hz), 7.53–7.62(9H, m), 7.83(2H, d, J=8.2 Hz), 8.02(2H, d, J=8.6 Hz), 9.21(2H, br s), 9.46(2H, br s). |
| 124 | (d-DMSO) | δ: 1.18(1H, t, J=7.1 Hz), 1.24(2H, t, J=7.1 Hz), 1.34(9H, s), 1.41–1.87(4H, m), 2.46–4.58(4H, m), 3.04(3H, s), 3.64–3.82(1H, m), 3.80–3.98(2H, m), 4.03(0.7H, q, J=7.1 Hz), 4.14(1.3H, q, J=7.1 Hz), 7.48–7.64(4H, m), 7.80–7.83(2H, m), 8.01(2H, d, J=8.2 Hz), 8.53–8.74(2H, m), 9.12(2H, br s), 9.42(2H, br s). |
| 126 | (d-DMSO) | δ: 1.22(3H, t, J=7.1 Hz), 1.73–2.09(4H, m), 3.13–3.92(4H, m), 3.16(3H, s), 3.31–3.46(1H, m), 3.95–4.06(1H, m), 4.19(2H, q, J=7.1 Hz), 7.37–7.43(1H, m), 7.49–7.60(2H, m), 7.78–7.81(2H, m), 7.79(2H, d, J=8.4 Hz), 7.84(2H, d, J=8.4 Hz), 7.85(2H, d, J=8.1 Hz), 8.11(2H, d, J=8.1 Hz), 9.47(2H, br s), 9.68(2H, br s). |
| 128 | (d-DMSO) | δ: 0.91(3H, t, J=7.3 Hz), 1.19(3H, t, J=7.1 Hz), 1.20–1.83(4H, m), 1.27–1.36(2H, m), 1.55–1.68(2H, m), 2.66(3H, t, J=7.3 Hz), 3.05(3H, s), 3.13–3.91(4H, m), 3.52–3.61(1H, m), 4.10(2H, q, J=7.1 Hz), 4.12(2H, s), 7.42(2H, d, J=8.3 Hz), 7.53(2H, d, J=8.3 Hz), 7.84(2H, d, J=8.8 Hz), 7.99(2H, d, J=8.8 Hz), 9.14(2H, br s), 9.43(2H, br s). |
| 132 | (d-DMSO) | δ: 1.19(3H, t, J=7.1 Hz), 1.32–.89(4H, m), 3.12(3H, s), 3.14–3.93(4H, m), 3.58–3.64(1H, m), 4.09(2H, q, J=7.1 Hz), 4.14(2H, s), 7.44–7.46(1H, m), 7.76(2H, d, J=8.6 Hz), 7.88(2H, d, J=8.7 Hz), 7.93–7.98(1H, m), 8.02(2H, d, J=8.7 Hz), 8.09–8.13(2H, d, J=8.6 Hz), 9.16(2H, s), 9.45(2H, s). |
| 133 | (d-DMSO) | δ: 1.26–1.78(4H, m), 2.79(3H, s), 3.05(3H, s), 3.18–3.38(4H, m), 3.39–3.61(4H, m), 3.48–3.98(4H, m), 3.55–3.63(1H, m), 4.06(2H, s), 7.18(2H, d, J=8.9 Hz), 7.51(2H, d, J=8.9 Hz), 7.85(2H, d, J=8.8 Hz), 8.02(2H, d, J=8.8 Hz), 9.27(2H, br s), 9.49(2H, br s). |
| 134 | (d-DMSO) | δ: 1.20(3H, t, J=7.1 Hz), 1.24–1.80(4H, m), 2.80(3H, s), 3.05(3H, s), 3.06–3.21(4H, m), 3.22–3.38(4H, m), 3.40–4.16(4H, m), 3.63–3.75(1H, m), 4.09(2H, q, J=7.1 Hz), 4.15(2H, s), 7.17(2H, d, J=8.8 Hz), 7.51(2H, d, J=8.8 Hz), 7.84(2H, d, J=8.5 Hz), 8.01(2H, d, J=8.5 Hz), 9.23(2H, s), 9.47(2H, s). |
| 136 | (d-DMSO) | δ: 1.20(3H, t, J=7.1 Hz), 1.30(3H, t, J=7.3 Hz), 1.31–1.89(4H, m), 3.06(3H, s), 3.07(2H, q, J=7.3 Hz), 3.08–3.97(4H, m), 3.12–3.39(4H, m), 3.22–3.35(1H, m), 3.53–4.08(4H, m), 4.10(2H, q, J=7.1 Hz), 4.15(2H, s), 7.18(2H, d, J=8.7 Hz), 7.51(2H, d, J=8.7 Hz), 7.84(2H, d, J=8.6 Hz), 8.02(2H, d, J=8.6 Hz), 9.26(2H, br s), 9.49(2H, br s). |
| 137 | (d-DMSO) | δ: 1.37–1.88(4H, m), 3.12(3H, s), 3.15–3.95(4H, m), 3.56–3.68(1H, m), 3.82(2H, s), 7.78(2H, d, J=8.1 Hz), 7.87(2H, d, J=8.1 Hz), 7.92–8.09(8H, m), 9.38(3H, br s), 10.1(3H, br s). |
| 138 | (d-DMSO) | δ: 1.20(3H, t, J=7.1 Hz), 1.32–1.78(4H, m), 3.08–3.88(4H, m), 3.13(3H, s), 3.55–3.66(1H, m), 4.09(2H, q, J=7.1 Hz), 4.15(2H, s), 7.79(2H, d, |

TABLE III-continued

| No. | | ¹H-NMR |
|---|---|---|
| | | J=8.6 Hz), 7.87(2H, d, J=8.6 Hz), 7.98–8.11(8H, m), 9.36(3H, br s), 9.55(3H, br s). |
| 140 | (CDCl₃) | δ: 1.22(3H, t, J=7 Hz), 1.32(9H, s), 1.5–2.4(4H, m), 2.7–3.0(5H, m), 2.99(3H, s), 3.12(2H, s), 4.0–4.5(1H, m), 4.10(2H, q, J=7 Hz), 7.39(4H, s), 7.63(4H, s). |
| 141 | (CDCl₃) | δ: 1.25(3H, t, J=7 Hz), 1.35(9H, s), 1.2–2.2(4H, m), 2.2–3.0(2H, m), 3.00(3H, s), 3.0–4.2(4H, m), 4.08(2H, q, J=7 Hz), 4.4–5.0(1H, m), 7.42(4H, s), 7.54(4H, s), 7.92(0.2H, s), 8.09(0.8H, s). |
| 142 | (CDCl₃) | δ: 1.24(3H, t, J=7 Hz), 1.34(9H, s), 1.4–2.1(4H, m), 2.29(3H, s), 2.3–3.0(4H, m), 3.02(3H, s), 3.23(2H, s), 4.12(2H, q, J=7 Hz), 4.2–4.9(1H, m), 7.42(4H, s), 7.64(4H, s). |
| 143 | (CDCl₃) | δ: 1.27(3H, t, J=7.1 Hz), 1.29(3H, t, J=7.3 Hz), 1.37(9H, s), 1.3–.9(4H, m), 2.01(1.7H, s), 2.18(1.3H, s), 2.6–4.9(7H, m), 3.05(3H, s), 4.16(0.9H, m), 4.21(1.1H, q, J=7.1 Hz), 7.51(4H, m), 7.69(2H, m), 7.80(2H, m). |
| 144 | (CDCl₃) | δ: 1.2–2.0(7H, m), 1.36(9H, s), 2.4–3.2(2H, m), 3.05(3H, s), 3.7–4.9(7H, m), 7.3–7.6(9H, m), 7.7–7.8(2H, m), 7.8–7.9(2H, m). |
| 145 | (CDCl₃) | δ: 1.2–2.0(7H, m), 1.37(9H, s), 2.4–4.9(9H, m), 3.06(3H, s), 7.3–7.4(1H, m), 7.4–7.6(4H, m), 7.7(2H, m), 7.7–7.8(1H, m), 7.8(2H, m), 8.6–8.7(2H, m). |
| 149 | (CDCl₃) | δ: 1.27(3H, t, J=7.1 Hz), 1.58(1H, m), 1.69(1H, m), 1.77(1H, m), 1.87(1H, m), 3.09(3H, s), 3.34(1H, m), 3.57(1H, m), 3.63(1H, m), 3.69(1H, m), 3.92(1H, m), 4.08(2H, m), 4.19(2H, q, J=7.1 Hz), 7.32(1H, m), 7.68(2H, d, J=8.4 Hz), 7.71(2H, d, J=8.8 Hz), 7.79(2H, d, J=8.8 Hz), 7.80(1H, m), 7.83(1H, m), 8.15(2H, d, J=8.4 Hz), 8.74(1H, m). |
| 150 | (CDCl₃) | δ: 1.27(3H, t, J=7.1 Hz), 1.46–1.92(4H, m), 2.36(3H, s), 2.54–5.59(4H, m), 3.05(3H, s), 3.25–4.00(4H, m), 3.31–3.37(4H, m), 3.57–3.65(1H, m), 4.08(2H, s), 4.20(2H, q, J=7.1 Hz), 6.94(2H, d, J=8.8 Hz), 7.41(2H, d, J=8.8 Hz), 7.69(2H, d, J=8.5 Hz), 7.76(2H, d, J=8.5 Hz). |
| 151 | (CDCl₃) | δ: 1.15(3H, t, J=7.1 Hz), 1.28(3H, t, J=7.1 Hz), 1.5–2.0(4H, m), 2.2–5.8(6H, m), 3.03(3H, s), 3.1–3.9(9H, m), 4.06(2H, s), 4.19(2H, q, J=7.1 Hz), 6.88(2H, d, J=11 Hz), 7.38(2H, d, J=11 Hz), 7.67(4H, s). |
| 152 | (CDCl₃) | δ: 1.28(3H, t, J=7.1 Hz), 1.56–1.75(2H, m), 1.85–1.95(2H, m), 3.10(3H, s), 3.35–3.45(1H, m), 3.5–3.6(1H, m), 3.6–3.7(1H, m), 3.7–3.8(1H, m), 3.9–4.0(1H, m), 4.09(2H, s), 4.20(2H, q, J=7.1 Hz), 7.65–7.75(8H, m), 7.75–7.82(4H, m). |
| 154 | (d-DMSO) | δ: 0.92(3H, t, J=7.3 Hz), 1.03–1.79(4H, m), 1.20(3H, t, J=7.1 Hz), 1.28–1.41(2H, m), 1.55–1.67(2H, m), 2.61–2.72(2H, m), 3.05(3H, s), 3.48–4.54(4H, m), 3.69–3.80(1H, m), 3.86(2H, s), 4.11(2H, q, J=7.1 Hz), 7.43(2H, d, J=7.3 Hz), 7.56(2H, d, J=7.3 Hz), 7.84(2H, d, J=8.2 Hz), 8.04(2H, d, J=8.2 Hz), 9.32(2H, br s), 9.52(2H, br s). |

Formulation Example 1

| Tablets | |
|---|---|
| Compound No. 10 | 10 g |
| Lactose | 20 g |
| Starch | 4 g |
| Starch (for glue) | 1 g |
| Magnesium stearate | 0.1 g |
| Calcium carboxymethylcellulose | 7 g |
| Total | 42.1 g |

The above ingredients were mixed by a conventional method and made into sugar coated tablets containing 50 mg of the active ingredient per tablet.

Formulation Example 2

| Capsules | |
|---|---|
| Compound No. 8 | 10 g |
| Lactose | 20 g |
| Microcrystalline cellulose | 10 g |
| Magnesium stearate | 1 g |
| Total | 41 g |

The above ingredients were mixed by a conventional method and stuffed into gelatin capsules to give capsules containing 50 mg of the active ingredient per capsule.

Formulation Example 3

| Soft elastic capsules | |
| --- | --- |
| Compound No. 21 | 10 g |
| Corn oil | 35 g |
| Total | 45 g |

The above ingredients were mixed and made into soft elastic capsules by a conventional method.

Formulation Example 4

| Ointment | |
| --- | --- |
| Compound No. 11 | 1.0 g |
| White soft paraffin | 79 g |
| Olive oil | 20 g |
| Total | 100 g |

The above ingredients were mixed in a conventional method to give a 1% ointment.

Formulation Example 5
Aerosol suspension

| (A) | |
| --- | --- |
| Compound No. 26 | 0.25% |
| Isopropyl myristate | 0.10% |
| Ethanol | 26.40% |
| (B) | |
| A 60–40% mixture of 1,2-dichlorotetrafluoroethane and 1-chloropentafluoroethane | 73.25% |

The above composition (A) was mixed and the resulting liquid mixture was introduced into a vessel equipped with a valve. The propellant (B) was injected from the valve nozzle to a gauge pressure of from about 2.46 to 2.81 mg/cm$^2$ to give an aerosol suspension.

Test Examples
In vitro antiplatelet aggregation effect
(A) Antiplatelet aggregation effect in guinea pigs Nine parts by volume of blood was collected from the abdominal artery of Hartley male guinea-pigs (weight: about 300 g) in syringes containing 1 part by volume of 3.8% sodium citrate. The blood thus obtained was centrifuged at 200×g for 10 minutes at room temperature to obtain platelet rich plasma (PRP). Furthermore, the residue was centrifuged at 2000×g for 15 minutes to obtain platelet poor plasma (PPP). The measurement was effected by diluting PRP with PPP to 300,000/mm$^3$. PRP and PPP were put in cuvettes, and the measurement range of transmittance was adjusted to 0% in the case of PRP and to 100% in the case of PPP. Thereafter, a test sample drug dissolved in H$_2$O:MeOH (1:2) was added to PRP. After the PRP was incubated at 37° C. at 1000 rpm for 2 minutes, an aggregating agent was added to record an aggregation curve. The antiplatelet aggregation effect of the test sample drug was expressed by the concentration (IC$_{50}$: $\mu$M) at which the aggregation of the control sample was 50% inhibited. The aggregating agent collagen was used at the minimum concentration (1 to 2 $\mu$g/ml) which caused the maximum aggregation. The measurement of platelet aggregation was carried out by using NBS HEMA TRACER 601.

(B) Antiplatelet aggregation effect in humans

Blood was collected in a similar manner from the antidepressed vein of healthy normal humans by paracentesis and centrifuged at 200×g for 10 minutes at room temperature to obtain platelet rich plasma (PRP). Furthermore, the residue was centrifuged at 2,000×g for 15 minutes to obtain platelet poor plasma (PPP). PRP sample was prepared in the same manner as in the test on guinea pigs, and a test sample drug dissolved in H$_2$O:MeOH (1:2) was added, and the concentration (IC$_{50}$:$\mu$M) at which the aggregation of the control sample was 50% inhibited was calculated. The aggregation agent collagen was used at the minimum concentration (1 to 2 $\mu$g/ml) which caused the maximum aggregation.

Test Results

In vitro antiplatelet aggregation tests; (A) and (B) Tables IV-1 and 2 show antiplatelet aggregation effects of test compounds evaluated as IC$_{50}$ values ($\mu$M). The compound Nos. in Table I should be referred to for the structures of the compounds.

TABLE IV-1

| Compound No. | Guinea-pig PRP IC$_{50}$ | | Compound No. | Guinea-pig PRP IC$_{50}$ | |
| --- | --- | --- | --- | --- | --- |
| | ADP | Collagen | | ADP | Collagen |
| 2 | 8.1 | 3.9 | 109 | 3.4 | 4.0 |
| 7 | 300 | | 110 | 5.0 | 3.1 |
| 10 | 35 | 17 | 111 | 11 | 8.1 |
| 11 | 31 | 17 | 112 | 37 | 14 |
| 15 | 114 | 57 | 114 | 21 | 14 |
| 17 | 20 | 23 | 115 | 93 | 68 |
| 20 | 30 | 12 | 116 | | 90 |
| 23 | 17 | 9.3 | 125 | 42 | 4.2 |
| 24 | 46 | 19 | 126 | 76 | 7.6 |
| 25 | 43 | 20 | 128 | 20 | 7.1 |
| 27 | 41 | 20 | | | |
| 28 | 25 | 17 | | | |

TABLE IV-2

| Compound No. | Guinea-pig PRP IC$_{50}$ | | Compound No. | Guinea-pig PRP IC$_{50}$ | |
| --- | --- | --- | --- | --- | --- |
| | ADP | Collagen | | ADP | Collagen |
| 1 | 36 | 5.9 | 112 | 2.5 | 5.1 |
| 2 | 2.8 | 2.4 | 113 | 0.17 | 0.14 |
| 3 | 12 | 8.8 | 114 | 1.2 | 1.6 |
| 4 | 56 | 12 | 115 | 2.0 | 2.0 |
| 5 | | 14 | 116 | 14 | 11 |
| 6 | | 20 | 117 | 8.4 | 7.8 |
| 7 | | 24 | 118 | 28 | 14 |
| 8 | 88 | 45 | 119 | 11 | 13 |
| 9 | 211 | 50 | 120 | 21 | 19 |
| 10 | 2.7 | 1.6 | 121 | 12 | 9.7 |
| 11 | 46 | 32 | 122 | 17 | 13 |
| 12 | 3.6 | 1.6 | 123 | 11 | 11 |
| 13 | | 2.5 | 124 | 13 | 16 |
| 14 | 1.2 | 1.3 | 125 | 3.3 | 2 |
| 15 | 3.9 | 1.4 | 126 | | 53 |
| 16 | 22 | 9.5 | 127 | 0.067 | 0.063 |
| 17 | 0.48 | 0.47 | 128 | 0.32 | 0.18 |
| 19 | 0.53 | 0.4 | 129 | | 0.55 |
| 20 | 0.92 | 0.38 | 130 | | 4.5 |
| 21 | 3.5 | 2.3 | 131 | 0.13 | 0.06 |
| 22 | 0.16 | 0.21 | 132 | | 1.7 |
| 23 | 1.5 | 0.88 | 133 | 0.48 | 0.35 |
| 24 | 0.53 | 0.4 | 134 | 12 | 12 |

TABLE IV-2-continued

| Compound No. | Guinea-pig PRP IC$_{50}$ | | Compound No. | Guinea-pig PRP IC$_{50}$ | |
|---|---|---|---|---|---|
| | ADP | Collagen | | ADP | Collagen |
| 25 | 0.52 | 0.48 | 135 | 0.46 | 0.37 |
| 26 | 0.72 | 0.56 | 136 | | 4 |
| 27 | 0.9 | 0.51 | 137 | | 0.063 |
| 109 | 2.6 | 2.1 | 138 | | 0.46 |
| 110 | 34 | 23 | 153 | | 0.13 |
| 111 | 1.8 | 1.5 | 154 | | 1.9 |

INDUSTRIAL APPLICABILITY

The compounds of the present invention have an inhibitory action on platelet aggregation and are useful as preventive and therapeutic agents for various thrombotic diseases.

We claim:
1. A pyrazolone derivative represented by general formula (I) or a salt thereof:

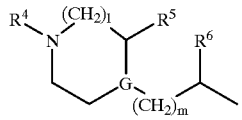

(I)

[wherein one of $X^1$ and $X^2$ is

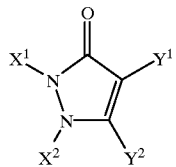

}wherein A is a cyano group, a cyano $C_{1-4}$ alkyl group, an amino group, an amino $C_{1-4}$ alkyl group, an amidino group or a guanidino group (the amino group, the amino $C_{1-4}$ alkyl group, the amidino group and the guanidino group may be substituted at a nitrogen atom with a $C_{1-6}$ alkyl group, a $C_{1-4}$ alkoxycarbonyl group, an aryl $C_{1-4}$ alkyloxycarbonyl group, an aryloxycarbonyl group or an arylcarbonyl group), $R^1$ and $R^2$ are independently hydrogen atoms, halogen atoms, $C_{1-6}$ alkyl groups, hydroxyl groups, $C_{1-4}$ alkyloxy groups, $C_{1-4}$ alkylsulfenyl groups, $C_{1-4}$ alkylsulfinyl groups, $C_{1-4}$ alkylsulfonyl groups, $R^3R^{3'}N$— groups or $R^3R^{3'}NCO$— groups, and $R^3$ and $R^{3'}$ are independently hydrogen atoms, $C_{1-6}$ alkyl groups, aryl $C_{1-4}$ alkyl groups, aryl groups, $C_{1-4}$ alkylcarbonyl groups, aryl $C_{1-4}$ alkylcarbonyl groups, arylcarbonyl groups, $C_{1-4}$ alkylsulfonyl groups, aryl $C_{1-4}$ alkylsulfonyl groups or arylsulfonyl groups}, a A-B- group (wherein A is the same as defined above, and B is a $C_{1-6}$ alkylene group, a $C_{3-6}$ alkenylene group or a cyclic $C_{3-7}$ alkylene group),

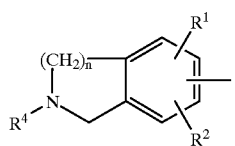

{wherein G is a nitrogen atom or a CH group, $R^4$ is a hydrogen atom, a $C_{1-6}$ alkyl group, a formyl group, an acetyl group, a benzyl group or an amidino group (the amidino group may be substituted with a $C_{1-6}$ alkyl group, a $C_{1-4}$ alkyloxycarbonyl group, an aryl $C_{1-4}$ alkyloxycarbonyl group, an aryloxycarbonyl group or an arylcarbonyl group), l is 0, 1 or 2, m is 1 or 2, and $R^5$ and $R^6$ are independently hydrogen atoms or $C_{1-6}$ alkyl groups or together represent a methylene group, an ethylene group or a —CH=CH— group) or

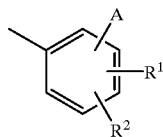

(wherein $R^1$, $R^2$ and $R^4$ are the same as defined above, and n is 1, 2 or 3),
the other of $X^1$ and $X^2$ is a $C_{1-6}$ alkyl group, a $C_{3-6}$ alkenyl group, an aryl $C_{1-4}$ alkyl group or an aryl group,
one of $Y^1$ and $Y^2$ is

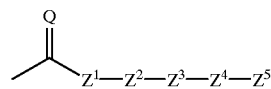

{wherein Q is an oxygen atom or a sulfur atom, $Z^1$ is an oxygen atom, a —NR$^7$— group or a —CHR$^7$— group, $Z^2$ is an cyclic $C_{3-7}$ alkylene group, a $C_{1-3}$ alkylene group, a —CH$_2$CO— group or a —CH$_2$CH$_2$CO— group (the $C_{1-3}$ alkylene group, the —CH$_2$CO— group and the —CH$_2$CH$_2$CO— group may be substituted with $R^8$), $Z^3$ is an oxygen atom, a sulfur atom, a sulfinyl group, a sulfonyl group or a —NR$^9$— group, $Z^4$ is a $C_{1-3}$ alkylene group (the $C_{1-3}$ alkylene group may be substituted with $R^{10}$), $Z^5$ is a carboxyl group, a $C_{1-4}$ alkyloxycarbonyl group, an aryl $C_{1-4}$ alkyloxycarbonyl group, an aryloxycarbonyl group, a sulfo group, a phosphono group, a O—$C_{1-4}$ alkylphosphono group, a O,O'-di-$C_{1-4}$ alkylphosphono group or a tetrazol-5-yl group, $R^7$ is a hydrogen atom, a $C_{1-6}$ alkyl group, an aryl $C_{1-4}$ alkyl group or an aryl group, or represents together with $R^8$ a methylene group or an ethylene group, or represents together with $R^9$ an ethylene group or a —CH$_2$CO— group when $Z^2$ is a methylene group or an ethylene group, $R^8$ is a $C_{1-6}$ alkyl group, an aryl $C_{1-4}$ alkyl group or an aryl group, or represents together with $R^7$ a methylene group or an ethylene group or represents together with $R^9$ a methylene group or an ethylene group, $R^9$ is a hydrogen atom, a formyl group, a $C_{1-4}$ alkylcarbonyl group, an arylcarbonyl group, a pyridylcarbonyl group, a $C_{1-6}$ alkyl group, an aryl $C_{1-4}$ alkyl group or an aryl group, or represents together with $R^8$ a methylene group or an ethylene group or represents together with $R^7$ an ethylene group or a —COCH$_2$— group when $Z^2$ is a methylene group or an ethylene group, and $R^{10}$ is a $C_{1-6}$ alkyl group, an aryl $C_{1-4}$ alkyl group or an aryl group}, and
the other of $Y^1$ and $Y^2$ is a D-E- group (wherein E is a bond, a $C_{1-4}$ alkylene group or a phenylene group (the phenylene group may be substituted with a halogen atom, a hydroxyl group, a $C_{1-4}$ alkyloxy group or a $C_{1-6}$ alkyl group), and D is a hydrogen atom, a $C_{1-6}$ alkyl group,

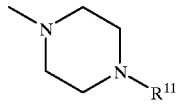

(wherein $R^{11}$ is a hydrogen atom, a $C_{1-6}$ alkyl group, a benzyl group or a formyl group), a pyridyl group or a phenyl group (the pyridyl group and the phenyl group may be substituted with a halogen atom, a hydroxyl group, a $C_{1-4}$ alkyloxy group, a $R^3R^{3'}N$— group, a $R^3R^{3'}NCO$— group (wherein $R^3$ and $R^{3'}$ are the same as defined above), a cyano group, an amidino group (which may be substituted at a nitrogen atom with a $C_{1-6}$ alkyl group, a $C_{1-4}$ alkoxycarbonyl group, an aryl $C_{1-4}$ alkyloxycarbonyl group, an aryloxycarbonyl group or an arylcarbonyl group) or a $C_{1-6}$ alkyl group}], {wherein the aryl group is a phenyl group or a naphthyl group (the phenyl group and the naphthyl group may be substituted with a carboxyl group, a $C_{1-4}$ alkyloxycarbonyl group, a $C_{1-4}$ alkylcarbonyl group, a $R^3R^{3'}NCO$— group, a $R^3R^{3'}NSO2$— group, a nitro group, a $R^3R^{3'}N$— group, a $C_{1-4}$ alkylsulfenyl group, a $C_{1-4}$ alkylsulfinyl group, a $C_{1-4}$ alkylsulfonyl group, a $C_{1-4}$ alkylcarbonyl-$NR^3$— group, a phenyl $C_{1-4}$ alkylcarbonyl-$NR^3$— group, a phenylcarbonyl-$NR^3$— group, a $C_{1-4}$ alkylsulfonyl-$NR^3$— group, a phenyl $C_{1-4}$ alkylsulfonyl-$NR^3$— group or a phenylsulfonyl-$NR^3$— group (wherein $R^3$ and $R^{3'}$ are the same as defined above), a halogen atom, a hydroxyl group, a $C_{1-4}$ alkyloxy group or a $C_{1-6}$ alkyl group})].

2. The pyrazolone derivative according to claim 1 or a salt thereof, wherein one of $X^1$ and $X^2$ is

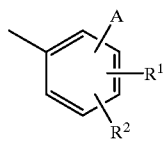

{wherein A is a cyano group, an amino group, an amidino group or a guanidino group (the amino group, the amidino group and the guanidino group may be substituted at a nitrogen atom with a $C_{1-6}$ alkyl group, a $C_{1-4}$ alkyloxycarbonyl group, an aryl $C_{1-4}$ alkyloxycarbonyl group, an aryloxycarbonyl group or an arylcarbonyl group), $R^1$ and $R^2$ are independently hydrogen atoms, halogen atoms, $C_{1-6}$ alkyl groups, hydroxyl groups, $C_{1-4}$ alkyloxy groups, $C_{1-4}$ alkylsulfenyl groups, $C_{1-4}$ alkylsulfinyl groups, $C_{1-4}$ alkylsulfonyl groups, $R^3R^{3'}N$— groups or $R^3R^{3'}NCO$— groups, and $R^3$ and $R^{3'}$ are independently hydrogen atoms, $C_{1-6}$ alkyl groups, aryl $C_{1-4}$ alkyl groups, aryl groups, $C_{1-4}$ alkylcarbonyl groups, aryl $C_{1-4}$ alkylcarbonyl groups, arylcarbonyl groups, $C_{1-4}$ alkylsulfonyl groups, aryl $C_{1-4}$ alkylsulfonyl groups or arylsulfonyl groups}, a A-B- group (wherein A is the same as defined above, and B is a $C_{1-6}$ alkylene group),

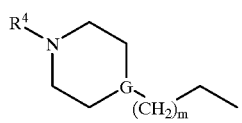

{wherein G is a nitrogen atom or a CH group, $R^4$ is a hydrogen atom, a $C_{1-6}$ alkyl group, a formyl group, an acetyl group, a benzyl group or an amidino group (the amidino group may be substituted with a $C_{1-6}$ alkyl group, a $C_{1-4}$ alkyloxycarbonyl group, an aryl $C_{1-4}$ alkyloxycarbonyl group, an aryloxycarbonyl group or an arylcarbonyl group), and m is 1 or 2} or

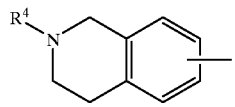

(wherein $R^4$ is the same as defined above), and the other of $X^1$ and $X^2$ is a $C_{1-6}$ alkyl group, a $C_{3-6}$ alkenyl group, an aryl $C_{1-4}$ alkyl group or an aryl group.

3. The pyrazolone derivative according to claim 2 or a salt thereof, wherein one of $Y^1$ and $Y^2$ is

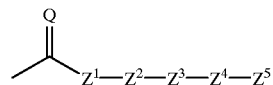

{wherein Q is an oxygen atom or a sulfur atom, $Z^1$ is an oxygen atom, a —$NR^7$— group or a —$CHR^7$— group, $Z^2$ is a cyclic $C_{3-7}$ alkylene group, a $C_{1-3}$ alkylene group, a —$CH_2CO$— group or a —$CH_2CH_2CO$— group, (the $C_{1-3}$ alkylene group, the —$CH_2CO$— group and the —$CH_2CH_2CO$— group may be substituted with $R^8$), $Z^3$ is an oxygen atom, a sulfur atom, a sulfinyl group, a sulfonyl group or a —$NR^9$— group, $Z^4$ is a $C_{1-3}$ alkylene group (the $C_{1-3}$ alkylene group may be substituted with $R^{10}$), $Z^5$ is a carboxyl group, a $C_{1-4}$ alkyloxycarbonyl group, an aryl $C_{1-4}$ alkyloxycarbonyl group, an aryloxycarbonyl group, a sulfo group, a phosphono group, a O—$C_{1-4}$ alkylphosphono group, a $O,O^1$-di-$C_{1-4}$ alkylphosphono group or a tetrazol-5-yl group, $R^7$ is a hydrogen atom, a $C_{1-6}$ alkyl group, an aryl $C_{1-4}$ alkyl group or an aryl group, $R^9$ is a hydrogen atom, a formyl group, a $C_{1-4}$ alkylcarbonyl group, an arylcarbonyl group, a pyridylcarbonyl group, a $C_{1-6}$ alkyl group, an aryl $C_{1-4}$ alkyl group or an aryl group, and $R^8$ and $R^{10}$ are $C_{1-6}$ alkyl groups, aryl $C_{1-4}$ alkyl groups or aryl groups},

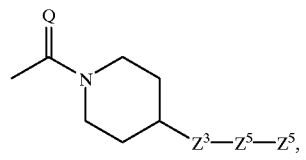

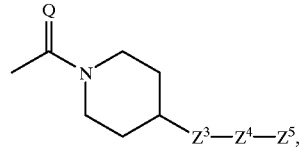

-continued

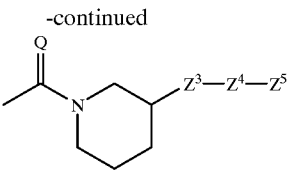

(wherein Q, $Z^3$, $Z^4$ and $Z^5$ are the same as defined above),

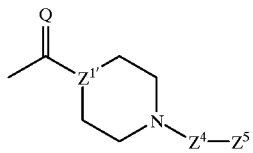

(wherein $Z^{1'}$ is a nitrogen atom or a $CR^7$ group, and Q, $R^7$, $Z^4$ and $Z^5$ are the same as defined above) or

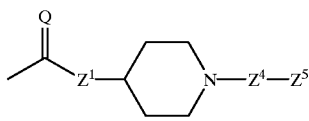

(wherein Q, $Z^1$, $Z^4$ and $Z^5$ are the same as defined above), and the other of $Y^1$ and $Y^2$ is a D-E- group [wherein E is a bond, a $C_{1-4}$ alkylene group or a phenylene group (the phenylene group may be substituted with a halogen atom, a hydroxyl group, a $C_{1-4}$ alkyloxy group or a $C_{1-6}$ alkyl group), and D is a hydrogen atom, a $C_{1-6}$ alkyl group,

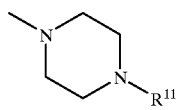

(wherein $R^{11}$ is a hydrogen atom, a $C_{1-6}$ alkyl group, a benzyl group or a formyl group), a pyridyl group or a phenyl group {the pyridyl group and the phenyl group may be substituted with a halogen atom, a hydroxyl group, a $C_{1-4}$ alkyloxy group, a $R^3R^{3'}N$— group, a $R^3R^{3'}NCO$— group (wherein $R^3$ and $R^{3'}$ are independently hydrogen atoms, $C_{1-6}$ alkyl groups, aryl $C_{1-4}$ alkyl groups, aryl groups, $C_{1-4}$ alkylcarbonyl groups, aryl $C_{1-4}$ alkylcarbonyl groups, arylcarbonyl groups, $C_{1-4}$ alkylsulfonyl groups, aryl $C_{1-4}$ alkylsulfonyl groups or arylsulfonyl groups), a cyano group, an amidino group (which may be substituted at a nitrogen atom with a $C_{1-6}$ alkyl group, a $C_{1-4}$ alkoxycarbonyl group, an aryl $C_{1-4}$ alkyloxycarbonyl group, an aryloxycarbonyl group or an arylcarbonyl group) or a $C_{1-6}$ alkyl group}].

4. The pyrazolone derivative according to claim 3 or a salt thereof, wherein Q is an oxygen atom.

5. The pyrazolone derivative according to claim 4 or a salt thereof, wherein $Y^1$ is

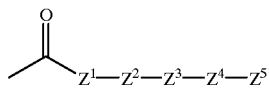

{wherein $Z^1$ is an oxygen atom, a —$NR^7$— group or a —$CHR^7$— group, $Z^2$ is a cyclic $C_{3-7}$ alkylene group, a $C_{1-3}$ alkylene group, a —$CH_2CO$— group or a —$CH_2CH_2CO$— group (the $C_{1-3}$ alkylene group, the —$CH_2CO$— group and the —$CH_2CH_2CO$— group may be substituted with $R^8$), $Z^3$ is an oxygen atom, a sulfur atom, a sulfinyl group, a sulfonyl group or a —$NR^9$— group, $Z^4$ is a $C_{1-3}$ alkylene group (the $C_{1-3}$ alkylene group may be substituted with $R^{10}$), $Z^5$ is a carboxyl group, a $C_{1-4}$ alkyloxycarbonyl group, an aryl $C_{1-4}$ alkyloxycarbonyl group, an aryloxycarbonyl group, a sulfo group, a phosphono group, a O—$C_{1-4}$ alkylphosphono group, a O,O'-di-$C_{1-4}$ alkylphosphono group or a tetrazol-5-yl group, $R^7$ is a hydrogen atom, a $C_{1-6}$ alkyl group, an aryl $C_{1-4}$ alkyl group or an aryl group, $R^9$ is a hydrogen atom, a formyl group, a $C_{1-4}$ alkylcarbonyl group, an arylcarbonyl group, a pyridylcarbonyl group, a $C_{1-6}$ alkyl group, an aryl $C_{1-4}$ alkyl group or an aryl group, and $R^8$ and $R^{10}$ are $C_{1-6}$ alkyl groups, aryl $C_{1-4}$ alkyl groups or aryl groups},

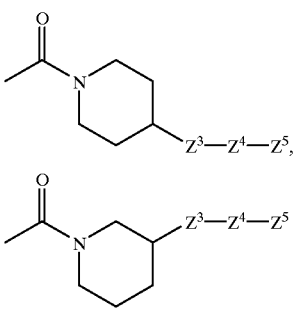

(wherein $Z^3$, $Z^4$ and $Z^5$ are the same as defined above),

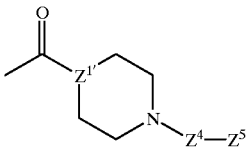

(wherein $Z^{1'}$ is a nitrogen atom or a $CR^7$ group, and $R^7$, $Z^4$ and $Z^5$ are the same as defined above) or

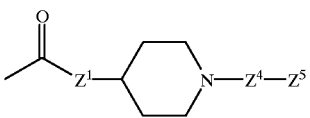

(wherein $Z^1$, $Z^4$ and $Z^5$ are the same as defined above), and
$Y^2$ is a D-E- group [wherein E is a bond, a $C_{1-4}$ alkylene group or a phenylene group (the phenylene group may be substituted with a halogen atom, a hydroxyl group, a $C_{1-4}$ alkyloxy group or a $C_{1-6}$ alkyl group), and D is a hydrogen atom, a $C_{1-6}$ alkyl group,

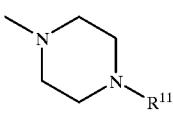

(wherein $R^{11}$ is a hydrogen atom, a $C_{1-6}$ alkyl group, a benzyl group or a formyl group), a pyridyl group or a phenyl group {the pyridyl group and the phenyl group may be substituted with a halogen atom, a hydroxyl group, a $C_{1-4}$ alkyloxy group, a $R^3R^{3'}$ N— group, a $R^3R^{3'}$ NCO— group (wherein $R^3$ and $R^{3'}$ are independently hydrogen atoms, $C_{1-6}$ alkyl groups, aryl $C_{1-4}$ alkyl groups, aryl groups, $C_{1-4}$ alkylcarbonyl groups, aryl $C_{1-4}$ alkylcarbonyl groups, arylcarbonyl groups, $C_{1-4}$ alkylsulfonyl groups, aryl $C_{1-4}$ alkylsulfonyl group or arylsulfonyl groups), a cyano group, an amidino group (which may be substituted at a nitrogen atom with a $C_{1-6}$ alkyl group, a $C_{1-4}$ alkoxycarbonyl group, an aryl $C_{1-4}$ alkyloxycarbonyl group, an aryloxycarbonyl group or an arylcarbonyl group) or a $C_{1-6}$ alkyl group)]}.

6. The pyrazolone derivative according to claim 5 or a salt thereof, wherein $X^1$ is

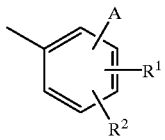

{wherein A is a cyano group, an amino group, an amidino group or a guanidino group (the amino group, the amidino group and the guanidino group may be substituted at a nitrogen atom with a $C_{1-6}$ alkyl group, a $C_{1-4}$ alkyloxycarbonyl group, an aryl $C_{1-4}$ alkyloxycarbonyl group, an aryloxycarbonyl group or an arylcarbonyl group), $R^1$ and $R^2$ are independently hydrogen atoms, halogen atoms, $C_{1-6}$ alkyl groups, hydroxyl groups, $C_{1-4}$ alkyloxy groups, $C_{1-4}$ alkylsulfenyl groups, $C_{1-4}$ alkylsulfinyl groups, $C_{1-4}$ alkylsulfonyl groups, $R^3R^{3'}N$— groups or $R^3R^{3'}NCO$— groups, and $R^3$ and $R^{3'}$ are independently hydrogen atoms, $C_{1-6}$ alkyl groups, aryl $C_{1-4}$ alkyl groups, aryl groups, $C_{1-4}$ alkylcarbonyl groups, aryl $C_{1-4}$ alkylcarbonyl groups, arylcarbonyl groups, $C_{1-4}$ alkylsulfonyl groups, aryl $C_{1-4}$ alkylsulfonyl groups or arylsulfonyl groups), a A-B- group (wherein A is the same as defined above, and B is a $C_{1-6}$ alkylene group)},

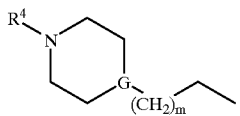

{wherein G is a nitrogen atom or a CH group, $R^4$ is a hydrogen atom, a $C_{1-6}$ alkyl group, a formyl group, an acetyl group, a benzyl group or an amidino group (the amidino group may be substituted with a $C_{1-6}$ alkyl group, a $C_{1-4}$ alkyloxycarbonyl group, an aryl $C_{1-4}$ alkyloxycarbonyl group, an aryloxycarbonyl group or an arylcarbonyl group), and m is 1 or 2} or

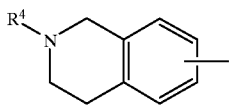

(wherein $R^4$ is the same as defined above), and $X^2$ is a $C_{1-6}$ alkyl group, a $C_{3-6}$ alkenyl group, an aryl $C_{1-4}$ alkyl group or an aryl group.

7. The pyrazolone derivative according to claim 6 or a salt thereof, wherein $X^1$ is

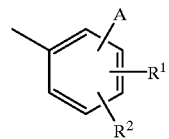

{wherein A is a cyano group, an amino group, an amidino group or a guanidino group (the amino group, the amidino group and the guanidino group may be substituted at a nitrogen atom with a $C_{1-6}$ alkyl group, a $C_{1-4}$ alkyloxycarbonyl group, an aryl $C_{1-4}$ alkyloxycarbonyl group, an aryloxycarbonyl group or an arylcarbonyl group), $R^1$ and $R^2$ are independently hydrogen atoms, halogen atoms, $C_{1-6}$ alkyl groups, hydroxyl groups, $C_{1-4}$ alkyloxy groups, $C_{1-4}$ alkylsulfenyl groups, $C_{1-4}$ alkylsulfinyl groups, $C_{1-4}$ alkylsulfonyl groups, $R^3R^{3'}N$— groups or $R^3R^{3'}NCO$— groups, and $R^3$ and $R^{3'}$ are independently hydrogen atoms, $C_{1-6}$ alkyl groups, aryl $C_{1-4}$ alkyl groups, aryl groups, $C_{1-4}$ alkylcarbonyl groups, aryl $C_{1-4}$ alkylcarbonyl groups, arylcarbonyl groups, $C_{1-4}$ alkylsulfonyl groups, aryl $C_{1-4}$ alkylsulfonyl groups or arylsulfonyl groups), a $H_2N(CH_2)_k$— group (wherein k is an integer of from 1 to 6),

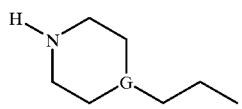

{wherein G is a nitrogen atom or a CH group) or

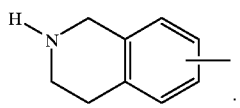

8. The pyrazolone derivative according to claim 7 or a salt thereof, wherein $X^1$ is

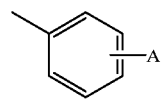

(wherein A is a cyano group or an amidino group), a $H_2N(CH_2)_k$— group (wherein k is an integer of from 1 to 6) or

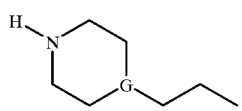

(wherein G is a nitrogen atom or a CH group), $X^2$ is a $C_{1-6}$ alkyl group, a $C_{3-6}$ alkenyl group, an aryl $C_{1-4}$ alkyl group or an aryl group, $Y^1$ is

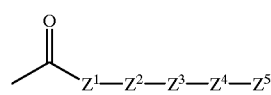

{wherein $Z^1$ is a —$NR^7$— group, $Z^2$ is a $C_{1-3}$ alkylene group, a —$CH_2CO$— group or a —$CH_2CH_2CO$— group, $Z^3$ is an oxygen atom or a —NR$^9$— group, Z$^4$ is a C$_{1-3}$ alkylene group (the C$_{1-3}$ alkylene group may be substituted with R$^{10}$), Z$^5$ is a carboxyl group, a C$_{1-4}$ alkyloxycarbonyl group, an aryl C$_{1-4}$ alkyloxycarbonyl group or an aryloxycarbonyl group, a cyano group, an amidino group (which may be substituted at a nitrogen atom with a C$_{1-6}$ alkyl group, a C$_{1-4}$ alkoxycarbonyl group, an aryl C$_{1-4}$ alkyloxycarbonyl group, an aryloxycarbonyl group or an arylcarbonyl group), and R$^{10}$ is a C$_{1-6}$ alkyl group, an aryl C$_{1-4}$ alkyl group or an aryl group},

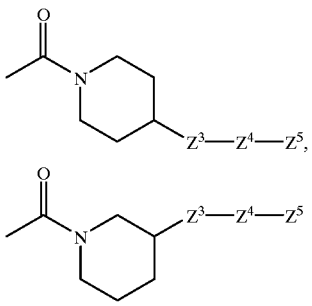

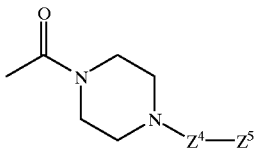

(wherein Z$^3$, Z$^4$ and Z$^5$ are the same as defined above),

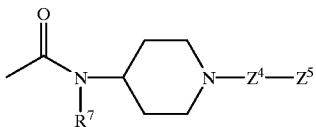

(wherein Z$^4$ and Z$^5$ are the same as defined above) or

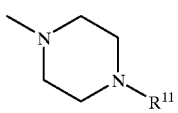

(wherein R$^7$, Z$^4$ and Z$^5$ are the same as defined above), and

Y$^2$ is a hydrogen atom, a pyridyl group a biphenyl group (the pyridyl group and the biphenyl group may be substituted with a halogen atom, a hydroxyl group, a C$_{1-4}$ alkyloxy group or a C$_{1-6}$ alkyl group), a halogen atom, a hydroxyl group, a C$_{1-4}$ alkyloxy group, a C$_{1-6}$ alkyl group or a phenyl group (the phenyl group may be substituted with a halogen atom, a hydroxyl group, a C$_{1-4}$ alkyloxy group, a C$_{1-6}$ alkyl group, a pyridyl group or

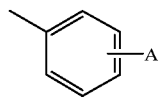

(wherein R$^{11}$ is a hydrogen atom, a C$_{1-6}$ alkyl group, a benzyl group or a formyl group)}.

9. The pyrazolone derivative according to claim 7 or a salt thereof, wherein X$^1$ is

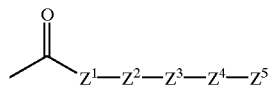

(wherein A is a cyano group or an amidino group), X$^2$ is a C$_{1-6}$ alkyl group, Y$^1$ is

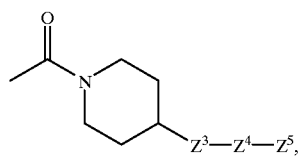

(wherein Z$^1$ is a —NR$^7$— group, Z$^2$ is a C$_{1-3}$ alkylene group, Z$^3$ is an oxygen atom or a —NR$^9$— group, Z$^4$ is a C$_{1-3}$ alkylene group, Z$^5$ is a carboxyl group, a C$_{1-4}$ alkyloxycarbonyl group, an aryl C$_{1-4}$ alkyloxycarbonyl group or an aryloxycarbonyl group, R$^7$ is a hydrogen atom, a C$_{1-6}$ alkyl group, an aryl C$_{1-4}$ alkyl group or an aryl group, and R$^9$ is a hydrogen atom, a formyl group, a C$_{1-4}$ alkylcarbonyl group, an arylcarbonyl group, a pyridylcarbonyl group, a C$_{1-6}$ alkyl group, an aryl C$_{1-4}$ alkyl group or an aryl group),

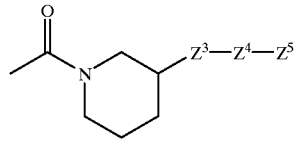

(wherein Z$^3$, Z$^4$ and Z$^5$ are the same as defined above),

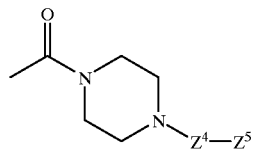

(wherein Z$^4$ and Z$^5$ are the same as defined above) or

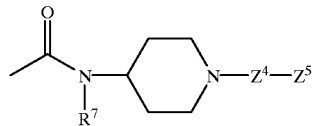

(wherein R$^7$, Z$^4$ and Z$^5$ are the same as defined above), and

Y$^2$ is a hydrogen atom, a biphenyl group (the biphenyl group may be substituted with a cyano group, an amidino group or a halogen atom) or a phenyl group (the phenyl group may be substituted with a halogen atom, a pyridyl group, a C$_{1-6}$ alkyl group or

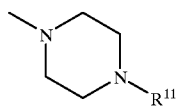

(wherein $R^{11}$ is a $C_{1-6}$ alkyl group)}.

10. A pharmaceutical composition comprising the pyrazolone derivative or a salt thereof, according to claim 1 and a pharmaceutically acceptable carrier.

11. The pharmaceutical composition of claim 10, wherein the pyrazolone derivative or salt thereof is present in antiplatelet aggregation effective amounts.

12. A method of inhibiting platelet aggregation in a patient in need thereof comprising administering to said patient an antiplatelet aggregation effective amount of the pyrazolone derivative or a salt thereof, according to claim 1.

* * * * *